(12) United States Patent
Miyamoto et al.

(10) Patent No.: US 11,079,675 B2
(45) Date of Patent: Aug. 3, 2021

(54) COMPOUND, PHOTOCURABLE COMPOSITION, CURED PRODUCT OF SAME, PRINTING INK, AND PRINTED MATTER CURING THE PRINTING INK

(71) Applicant: DIC Corporation, Tokyo (JP)

(72) Inventors: Masanori Miyamoto, Sakura (JP); Keisuke Wakahara, Tokyo (JP); Tomokazu Yamada, Tokyo (JP)

(73) Assignee: DIC CORPORATION, Tokyo (JP)

( * ) Notice: Subject to any disclaimer, the term of this patent is extended or adjusted under 35 U.S.C. 154(b) by 175 days.

(21) Appl. No.: 16/096,401

(22) PCT Filed: Feb. 21, 2017

(86) PCT No.: PCT/JP2017/006308
§ 371 (c)(1),
(2) Date: Oct. 25, 2018

(87) PCT Pub. No.: WO2017/195428
PCT Pub. Date: Nov. 16, 2017

(65) Prior Publication Data
US 2019/0137872 A1    May 9, 2019

(30) Foreign Application Priority Data

May 13, 2016  (JP) .............................. JP2016-097074

(51) Int. Cl.
*G03F 7/027*    (2006.01)
*C07D 241/04*  (2006.01)
*C07D 295/192* (2006.01)
*C08F 2/50*    (2006.01)
*C09D 11/101*  (2014.01)
*G03F 7/031*   (2006.01)
*C08F 290/06*  (2006.01)

(52) U.S. Cl.
CPC ........... *G03F 7/027* (2013.01); *C07D 241/04* (2013.01); *C07D 295/192* (2013.01); *C08F 2/50* (2013.01); *C09D 11/101* (2013.01); *G03F 7/031* (2013.01); *C08F 290/06* (2013.01)

(58) Field of Classification Search
CPC .......... G03F 7/028; G03F 7/027; G03F 7/031; C07D 241/04
See application file for complete search history.

(56) References Cited

U.S. PATENT DOCUMENTS

| 4,992,547 | A | 2/1991 | Berner et al. |
| 5,077,402 | A | 12/1991 | Desobry et al. |
| 6,022,906 | A | 2/2000 | Ohwa et al. |
| 7,166,647 | B2 | 1/2007 | Herlihy et al. |
| 7,612,122 | B2 | 11/2009 | Herlihy et al. |
| 8,674,089 | B2 | 3/2014 | Fabian et al. |
| 9,957,402 | B2 * | 5/2018 | Miyamoto ................. B41J 2/01 |
| 2008/0021126 | A1 | 1/2008 | Dietliker et al. |

(Continued)

FOREIGN PATENT DOCUMENTS

| CN | 102020728 A | 4/2011 |
| JP | 60-84248 A | 5/1985 |
| JP | 63-264560 A | 11/1988 |

(Continued)

OTHER PUBLICATIONS

International Search Report dated Apr. 11, 2017, issued in counterpart International Application No. PCT/JP2017/006308 (2 pages).

(Continued)

*Primary Examiner* — Daborah Chacko-Davis
(74) *Attorney, Agent, or Firm* — Westerman, Hattori, Daniels & Adrian, LLP

(57) ABSTRACT

A novel compound is used as a novel photopolymerization initiator, the novel compound having a molecular structure represented by general formula 1 below General formula 1

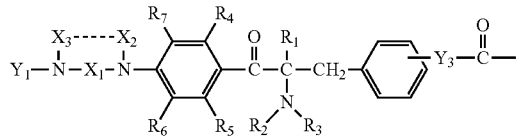

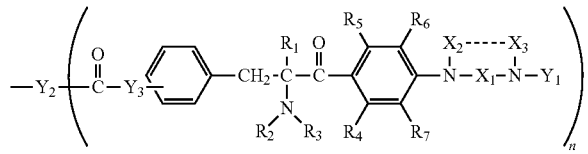

[$R_1$ represents an alkyl group having 1 to 10 carbon atoms, $R_2$ represents an alkyl group having 1 to 12 carbon atoms or the like, $R_3$ represents an alkyl group having 1 to 12 carbon atoms or the like, $R_4$ to $R_7$ each independently represent a hydrogen atom, an alkyl group having 1 to 8 carbon atoms, or the like, $Y_1$ represents an alkyl group having 3 to 19 carbon atoms or the like, $Y_2$ represents an organic linking group, $X_1$ represents an ethylene group or the like, $X_2$ and $X_3$ each represent an ethylene group or the like, $Y_3$ represents a single bond or an alkylidene group, and n represents an integer of 1 to 3].

6 Claims, 4 Drawing Sheets

(56) References Cited

U.S. PATENT DOCUMENTS

2008/0045620 A1    2/2008  Herlihy et al.
2017/0152391 A1*   6/2017  Miyamoto ............ C07C 237/20

FOREIGN PATENT DOCUMENTS

| JP | 2-151822 A | 6/1990 | | |
|----|------------|--------|---|---|
| JP | 10-291969 A | 11/1998 | | |
| JP | 2005-505615 A | 2/2005 | | |
| JP | 2007-525573 A | 9/2007 | | |
| JP | 2008-519760 A | 6/2008 | | |
| JP | 2012-7071 A | 1/2012 | | |
| JP | 2014-19396 A | 2/2014 | | |
| WO | 2011-001928 A1 | 1/2011 | | |
| WO | WO-2015174402 A1 * | 11/2015 | ............ | C07C 237/20 |

OTHER PUBLICATIONS

International Search Report dated Aug. 11, 2015, issued in counterpart International Application No. PCT/JP2015/063603 (2 pages).

\* cited by examiner

COMPOUND, PHOTOCURABLE COMPOSITION, CURED PRODUCT OF SAME, PRINTING INK, AND PRINTED MATTER CURING THE PRINTING INK

TECHNICAL FIELD

The present invention relates to a novel compound useful as a photopolymerization initiator, a photocurable composition containing the photopolymerization initiator, a cured product thereof, a photocurable printing ink containing the photopolymerization initiator, and a printed matter using the printing ink.

BACKGROUND ART

In general, a photocuring system has been widely used from the viewpoint of high production efficiency, lower cost of curing energy, and VOC reduction. In particular, an ultraviolet curing system becomes a mainstream because it has lower equipment introduction cost and smaller installation area than other photocuring systems.

Unlike a reactive monomer which is fixed as a high molecular weight material in a cured film after curing, a photopolymerization initiator used as an essential component in the ultraviolet curing system remains as the photopolymerization initiator or a decomposed product thereof in a cured product. Most of the photopolymerization initiators currently distributed are low-molecular-weight compounds, and thus the remaining photopolymerization initiators or decomposed products thereof also have a low molecular weight. This has been a cause for an odor or the like.

Further, it has recently been pointed out that the residues may migrate to the side of a material in contact with the cured product, and in particular, residues of an ultraviolet curable ink used for a printed matter for food packaging may migrate to the back side of the printed matter in contact with a food, and regulation for the migration of the photopolymerization initiator increasingly becomes severe.

Therefore, an attempt has been made to decrease the migration of the photopolymerization initiator or migration of the decomposed products thereof by allowing the photopolymerization initiator to have a high molecular weight and polyfunctionality. For example, Patent Literature 1 discloses a polymerization initiator having a molecular structure in which alkylphenone-type polymerization-initiating parts are provided at both ends of a bisphenol skeleton.

However, the photopolymerization initiator disclosed in Patent Literature 1 is increased in its molecular weight but unavoidably produces low-molecular-weight decomposed products. For example, in the case of a photopolymerization initiator disclosed as exemplary compound 5 in Patent Literature 1 and represented by a structural formula below,

[Chem. 1]

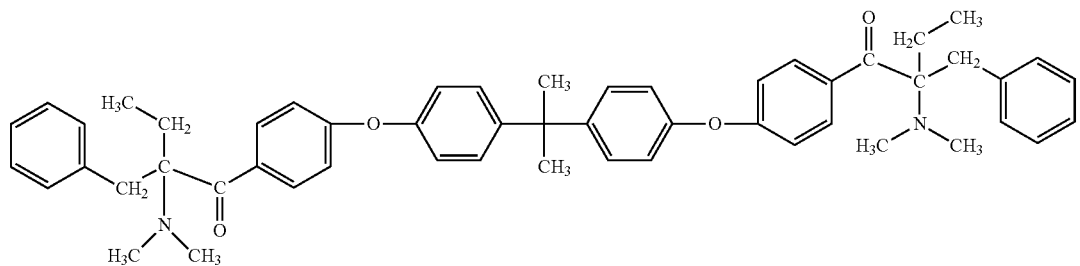

1-phenyl-2-butanone as a decomposed product thereof represented by structural formula a below is unavoidably produced, thereby failing to obtain a satisfactory migration-decreasing effect.

[Chem. 2]

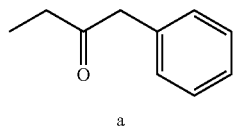

a

In particular, when used for a printing ink for a food packaging material, there is concern about migration of such a low-molecular-weight compound to a food as a content, and in the field of food packaging materials, there is thus a particularly high demand to decrease the migration due to the printing ink.

Also, Patent Literature 2 described below discloses a polymerization initiator having a molecular structure in which an α-aminoalkylphenone-type polymerization-initiating part is bonded through a linking part such as a polyethylene glycol chain or the like. For example, the literature describes an example which uses, as a polymerization initiator, a compound produced by Michael addition reaction of polyethylene glycol diacrylate with 2-benzyl-2-N,N-dimethylamino-1-[4-piperazionophenyl]-1-butanone (Example 1 and Example 3 of Patent Literature 1).

However, the polymerization initiator described in Patent Literature 2 also unavoidably produces a low-molecular-weight compound after decomposition. For example, a compound synthesized in Example 1 and Example 3 of Patent Literature 1 and represented by a structure formula below

[Chem. 3]

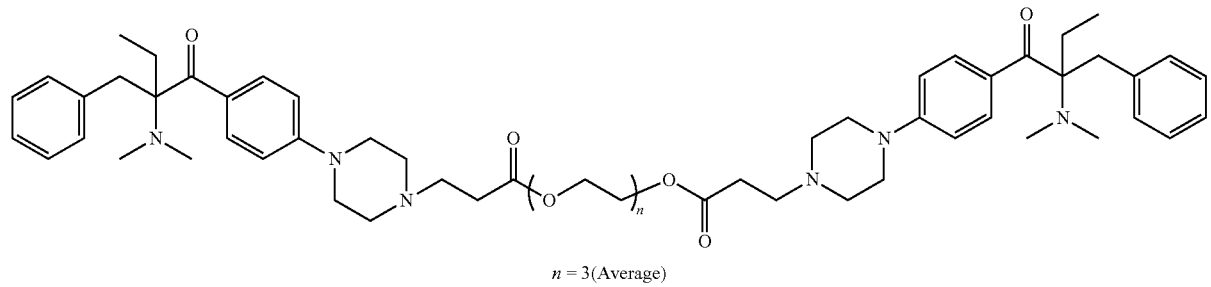

n = 3(Average)

unavoidably produces 1-phenyl-2-butanone represented by structural formula a below.

[Chem. 4]

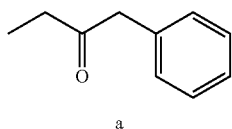

a

CITATION LIST

Patent Literature

PTL 1: Japanese Unexamined Patent Application Publication (Translation of PCT Application) No. 2014-193968

[Chem. 5]

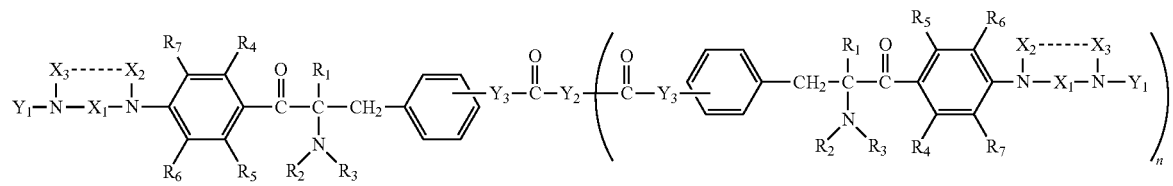

General formula 1

PTL 2: Japanese Unexamined Patent Application Publication (Translation of PCT Application) No. 2008-519760

SUMMARY OF INVENTION

Technical Problem

Accordingly, a problem to be solved by the present invention is to provide a novel compound which when used as a photopolymerization initiator, can decrease migration of an unreacted initiator residue and an initiator decomposed product after curing and can exhibit excellent curability, and also provide a photopolymerization initiator using the same and a photocurable composition containing the photopolymerization initiator.

Solution to Problem

As a result of repeated earnest investigations, the inventors found that by using as a photopolymerization initiator used in a photocurable composition, a high-molecular-weight compound having a plurality of radical generating parts in its molecular structure and having a specified molecular structure, migration of an unreacted residue of the photopolymerization initiator and migration of an initiator decomposed product thereof after curing can be effectively decreased, and excellent curability can be exhibited, leading to the achievement of the present invention.

That is, the present invention relates to a novel compound having a molecular structure represented by general formula 1 below,

[$R_1$ is an alkyl group having 1 to 10 carbon atoms, $R_2$ is an alkyl group having 1 to 12 carbon atoms, a hydroxyalkyl group having 2 to 4 carbon atoms, or an alkyl group having 2 to 4 carbon atoms and substituted by an alkoxy group having 1 or 2 carbon atoms, $R_3$ is an alkyl group having 1 to 12 carbon atoms, a hydroxyalkyl group having 2 to 4 carbon atoms, a methoxyethyl group, or an ethoxyethyl group, $R_2$ and $R_3$ are alkylene groups which are combined to form a cyclic structure together with a nitrogen atom, $R_2$ and $R_3$ are cyclic structure-forming parts which are combined to form a morpholine skeleton, a N-methylpiperazine skeleton, or a 2,6-dimethylmorpholine skeleton together with a nitrogen atom, $R_4$ to $R_7$ are each independently a hydrogen atom, an alkyl group having 1 to 8 carbon atoms, or a phenyl group, $Y_1$ is an alkyl group (y1-1) having 3 to 18 carbon atoms, which has no substituent or a halogen atom or hydroxyl group as a substituent, an aralkyl group (y1-2) having 7 to 19 carbon atoms, a structural part (y1-3) represented by structural formula (y1-3) below

[Chem. 6]

(y1-3)

(in the formula, $R_8$ represents an alkylene group having 2 to 4 carbon atoms, $R_9$ represents a hydrogen atom, a phenyl group, or an alkyl group having 1 to 4 carbon atoms, and m represents an integer of 0 to 20),
a structural part (y1-4) represented by structural formula (y1-4) below

[Chem. 7]

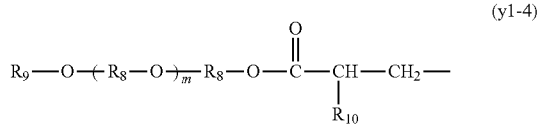
(y1-4)

(in the formula, $R_8$ represents an alkylene group having 2 to 4 carbon atoms, $R_9$ represents a hydrogen atom, a phenyl group, or an alkyl group having 1 to 4 carbon atoms, $R_{10}$ represents a hydrogen atom or a methyl group, and m represents an integer of 0 to 20),
a structural part (y1-5) represented by structural formula (y1-5) below

[Chem. 8]

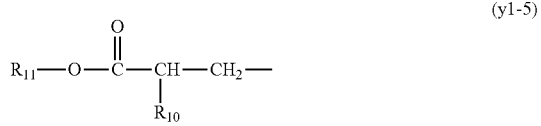
(y1-5)

(in the formula, $R_{10}$ represents a hydrogen atom or a methyl group, and $R_{11}$ represents an alkyl group having 1 to 18 carbon atoms or an aryl group having 6 to 18 carbon atoms),
a structural part (y1-6) represented by structural formula (y1-6) below

[Chem. 9]

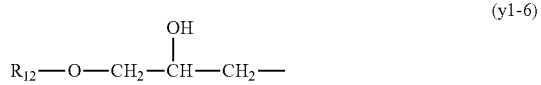
(y1-6)

(in the formula, $R_{12}$ represents an alkyl group having 1 to 18 carbon atoms),
a structural part (y1-7) represented by structural formula (y1-7) below

[Chem. 10]

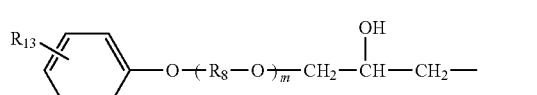
(y1-7)

(in the formula, $R_8$ represents an alkylene group having 2 to 4 carbon atoms, $R_{13}$ represents a hydrogen atom, an alkyl group having 1 to 6 carbon atoms, or a halogen atom, and m represents an integer of 0 to 20),
a structural part (y1-8) represented by structural formula (y1-8) below

[Chem. 11]

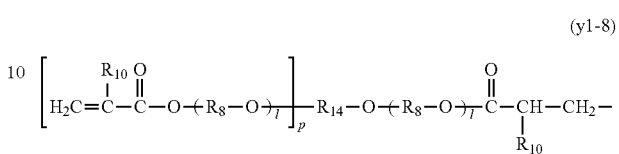
(y1-8)

(in the formula, $R_8$ each independently represent an alkylene group having 2 to 4 carbon atoms, $R_{10}$ represents a hydrogen atom or a methyl group, $R_{14}$ represents a hydrocarbon group having 3 to 25 carbon atoms and (p+1) bonds, l represents an integer of 0 to 20, and p represents an integer of 1 to 3),
or
a structural part (y1-9) represented by structural formula (y1-9) below

[Chem. 12]

(y1-9)

(in the formula, $R_{15}$ represents an alkyl group having 4 to 18 carbon atoms, an aliphatic cyclic hydrocarbon group having 6 to 10 carbon atoms, or an aromatic group),
$X_1$ is an ethylene group, a 1,3-propylene group, a 1,2-propylene group, or a 2,3-propylene group, $X_2$ is a hydrogen atom or a methyl group, $X_3$ is a hydrogen atom, a methyl group, or an ethyl group, or $X_2$ and $X_3$ integrally represent an ethylene group, a 1,3-propylene group, a 1,2-propylene group, or a 2,3-propylene group while forming a covalent bond in a broken line portion, or $X_1$, $X_2$, and $X_3$ integrally represent a tetravalent aliphatic hydrocarbon group which forms a bicyclo ring together with a nitrogen atom and represented by a structural formula below,

[Chem. 13]

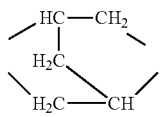

$Y_2$ represents an organic link group having a nitrogen atom or oxygen atom at an end of the structural part and having (n+1) bonds,
$Y_3$ represents a single bond, an alkylene group having 1 to 3 carbon atoms, or an alkylidene group having 1 to 3 carbon atoms, and n represents an integer of 1 to 3].

The present invention further relates to a photopolymerization initiator containing the novel compound.

The present invention further relates to a photocurable composition containing the photopolymerization initiator and a photocurable compound as essential components.

The present invention further relates to a cured product produced by curing the photocurable composition.

The present invention further relates to a photocurable printing ink containing the photocurable composition.

The present invention further relates to a printed matter produced by printing a photocurable printing ink on a substrate, the printed matter containing a compound (2a) represented by structural formula 2a below

[Chem. 14]

General formula 2a

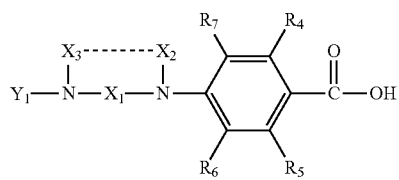

(in the formula, $X_1$, $X_2$, $X_3$, $Y_1$, and $R_4$ to $R_7$ represent the same meanings as in the general formula 1) and compound (2b) represented by structural formula 2b below

[Chem. 15]

General formula 2b

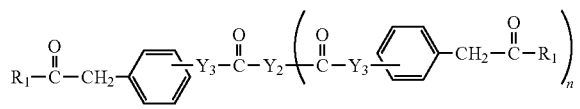

(in the formula, $R_1$, $Y_2$, $Y_3$, and n represent the same meanings as in the general formula 1), wherein the migration concentration of the compound (2a) measured under conditions described below is 50 ppb or less, and the migration concentration of the compound (2b) measured under conditions described below is 50 ppb or less.
[Measurement Condition]
Non-printed milk carton white paper is placed so that the back surface thereof is in contact with a cured ink layer uniformly printed on milk carton paper, and is pressed under a pressing pressure of 40 kg/cm² in an atmosphere of 25° C. for 48 hours. After pressing, a liquid container with a volume of 1000 ml is formed from the non-printed milk carton white paper, and 1000 ml of an aqueous ethanol solution (mixed solution of 95% by weight of ethanol and 5% by weight of pure water) is poured in the liquid container, which is then closed and allowed to stand in an environment at room temperature of 25° C. for 24 hours. As a result, an ink component migrated to the back surface of the milk carton white paper is extracted in the aqueous ethanol solution.

Then, the aqueous ethanol solution is removed from the liquid container, and the elusion concentration of each of the compound (2a) and the compound (2b) is quantitatively determined as the migration concentration by LC/MS/MS analysis.

Advantageous Effects of Invention

According to the present invention, it is possible to provide a novel compound which when used as a photopolymerization initiator, can decrease migration of an unreacted initiator residue and an initiator decomposed product after curing and can exhibit excellent curability, and also provide a photopolymerization initiator using the same and a photocurable composition containing the photopolymerization initiator.

DESCRIPTION OF EMBODIMENTS

Figure 1:
FIG. 1 is a drawing showing a printed matter produced by coloring with a photocurable composition of the present invention used as an ink and curing an ink layer by ultraviolet irradiation.

As described above, a novel compound of the present invention has a molecular structure represented by general formula 1 below.

[Chem. 16]

General formula 1

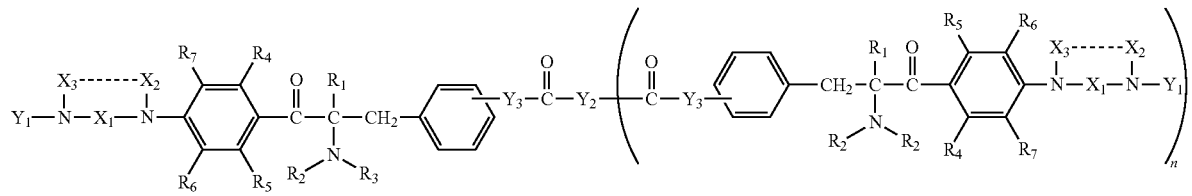

[Chem. 17]

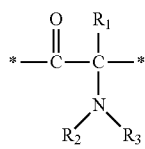

In the present invention, it is noteworthy that excellent curability can be exhibited regardless of a relatively high molecular weight and a relatively small amount of a radical generating part.

In the general formula 1, $R_1$ represents an alkyl group having 1 to 10 carbon atoms, such as a methyl group, an ethyl group, a propyl group, an isopropyl group, a n-butyl group, an isobutyl group, a tert-butyl group, a sec-butyl group, a pentyl group, a hexyl group, a heptyl group, an octyl group, a nonyl group, a decyl group, a 2-ethylbutyl group, an isopentyl group, a 1-methylpentyl group, a 1,3-dimethylbutyl group, a 1-methylhexyl group, an isoheptyl group, a 1,1,3,3-tetramethylbutyl group, a 2,2,4,4-tetramethylbutyl group, a 1-methylheptyl group, a 3-methylheptyl group, a 2-ethylhexyl group, a 1,1,3-trimethylhexyl group, a 1,1,3,3-tetramethylpentyl group, an isodecyl group, or the like. Among these, an ethyl group is preferred in view of the reactivity of radical generated by light irradiation.

Next, $R_2$ and $R_3$ each independently represent a linear or branched alkyl group having 1 to 12 carbon atoms, such as a methyl group, an ethyl group, a propyl group, an isopropyl group, a n-butyl group, an isobutyl group, a tert-butyl group, a sec-butyl group, a pentyl group, a hexyl group, a heptyl group, an octyl group, a nonyl group, a decyl group, an undecyl group, a dodecyl group, or the like; a hydroxyalkyl group having 2 to 4 carbon atoms, such as a hydroxyethyl group, a hydroxypropyl group, a hydroxybutyl group, or the like; a methoxyethyl group; an ethoxyethyl group; an alkylene group which forms a cyclic structure by combination of $R_2$ and $R_3$ together with a nitrogen atom, that is, a butylene group or a pentene group which forms, as a structure corresponding to the following,

[Chem. 18]

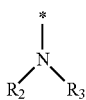

a pyrrolidine structure or piperizine structure represented by structural formula below, or

[Chem. 19]

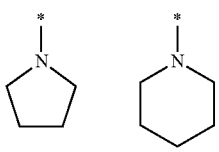

a cyclic structure-forming part which forms a morpholine skeleton, a N-methylpiperazine skeleton, or a 2,6-dimethylmorpholine skeleton by combination of $R_2$ and $R_3$ together with a nitrogen atom, that is, a structural part which forms, as a structure corresponding to the following,

[Chem. 20]

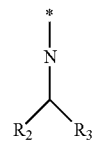

a structural formula below.

[Chem. 21]

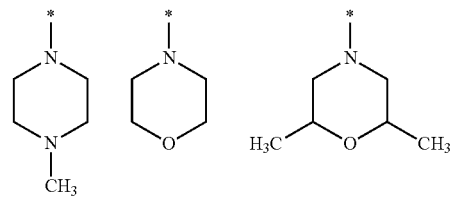

Among these, a linear or branched alkyl group having 1 to 12 carbon atoms is preferred in view of high yield of synthesis.

$R_4$ to $R_7$ each independently represent a hydrogen atom; an alkyl group having 1 to 8 carbon atoms, such as a methyl group, an ethyl group, a propyl group, an isopropyl group, a n-butyl group, an isobutyl group, a tert-butyl group, a sec-butyl group, a pentyl group, a hexyl group, a heptyl group, an octyl group, a 2-ethylbutyl group, an isopentyl group, a 1-methylpentyl group, a 1,3-dimethylbutyl group, a 1-methylhexyl group, an isoheptyl group, a 1,1,3,3-tetramethylbutyl group, a 2,2,4,4-tetramethylbutyl group, a 1-methylheptyl group, a 3-methylheptyl group, a 2-ethylhexyl group, or the like; or a phenyl group. Among these, all of $R_4$ to $R_7$ are preferably hydrogen atoms in view of easy availability of raw materials.

Further, $X_1$ represents an ethylene group, a 1,3-propylene group, a 1,2-propylene group, or a 2,3-propylene group, $X_2$ represents a hydrogen atom or a methyl group, $X_3$ represents a hydrogen atom, a methyl group, or an ethyl group, or $X_2$ and $X_3$ integrally represent an ethylene group, a 1,3-propylene group, a 1,2-propylene group, or a 2,3-propylene group while forming a covalent bond in a broken line portion, or $X_1$, $X_2$, and $X_3$ integrally represent a tetravalent aliphatic hydrocarbon group which forms a bicyclo ring together with a nitrogen atom and is represented by structural formula below.

[Chem. 22]

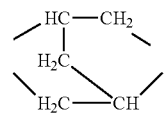

Among these, examples of a structural part formed by $X_1$, $X_2$, and $X_3$ together with a nitrogen atom and represented by a partial structural formula below

[Chem. 23]

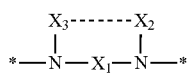

(in the formula, * represents a bond with another structural part) include the following:

[Chem. 24]

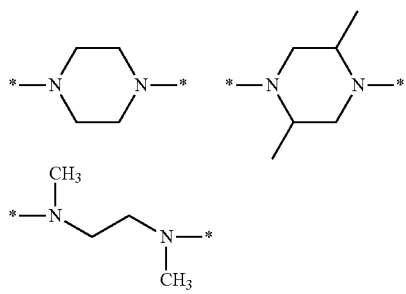

(in the formulae, * represents a bond with another structural part), but in view of the high yield of [Step V] of a method for producing the novel compound of the present invention described below, preferred is that represented by a structural formula below.

[Chem. 25]

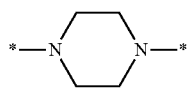

Next, $Y_1$ is a linear or branched alkyl group such as a propyl group, an isopropyl group, a n-butyl group, an isobutyl group, a tert-butyl group, a sec-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a 2-ethylbutyl group, an isopentyl group, a 1-methylpentyl group, a 1,3-dimethylbutyl group, a 1-methylhexyl group, an isoheptyl group, a 1,1,3,3-tetramethylbutyl group, a 2,2,4,4-tetramethylbutyl group, a 1-methylheptyl group, a 3-methylheptyl group, a 2-ethylhexyl group, a 1,1,3-trimethylhexyl group, a 1,1,3,3-tetramethylpentyl group, an isodecyl group, a 1-methylundecyl group, a 1,1,3,3,5,5-hexamethylhexyl group, or the like; a cycloheptyl group, a cyclohexyl group, a cyclopentyl group; an alkyl group (y1-1) having 3 to 18 carbon atoms, which has no substituent or has a halogen atom or a hydroxyl group as a substituent, such as a 1-fluoropropyl group, a 1,1,1-trifluoropropyl group, a 1,1,1-trifluorobutyl group, a 2-trifluoromethylpropyl group, a 1,1,1,2,2-pentafluoropropyl group, a 1,1,1,2,2-pentafluoropentyl group, a 1,1,1,2,2,3,3-pentafluoropropyl group, a 1,1,1,2,2,3,3-pentafluorobutyl group, a 2-(perfluorobutyl) ethyl group, a 1-chloropropyl group, a 1,1,1-trichloropropyl group, a 1-chlorobutyl group, a 1,1,1-trichlorobutyl group, a 1-chlorohexyl group, a 1,1,1-trichlorohexyl group, a 1-chlorododecyl group, a 1,1,1-trichlorododecyl group, a 1-chlorooctadecyl group, a 1,1,1-trichlorooctadecyl group, a 1-hydroxypropyl group, a 2-hydroxypropyl group, a 1-hydroxybutyl group, a 1-hydroxyhexyl group, a 1-hydroxydodecyl group, a 1-hydroxyoctadecyl group, or the like; an aralkyl group (y1-2) having 7 to 19 carbon atoms, such as a benzyl group, a methoxybenzyl group, a chlorobenzyl group, a hydroxybenzyl group, a phenethyl group, a phenylbenzyl group, a methoxyphenylbenzyl group, a naphthylmethyl group, a methoxynaphthylmethyl group, a phenylpropyl group, a phenylpropenyl group, a phenoxybenzyl group, a methylthiobenzyl group, a terphenylmethyl group, or the like;

a structural part (y1-3) represented by structural formula below

[Chem. 26]

 (y1-3)

(in the formula, $R_8$ represents an alkylene group having 2 to 4 carbon atoms, $R_9$ represents a hydrogen atom, a phenyl group, or an alkyl group having 1 to 4 carbon atoms, and m represents an integer of 0 to 20), a structural part (y1-4) represented by structural formula (y1-4) below

[Chem. 27]

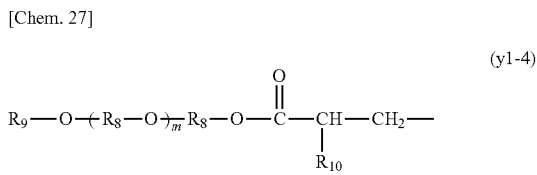 (y1-4)

(in the formula, $R_8$ represents an alkylene group having 2 to 4 carbon atoms, $R_9$ represents a hydrogen atom, a phenyl group, or an alkyl group having 1 to 4 carbon atoms, $R_{10}$ represents a hydrogen atom or a methyl group, and m represents an integer of 0 to 20), a structural part (y1-5) represented by structural formula (y1-5) below

[Chem. 28]

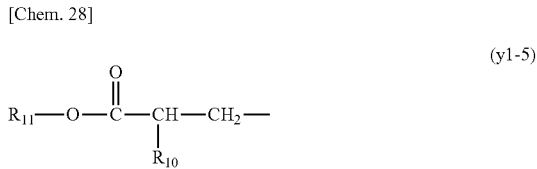 (y1-5)

(in the formula, $R_{10}$ represents a hydrogen atom or a methyl group, and $R_{11}$ represents an alkyl group having 1 to 18 carbon atoms or an aryl group having 6 to 18 carbon atoms), a structural part (y1-6) represented by structural formula (y1-6) below

[Chem. 29]

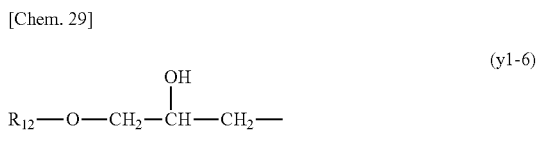 (y1-6)

(in the formula, $R_{12}$ represents an alkyl group having 1 to 18 carbon atoms), a structural part (y1-7) represented by structural formula (y1-7) below

[Chem. 30]

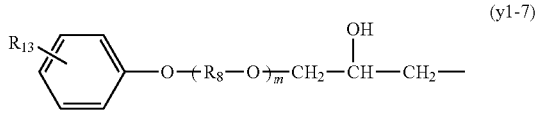

(in the formula, $R_8$ represents an alkylene group having 2 to 4 carbon atoms, $R_{13}$ represents a hydrogen atom, an alkyl group having 1 to 6 carbon atoms, or a halogen atom, and m represents an integer of 0 to 20),
a structural part (y1-8) represented by structural formula (y1-8) below

[Chem. 31]

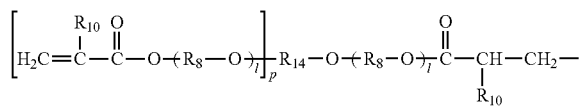

(in the formula, $R_8$ represents an alkylene group having 2 to 4 carbon atoms, $R_{10}$ represents a hydrogen atom or a methyl group, $R_{14}$ represents a hydrocarbon group having 5 to 18 carbon atoms and (p+1) bonds, l represents an integer of 0 to 20, and p represents an integer of 1 to 3), and
a structural part (y1-9) represented by structural formula (y1-9) below

[Chem. 32]

(in the formula, $R_{15}$ represents an alkyl group having 4 to 18 carbon atoms, an aliphatic cyclic hydrocarbon group having 6 to 10 carbon atoms, or an aromatic group).

In the structural formula (y1-3), examples of $R_8$, an alkylene group having 2 to 4 carbon atoms, include a n-propylene group, a 1,2-propylene group, a n-butylene group, a 2-methyl-propane-1,2-diyl group, and the like, and examples of $R_9$ as an alkyl group having 1 to 4 carbon atoms include a methyl group, an ethyl group, a propyl group, an isopropyl group, a n-butyl group, an isobutyl group, a tert-butyl group, a sec-butyl group, and the like.

In the structural part (y1-4), $R_8$ and $R_9$ represent the same meanings as in the structural formula (y1-3).

In the structural formula (y1-5), examples of $R_{11}$, an alkyl group having 1 to 18 carbon atoms or an alkyl group having 1 to 18 carbon atoms, include linear or branched alkyl groups such as a methyl group, an ethyl group, a propyl group, an isopropyl group, a n-butyl group, an isobutyl group, a tert-butyl group, a sec-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a 2-ethylbutyl group, an isopentyl group, a 1-methylpentyl group, a 1,3-dimethylbutyl group, a 1-methylhexyl group, an isoheptyl group, a 1,1,3,3-tetramethylbutyl group, a 2,2,4,4-tetramethylbutyl group, a 1-methylheptyl group, a 3-methylheptyl group, a 2-ethylhexyl group, a 1,1,3-trimethylhexyl group, a 1,1,3,3-tetramethylpentyl group, an isodecyl group, a 1-methylundecyl group, a 1,1,3,3,5,5-hexamethylhexyl group, and the like; cycloalkyl groups such as a cycloheptyl group, a cyclohexyl group, a cyclopentyl group, and the like. On the other hand, examples of an aryl group having 6 to 18 carbon atoms include a phenyl group, a benzyl group, a phenethyl group, a biphenyl group, a naphthyl group, a tolyl group, a xylyl group, a mesityl group, a cumenyl group, a chlorophenyl group, a bromophenyl group, a chloromethylphenyl group, a hydroxyphenyl group, a methoxyphenyl group, an ethoxyphenyl group, a phenoxyphenyl group, an acetoxyphenyl group, a benzoyloxyphenyl group, a methylthiophenyl group, a phenylthiophenyl group, a methylaminophenyl group, a dimethylaminophenyl group, an acetylaminophenyl group, a carboxyphenyl group, a methoxycarbonylphenyl group, a phenoxycarbonylphenyl group, a N-phenylcarbamoylphenyl group, a cyanophenyl group, a sulfophenyl group, a sulfonatophenyl group, a phosphonophenyl group, a phosphonatophenyl group, and the like.

In the structural formula (y1-6), examples of $R_{12}$ as an alkyl group having 1 to 18 carbon atoms include linear or branched alkyl groups such as a methyl group, an ethyl group, a propyl group, an isopropyl group, a n-butyl group, an isobutyl group, a tert-butyl group, a sec-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a 2-ethylbutyl group, an isopentyl group, a 1-methylpentyl group, a 1,3-dimethylbutyl group, a 1-methylhexyl group, an isoheptyl group, a 1,1,3,3-tetramethylbutyl group, a 2,2,4,4-tetramethylbutyl group, a 1-methylheptyl group, a 3-methylheptyl group, a 2-ethylhexyl group, a 1,1,3-trimethylhexyl group, a 1,1,3,3-tetramethylpentyl group, an isodecyl group, a 1-methylundecyl group, a 1,1,3,3,5,5-hexamethylhexyl group, and the like, and cycloalkyl groups such as a cycloheptyl group, a cyclohexyl group, a cyclopentyl group, and the like.

In the structural formula (y1-7), $R_8$ represents the same meanings as $R_8$ in the structural part (y1-3). Examples of $R_{13}$ as an alkyl group having 1 to 6 carbon atoms include a methyl group, an ethyl group, a propyl group, an isopropyl group, a n-butyl group, an isobutyl group, a tert-butyl group, a sec-butyl group, a pentyl group, a hexyl group, a 2-ethylbutyl group, an isopentyl group, a 1-methylpentyl group, a 1,3-dimethylbutyl group, and the like, and examples of a halogen atom include a bromine atom, a chlorine atom, a fluorine atom, and the like.

In the structural formula (y1-8), $R_8$ represents the same meanings as $R_8$ in the structural part (y1-3). Examples of $R_{14}$ as a hydrocarbon group having 3 to 25 carbon atoms and (p+1) bonds include aliphatic polyhydric alcohol residues such as a glycerol residue, a trimethylolpropane residue, a pentaerythritol residue, and the like; a n-propylene group, a 1,2-propylene group, a n-butylene group, a 2-methyl-propane-1,2-diyl group, a 1,5-pentanediyl group, a 1,6-hexanediyl group, a 1,7-heptanediyl group, a 1,8-octanediyl group, a 1,9-nonanediyl group, a 1,10-decanediyl group, a 3,8-decanediyl group, a 1,11-undecanediyl group, a 1,12-dodecanediyl group, a 1,13-tridecanediyl group, a 1,14-tetradecanediyl group, a 1,15-pentadecanediyl group, a 1,16-hexadecanediyl group, a 1,17-heptadecanediyl group, a 1,18-octadecanediyl group, a 1,19-nonadecanediyl group, a 1,20-eicosanediyl group, a 1,21-heneicosanediyl group, a 1,22-docosanediyl group, 1,23-tricosanediyl group, a 1,24-tetracosanediyl group, a 1,25-pentacosanediyl group, and the like.

Herein, the term "residue" represents a hydrocarbon structural part excluding a hydroxyl group of a polyhydric alcohol.

Among the structural parts represented by $Y_1$ in the general formula 1 detailed above, in view of easy introduction of $Y_1$ during synthesis of the novel compound and the good effect of decreasing migration after curing, particularly preferred are the alkyl group (y1-1) having 3 to 18 carbon atoms, the structural part (y1-4) represented by the structural formula (y1-4) below

[Chem. 33]

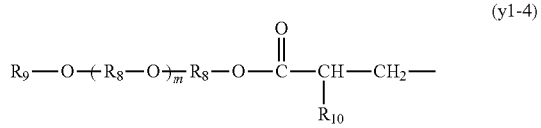
(y1-4)

(in the formula, $R_8$ represents an alkylene group having 2 to 4 carbon atoms, $R_9$ represents a hydrogen atom, a phenyl group, or an alkyl group having 1 to 4 carbon atoms, $R_{10}$ represents a hydrogen atom or a methyl group, and m represents an integer of 0 to 20),
the structural part (y1-5) represented by the structural formula (y1-5) below

[Chem. 34]

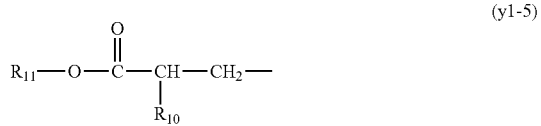
(y1-5)

(in the formula, $R_{10}$ represents a hydrogen atom or a methyl group, and $R_{11}$ represents an alkyl group having 1 to 18 carbon atoms or an aryl group having 6 to 18 carbon atoms), and the structural part (y1-8) represented by the structural formula (y1-8) below

[Chem. 35]

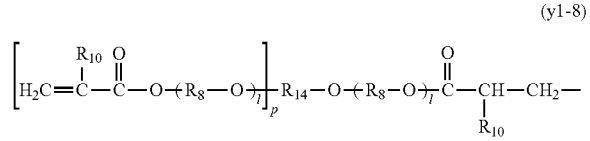
(y1-8)

(in the formula, $R_8$ each independently represent an alkylene group having 2 to 4 carbon atoms, $R_{10}$ represents a hydrogen atom or a methyl group, $R_{14}$ represents a hydrocarbon group having 3 to 25 carbon atoms and (p+1) bonds, l represents an integer of 0 to 20, and p represents an integer of 1 to 3). In particular, in view of the more significant effect of preventing migration due to having an acryloyl group, the structural part (y1-8) is particularly preferred.

Next, in the general formula 1, a structural part represented by structural formula 1a below

[Chem. 36]

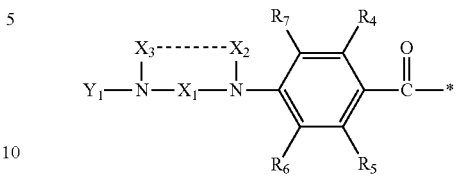
Structural formula 1a (in the structural formula 1a, $X_1$, $X_2$, $X_3$, $R_4$ to $R_7$, and $Y_1$ represent the same meanings as in the general formula 1) can be arbitrarily selected from the various structures described above, but the total mass number of a portion represented by the structural formula 1a is preferably 300 to 2000 in view of the effect of decreasing migration in a printed matter. In the structural formula 1a, * represents a bond with another structural part.

Next, as described above, $Y_2$ is an organic bonding group having (n+1) bonds and a nitrogen atom or oxygen atom at an end of the structural part. Specifically, because of the easy availability of raw materials and easy control of reaction, preferred is an amide bond-forming type structural part selected from a group consisting of structural parts (y2-1) to (y2-6) described below or an ester bond-forming type structural part represented by structural parts (y2-7) to (y2-9) described below.

The structural part (y2-1) is a structural part in which n in the general formula 1 is 1 and which is represented by a structural formula below

[Chem. 37]

(y2-1)

(in the formula, $R_{16}$ represents a linear or cyclic alkylene group having 2 to 18 carbon atoms, a phenylene group, a xylylene group, a phenylene group having an alkyl group having 1 to 3 carbon atoms as a nuclear substituent, or a xylylene group having an alkyl group having 1 to 3 carbon atoms as a nuclear substituent).

In the structural formula (y2-1), examples of a linear or cyclic alkylene group having 2 to 18 carbon atoms and constituting $R_{16}$ include an ethylene group, a n-propylene group, a 1,2-propylene group, a n-butylene group, a 2-methyl-propane-1,2-diyl group, a 1,5-pentanediyl group, a 1,6-hexanediyl group, a 1,7-heptanediyl group, a 1,8-octanediyl group, a 1,9-nonanediyl group, a 1,10-decanediyl group, a 3,8-decanediyl group, a 1,11-undecanediyl group, a 1,12-dodecanediyl group, a 1,13-tridecanediyl group, a 1,14-tetradecanediyl group, a 1,15-pentadecanediyl group, a 1,16-hexadecanediyl group, a 1,17-heptadecanediyl group, a 1,18-octadecanediyl group, a 1,4-cyclohexanediyl group, and the like.

Examples of a phenylene group having an alkyl group having 1 to 3 carbon atoms as a nuclear substituent in the structural formula (y2-1) include a methylphenylene group, an ethylphenylene group, a n-propylphenylene group, and an iso-propylphenylene group. Examples of a xylylene group having an alkyl group having 1 to 3 carbon atoms as a nuclear substituent include a methylxylylene group, an ethylxylylene group, a n-propylxylylene group, and an iso-propylxylylene group.

Among these, preferred examples of the structural part (Y2-1) include those represented by structural formulae below.

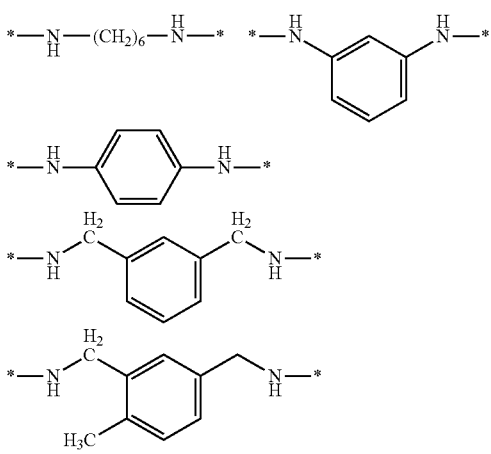

These are preferred in view of the easy availability of a diamine compound used as a constitutive raw material of the structure in [Step IV] of a method for producing the novel compound of the present invention described below. In each of the structural formulae, * represents a bond with another structural part.

The structural part (y2-2) has a n of 1 in the general formula 1 and is represented by structural formula below

[Chem. 38]

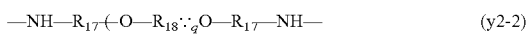
(y2-2)

(in the formula, $R_{17}$ represents a linear or branched alkylene group having 2 to 6 carbon atoms or a phenylene group, $R_{18}$ represents a linear or branched alkylene group having 2 to 6 carbon atoms or a phenylene group, and q represents an integer of 0 to 12).

In the structural formula (y2-2), examples of a linear or branched alkylene group having 2 to 6 carbon atoms and constituting $R_{17}$ and $R_{17}$ include an ethylene group, a n-propylene group, a 1,2-propylene group, a n-butylene group, a 2-methyl-propane-1,2-diyl group, a 1,5-pentanediyl group, and a 1,6-hexanediyl group.

Preferred examples of the structural part (y2-2) include those represented by structural formulae below.

[Chem. 39]

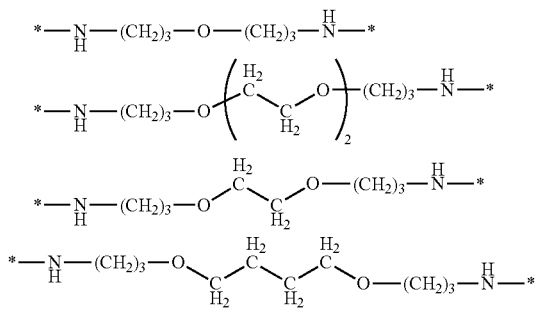

These are preferred in view of the easy availability of a diamine compound used as a constitutive raw material of the structure in [Step IV] of a method for producing the novel compound of the present invention described below. In each of the structural formulae, * represents a bond with another structural part.

The structural part (y2-3) has a n of 1 in the general formula 1 and is represented by structural formula (y2-3) below

[Chem. 40]

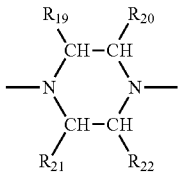
(y2-3)

(in the formula, $R_{19}$ to $R_{22}$ each independently represent a hydrogen atom or a linear or branched alkyl group having 1 to 3 carbon atoms). In the structural formula, examples of a linear or branched alkyl group having 1 to 3 carbon atoms and constituting $R_{19}$ to $R_{22}$ include a methyl group, an ethyl group, a propyl group, and an isopropyl group.

Preferred examples of the structural part (y2-3) include those represented by structural formulae below.

[Chem. 41]

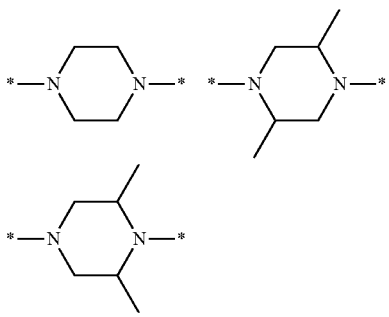

These are preferred in view of the easy availability of a diamine compound used as a constitutive raw material of the structure in [Step IV] of a method for producing the novel compound of the present invention described below. In each of the structural formulae, * represents a bond with another structural part.

The structural part (y2-4) has a n of 1 in the general formula 1 and is represented by structural formula (y2-4) below

[Chem. 42]

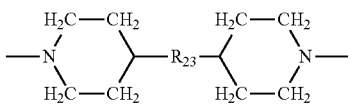
(y2-4)

(in the formula, $R_{23}$ represents an oxygen atom, a methylene group, an ethylene group, an ethylidene group, a 2,2-propylene group, or a 1,3-propylene group).

Preferred examples of the structural part (y2-4) include that represented by a structural formula below.

[Chem. 43]

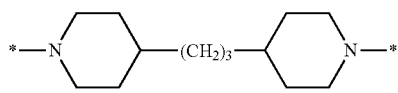

This is preferred in view of the easy availability of a diamine compound used as a constitutive raw material of the structure in [Step IV] of a method for producing the novel compound of the present invention described below. In the structural formula, * represents a bond with another structural part.

The structural part (y2-5) has a n of 1 in the general formula 1 and is represented by structural formula (y2-5) below

[Chem. 44]

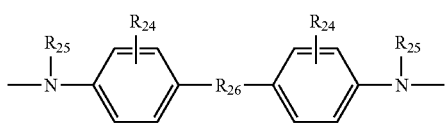
(y2-5)

(in the formula, $R_{24}$ each independently represent a hydrogen atom or a linear or branched alkyl group having 1 to 3 carbon atoms, $R_{25}$ each independently represent a hydrogen atom or a linear or branched alkyl group having 1 to 3 carbon atoms, and $R_{26}$ represents an oxygen atom, a methylene group, a 2,2-propylene group, a sulfonyl group, or a carbonyl group). In the structural formula, examples of a linear or branched alkyl group having 1 to 3 carbon atoms and constituting $R_{24}$ or $R_{25}$ include a methyl group, an ethyl group, a propyl group, and an isopropyl group.

Preferred examples of the structural part (y2-5) include those represented by structural formulae below.

[Chem. 45]

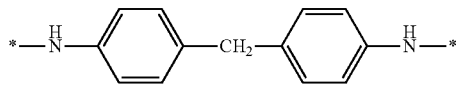

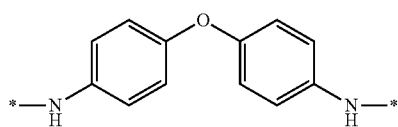

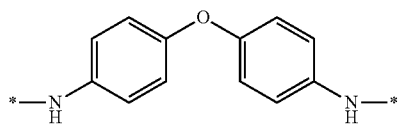

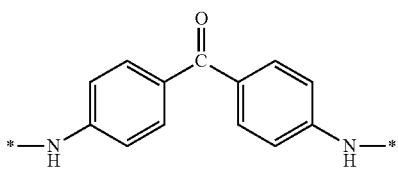

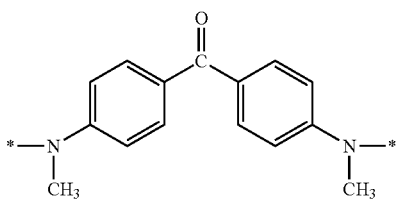

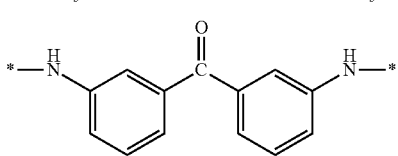

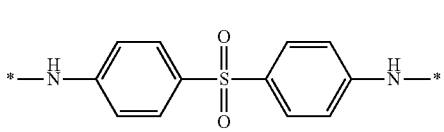

These are preferred in view of the easy availability of a diamine compound used as a constitutive raw material of the structure in [Step IV] of a method for producing the novel compound of the present invention described below. In each of the structural formulae, * represents a bond with another structural part.

The structural part (y2-6) has a n of 2 or 3 in the general formula 1 and is represented by structural formula (y2-6) below

[Chem. 46]

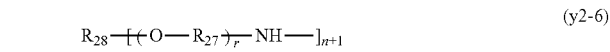
(y2-6)

(in the formula, $R_{27}$ represents an alkylene group having 2 to 6 carbon atoms, and $R_{28}$ represents a hydrocarbon group having 4 to 12 carbon atoms and a number of bonds of (n+1)). Examples of an alkylene group having 2 to 6 carbon atoms constituting $R_{27}$ include an ethylene group, a n-propylene group, a 1,2-propylene group, a n-butylene group, a 2-methyl-propane-1,2-diyl group, a 1,5-pentanediyl group, and a 1,6-hexanediyl group. Examples of a hydrocarbon group having 4 to 12 carbon atoms and a number of bonds of (n+1) and constituting $R_{28}$ include polyhydric alcohol residues such as a trimethylolpropane residue, a pentaerythritol residue, a glycerol residue, and a ditrimethylolpropane residue. Herein, the term "residue" represents a hydrocarbon structural part excluding a hydroxyl group of the polyhydric alcohol.

Preferred examples of the structural part (y2-6) include those represented by structural formulae below.

[Chem. 47]

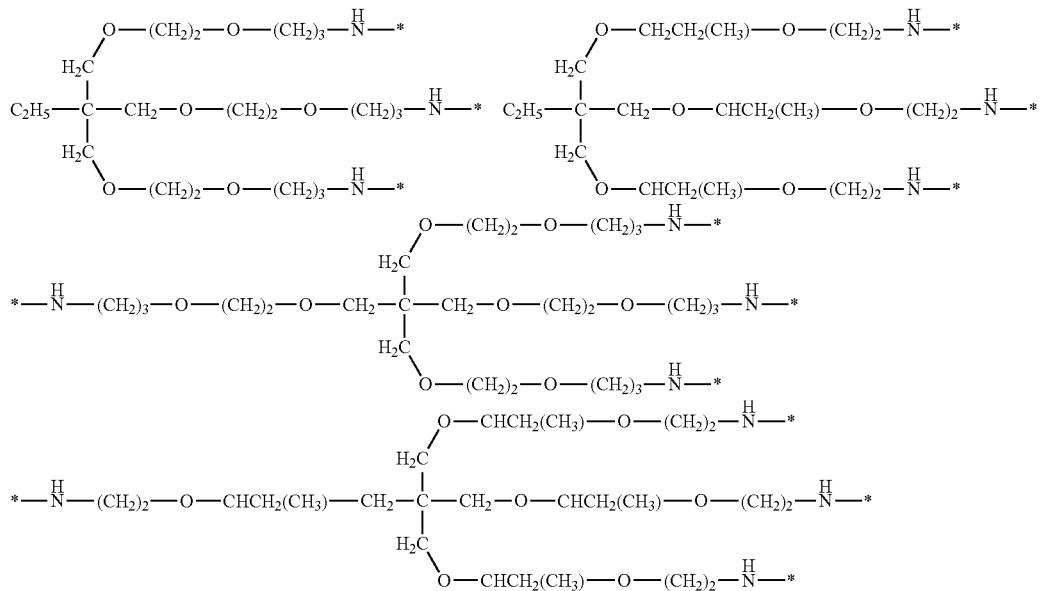

These are preferred in view of the easy availability of a diamine compound used as a constitutive raw material of the structure in [Step IV] of a method for producing the novel compound of the present invention described below. In each of the structural formulae, * represents a bond with another structural part.

Next, the structural part (y2-7) which is an ester bond-forming type structural part has an n of 1 in the general formula 1 and is represented by structural formula (y2-7) below

[Chem. 48]

$\qquad$ (y2-7)

(in the formula, $R_{29}$ represents a linear, branched, or cyclic alkylene group having 2 to 18 carbon atoms, a phenylene group, or a xylylene group). Examples of a linear, branched, or cyclic alkylene group having 2 to 18 carbon atoms and constituting $R_{29}$ include an ethylene group, a n-propylene group, a 1,2-propylene group, a n-butylene group, a 2-methyl-propane-1,2-diyl group, a 1,5-pentanediyl group, a 1,6-hexanediyl group, a 1,7-heptanediyl group, a 1,8-octanediyl group, a 1,9-nonanediyl group, a 1,10-decanediyl group, a 3,8-decanediyl group, a 1,11-undecanediyl group, a 1,12-dodecanediyl group, a 1,13-tridecanediyl group, a 1,14-tetradecanediyl group, a 1,15-pentadecanediyl group, a 1,16-hexadecanediyl group, a 1,17-heptadecanediyl group, a 1,18-octadecanediyl group, and a 1,4-cyclohexanediyl group.

Preferred examples of the structural part (y2-7) include those represented by structural formulae below.

[Chem. 49]

-continued

These are preferred in view of the easy availability of a diol compound used as a constitutive raw material of the structure in [Step IV] of a method for producing the novel compound of the present invention described below. In each of the structural formulae, * represents a bond with another structural part.

Next, the structural part (y2-8) which is an ester bond-forming type structural part has an n of 1 in the general formula 1 and is represented by structural formula (y2-8) below

[Chem. 50]

—O—$R_{30}$—(—O—$R_{30}$—)$_q$—O— (y2-8)

(in the formula, $R_{30}$ each independently represent an alkylene group having 2 to 6 carbon atoms, and q represents an integer of 1 to 20). Examples of an alkylene group having 2 to 6 carbon atoms and constituting $R_{30}$ include an ethylene group, a n-propylene group, a 1,2-propylene group, a n-butylene group, a 2-methyl-propane-1,2-diyl group, a 1,5-pentanediyl group, and a 1,6-hexanediyl group.

Preferred examples of the structural part (y2-8) include those represented by structural formulae below.

[Chem. 51]

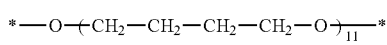

These are preferred in view of the easy availability of a diol compound used as a constitutive raw material of the structure in [Step IV] of a method for producing the novel compound of the present invention described below. In each of the structural formulae, * represents a bond with another structural part.

The structural part (y2-9) which is an ester bond-forming type structural part has an n of 2 or 3 in the general formula 1 and is represented by structural formula (y2-9) below

[Chem. 52]

(in the formula, $R_{31}$ represents a hydrocarbon group having 4 to 12 carbon atoms and a number of bonds of (n+1)), $R_{32}$ represents an alkylene group having 2 to 6 carbon atoms, and s represents an integer of 0 to 3).

Examples of a hydrocarbon group having 4 to 12 carbon atoms and a number of bonds of (n+1) and constituting $R_{31}$ include polyhydric alcohol residues such as a trimethylolpropane residue, a pentaerythritol residue, a glycerol residue, and a ditrimethylolpropane residue. Herein, the term "residue" represents a hydrocarbon structural part excluding a hydroxyl group of the polyhydric alcohol.

Further, examples of an alkylene group having 2 to 6 carbon atoms and constituting $R_{32}$ include an ethylene group, a n-propylene group, a 1,2-propylene group, a n-butylene group, a 2-methyl-propane-1,2-diyl group, a 1,5-pentanediyl group, and a 1,6-hexanediyl group.

Preferred examples of the structural part (y2-9) include those represented by structural formulae below.

[Chem. 53]

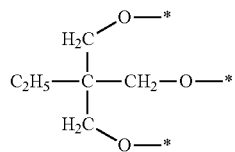

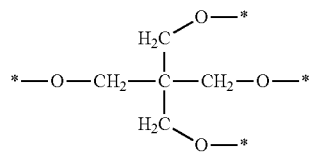

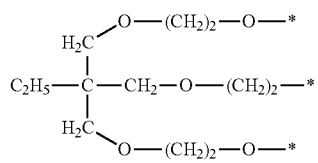

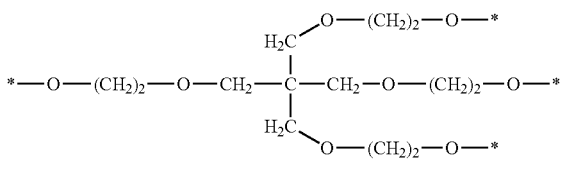

These are preferred in view of the easy availability of a diol compound used as a constitutive raw material of the structure in [Step IV] of a method for producing the novel compound of the present invention described below. In each of the structural formulae, * represents a bond with another structural part.

In the general formula 1 described in detail above, among $Y_2$, the amide bond-forming type structural part selected from the group consisting of the structural parts (y2-1) to (y2-6) is preferred in view of excellent chemical stability of a product, and the structural part (y2-1), the structural part (y2-2), and the structural part (y2-3) are particularly preferred in view of easy availability of a raw material and excellent photocurability. In particular, the structural part (y2-3) selected from structures below is preferred.

[Chem. 54]

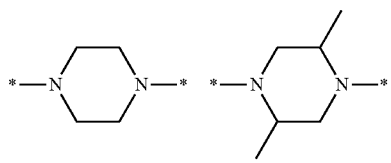

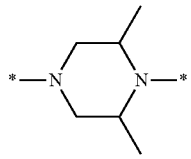

These are preferred in view of the point that an intermediate can be easily crystallized and can be easily purified during production.

Next, $Y_3$ in the general formula 1 represents a single bond, an alkylene group having 1 to 3 carbon atoms, or an alkylidene group having 2 or 3 carbon atoms, and examples of an alkylene group having 1 to 3 carbon atoms include a methylene group, an ethylene group, a n-propylene group, and a 1,2-propylene group, and examples of an alkylidene group having 2 or 3 carbon atoms include an ethylidene group and a propylidene group.

Among these, a single bond or an alkylidene group having 2 or 3 carbon atoms is preferred in view of easy availability of a benzyl bromide derivative used as a raw material component constituting the structural part, and an alkylidene group having 2 or 3 carbon atoms is particularly preferred in view of safety of a decomposed product after light irradiation.

Further specific examples of the novel compound of the present invention represented by the general formula 1 described in detail above include compounds M1 to M86 shown in Table 1 to Table 12 below.

TABLE 1
| Exemplary compound | *—Y₂—* | *—Y₃—* | 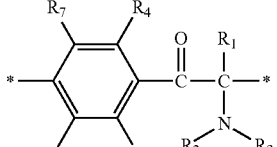 |
|---|---|---|---|
| M1 | 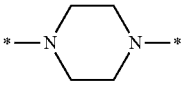 | Single bond | 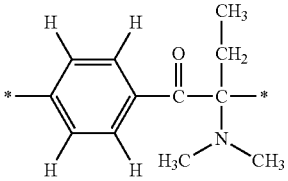 |
| M2 |  | Single bond | 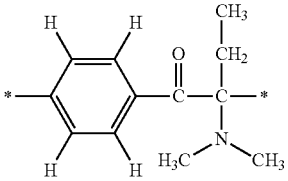 |
| M3 | 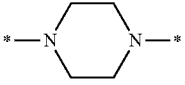 | Single bond | 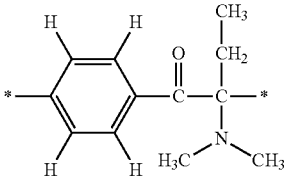 |
| M4 | 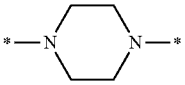 | Single bond | 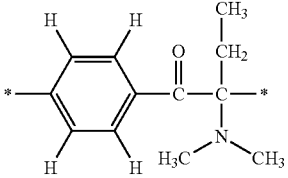 |
| M5 | 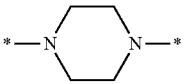 | Single bond | 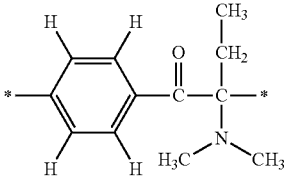 |
| M6 |  | Single bond | 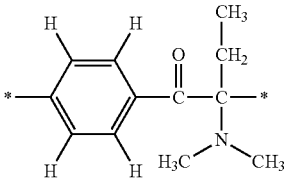 |
| M7 | 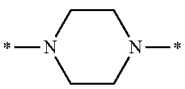 | Single bond | 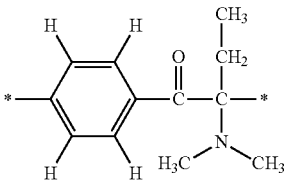 |

TABLE 1-continued

| Exemplary compound | $*-N-X_1-N-*$ with $X_3\cdots X_2$ | $Y_1-*$ |
|---|---|---|
| M1 | piperazine | 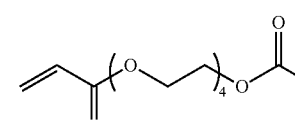 acrylate-(OCH₂CH₂)₄-O-C(=O)-CH₂CH₂-* |
| M2 | piperazine | 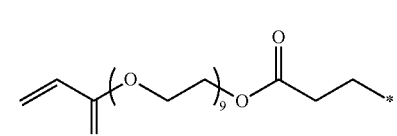 acrylate-(OCH₂CH₂)₉-O-C(=O)-CH₂CH₂-* |
| M3 | piperazine | 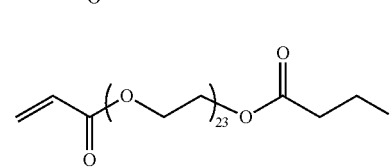 acrylate-(OCH₂CH₂)₂₃-O-C(=O)-CH₂CH₂-* |
| M4 | piperazine |  acrylate-O-(CH₂)₄-O-C(=O)-CH₂CH₂-* |
| M5 | piperazine | 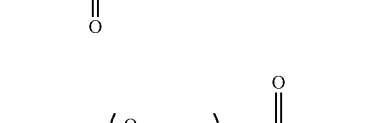 acrylate-(OCH(CH₃)CH₂)₃-O-C(=O)-CH₂CH₂-* |
| M6 | piperazine | 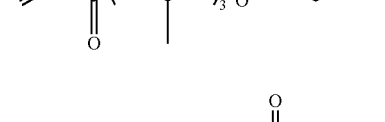 acrylate-O-(CH₂)₅-O-C(=O)-CH₂CH₂-* |
| M7 | piperazine | 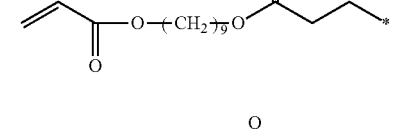 H₃C-(OCH₂CH₂)₃-O-C(=O)-CH₂CH₂-* |

TABLE 2

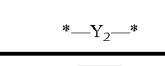

| Exemplary compound | *—Y₂—* | *—Y₃—* | structure with $R_2, R_3, R_4, R_5, R_6, R_7$ |
|---|---|---|---|
| M8 | piperazine 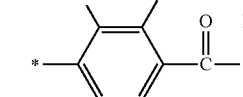 | Single bond | 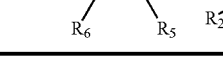 |

TABLE 2-continued
| | | | |
|---|---|---|---|
| M9 |  | Single bond | 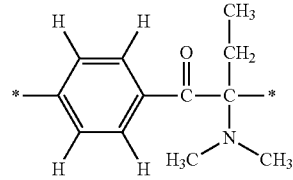 |
| M10 | 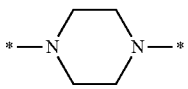 | Single bond | 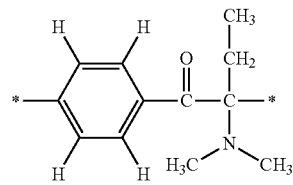 |
| M11 |  | *—CH$_2$—* | 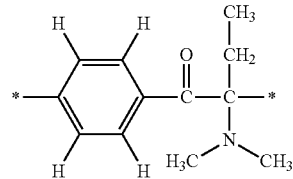 |
| M12 | 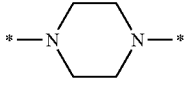 | *—CH$_2$—* | 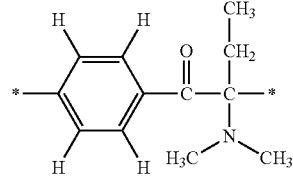 |
| M13 | 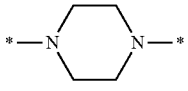 | *—CH$_2$—* | 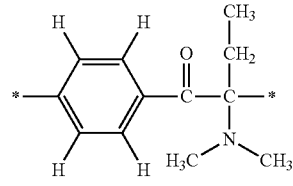 |
| M14 | 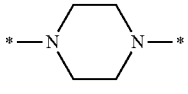 | 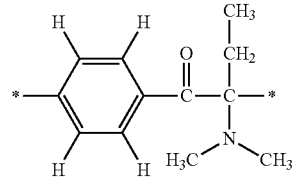 |  |
| Exemplary compound | $\overset{X_3\text{------}X_2}{*-N-X_1-N-*}$ | $Y_1-*$ |
|---|---|---|
| M8 | 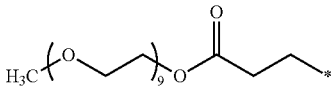 | 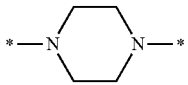 |
| M9 | 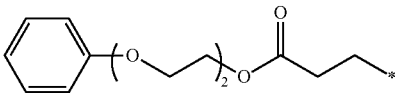 | 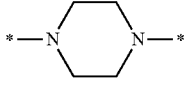 |
| M10 | 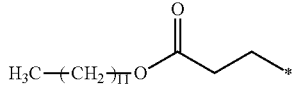 | |

TABLE 2-continued
| | *—Y₂—* | *—Y₃—* |
|---|---|---|
| M11 | 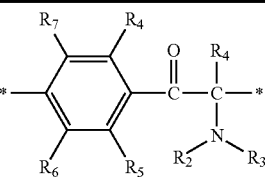 |  |
| M12 |  | 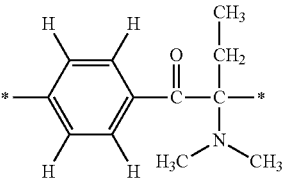 |
| M13 |  |  |
| M14 | 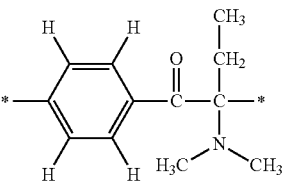 | 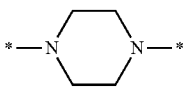 |
TABLE 3
| Exemplary compound | *—Y₂—* | *—Y₃—* |  |
|---|---|---|---|
| M15 | 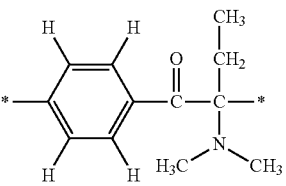 | $\begin{array}{c}CH_3\\|\\*-CH-*\end{array}$ | 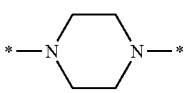 |
| M16 |  | $\begin{array}{c}CH_3\\|\\*-CH-*\end{array}$ | 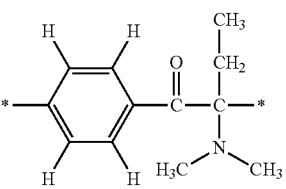 |
| M17 | *—N⌒N—* | $\begin{array}{c}CH_3\\|\\*-C-*\\|\\CH_3\end{array}$ | (structure) |
| M18 | *—N⌒N—* | $\begin{array}{c}CH_3\\|\\*-C-*\\|\\CH_3\end{array}$ | (structure) |

TABLE 3-continued

| Exemplary compound | *—N⏜X₁⏜N—* (with X₃----X₂) | | |
|---|---|---|---|
| M19 | *—N(piperazine)N—* | *—CH(CH₃)—* | phenyl-C(=O)-C(CH₃)(CH₂CH₃)-N(CH₃)₂—* |
| M20 | *—N(piperazine)N—* | *—CH₂—CH₂—* | phenyl-C(=O)-C(CH₃)(CH₂CH₃)-N(CH₃)₂—* |
| M21 | *—N(piperazine)N—* | *—CH₂—CH₂—* | phenyl-C(=O)-C(CH₃)(CH₂CH₃)-N(CH₃)₂—* |

| Exemplary compound | *—N—X₁—N—* (X₃----X₂) | $Y_1$—* |
|---|---|---|
| M15 | *—N(piperazine)N—* | CH₂=CH-C(=O)-(O-CH₂CH₂)₉-O-C(=O)-CH₂CH₂—* |
| M16 | *—N(piperazine)N—* | H₃C-(O-CH₂CH₂)₃-O-C(=O)-CH₂CH₂—* |
| M17 | *—N(piperazine)N—* | CH₂=CH-C(=O)-(O-CH₂CH₂)₄-O-C(=O)-CH₂CH₂—* |
| M18 | *—N(piperazine)N—* | CH₂=CH-C(=O)-(O-CH₂CH₂)₉-O-C(=O)-CH₂CH₂—* |
| M19 | *—N(piperazine)N—* | H₃C-(O-CH₂CH₂)₃-O-C(=O)-CH₂CH₂—* |
| M20 | *—N(piperazine)N—* | CH₂=CH-C(=O)-(O-CH₂CH₂)₄-O-C(=O)-CH₂CH₂—* |
| M21 | *—N(piperazine)N—* | CH₂=CH-C(=O)-(O-CH₂CH₂)₉-O-C(=O)-CH₂CH₂—* |

TABLE 4
| Exemplary compound | *—Y₂—* | *—Y₃—* | 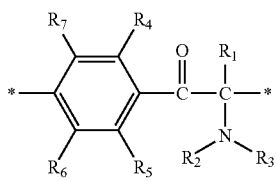 |
|---|---|---|---|
| M22 | 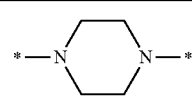 | —CH₂—CH₂—* | 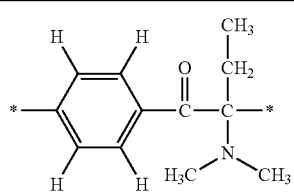 |
| M23 | 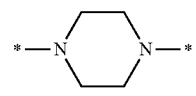 | Single bond | 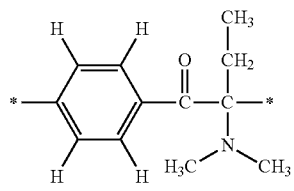 |
| M24 | 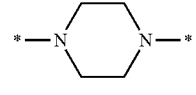 | Single bond | 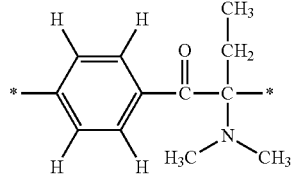 |
| M25 | 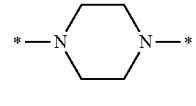 | Single bond | 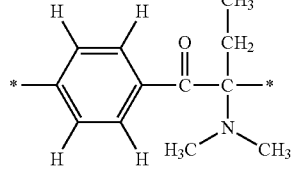 |
| M26 | 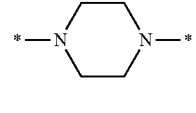 | Single bond | 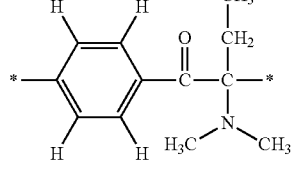 |
| M27 | 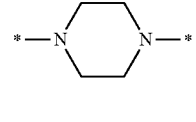 | 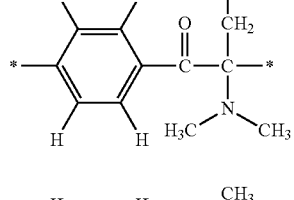 | 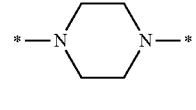 |
| M28 | 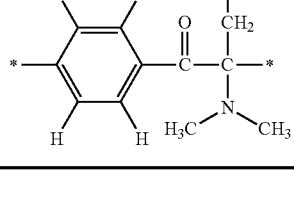 | Single bond | |

TABLE 4-continued

| Exemplary compound | $\underset{*-N-X_1-N-*}{X_3------X_2}$ | $Y_1-*$ |
|---|---|---|
| M22 | *—N⌒N—* (piperazine) | $H_3C{\left(O{\displaystyle \smile}\right)}_3 O{\displaystyle \smile}\underset{O}{\overset{\parallel}{C}}{\displaystyle \smile}*$ |
| M23 | *—N⌒N—* (piperazine) | $H_3C{-\!\!\!\!(}CH_2{)\!\!\!\!-}_{11}*$ |
| M24 | *—N⌒N—* (piperazine) | $H_3C{-\!\!\!\!(}CH_2{)\!\!\!\!-}_{5}*$ |
| M25 | *—N⌒N—* (piperazine) | benzyl (C₆H₅–CH₂–*) |
| M26 | *—N⌒N—* (piperazine) | $H{\left(O{\displaystyle \smile}\right)}_3*$ |
| M27 | *—N⌒N—* (piperazine) | $H{\left(O{\displaystyle \smile\smile}\right)}_3*$ |
| M28 | *—N⌒N—* (piperazine) | $C_6H_5{-}O{\left({\smile}O\right)}_5{\smile}\underset{OH}{\overset{|}{C}H}{\smile}*$ |

TABLE 5

| Exemplary compound | *—Y₂—* | *—Y₃—* | ![structure with R₁–R₇, phenyl ring with R₄,R₅,R₆,R₇, C=O, C with R₁ and NR₂R₃] |
|---|---|---|---|
| M29 | *—N⌒N—* (piperazine) | $*{-}\underset{CH_3}{\overset{\,}{C}H}{-}*$ | phenyl–C(=O)–C(CH₃)(CH₂–N(CH₃)₂)–* (aromatic H's at R₄–R₇) |
| M30 | *—N⌒N—* (piperazine) | Single bond | phenyl–C(=O)–C(CH₃)(CH₂–N(CH₃)₂)–* (aromatic H's at R₄–R₇) |

TABLE 5-continued
| | | | |
|---|---|---|---|
| M31 | 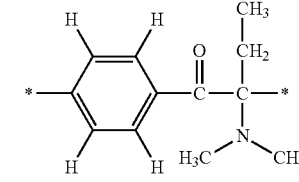 | Single bond | 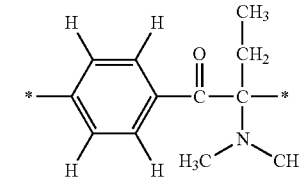 |
| M32 | 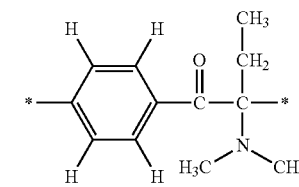 | $*-\underset{\underset{*}{|}}{\overset{CH_3}{|}}CH-*$ | 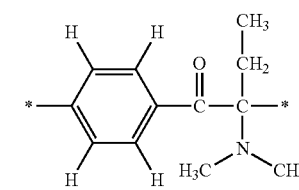 |
| M33 | 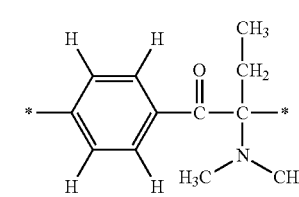 | *—CH$_2$—* | 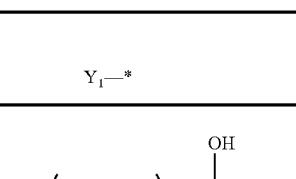 |
| M34 | 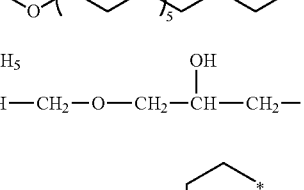 | *—CH$_2$—CH$_2$—* | 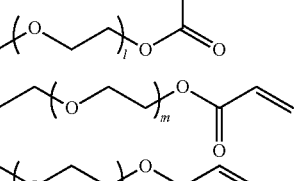 |
| M35 | | Single bond | |
| Exemplary compound | $\overset{X_3\text{-----}X_2}{*-\underset{|}{N}-X_1-\underset{|}{N}-*}$ | $Y_1-*$ |
|---|---|---|
| M29 | | |
| M30 | | |
| M31 | | |
$l + m + n = -3$ TABLE 5-continued
M32
 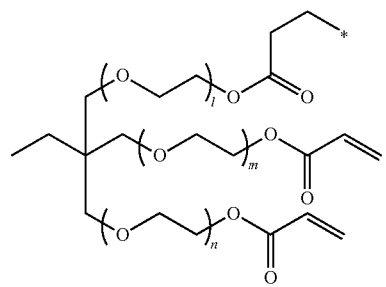
$l + m + n = \sim 3$
M33
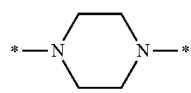 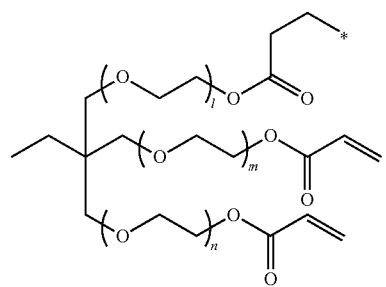
$l + m + n = \sim 3$
M34
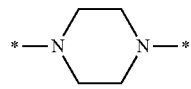 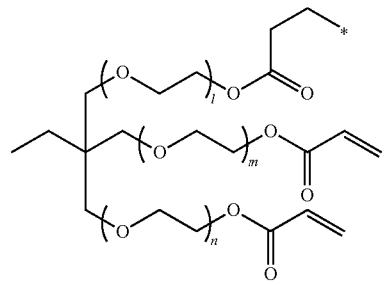
$l + m + n = \sim 3$
M35
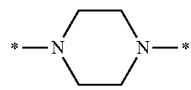 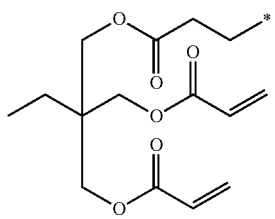

TABLE 6

| Exemplary compound | *—Y₂—* | *—Y₃—* | (structure with R₁–R₇) |
|---|---|---|---|
| M36 | piperazine | *—CH(CH₃)—* | phenyl-C(=O)-C(CH₃)(CH₂CH₃)-* with N(CH₃)₂ |
| M37 | piperazine | Single bond | phenyl-C(=O)-C(CH₃)(CH₂CH₃)-* with N(CH₃)₂ |
| M38 | piperazine | *—CH(CH₃)—* | phenyl-C(=O)-C(CH₃)(CH₂CH₃)-* with N(CH₃)₂ |
| M39 | piperazine | Single bond | phenyl-C(=O)-C(CH₃)(CH₂CH₃)-* with N(CH₃)₂ |
| M40 | piperazine | *—CH(CH₃)—* | phenyl-C(=O)-C(CH₃)(CH₂CH₃)-* with N(CH₃)₂ |
| M41 | piperazine | Single bond | phenyl-C(=O)-C(CH₃)(CH₂CH₃)-* with N(CH₃)₂ |
| M42 | piperazine | Single bond | phenyl-C(=O)-C(CH₃)(CH₂CH₃)-* with N(CH₃)₂ |

TABLE 6-continued

| Exemplary compound | *—N—X₁—N—* with X₃---X₂ | Y₁—* |
|---|---|---|
| M36 | piperazine | pentaerythritol-like triacrylate with ethyl branch |
| M37 | piperazine | ethoxylated pentaerythritol tetraacrylate, l + m + n + p = −4 |
| M38 | piperazine | ethoxylated pentaerythritol tetraacrylate, l + m + n + p = −4 |
| M39 | piperazine | pentaerythritol triacrylate |
| M40 | piperazine | pentaerythritol triacrylate |
| M41 | 2,5-dimethylpiperazine | PEG-diacrylate, n = 4 |

TABLE 6-continued

| Exemplary compound | Structure |
|---|---|
| M42 | *—N(CH₃)—CH₂CH₂—N(CH₃)—*  ;  CH₂=CH—C(=O)—O—(CH₂CH₂O)₄—C(=O)—CH₂CH₂—* |

TABLE 7

Common structure for the right column:

a phenyl ring bearing substituents R₄, R₅, R₆, R₇ linked through C(=O)—C(R₁)(NR₂R₃)—*

| Exemplary compound | *—Y₂—* | *—Y₃—* | Structure |
|---|---|---|---|
| M43 | piperazine-1,4-diyl | Single bond | phenyl(H,H,H,H)—C(=O)—C(CH₃)(CH₂—)(N(CH₃)(—(CH₂)₁₁CH₃))—* |
| M44 | 2,5-dimethylpiperazine-1,4-diyl | Single bond | phenyl(H,H,H,H)—C(=O)—C(CH₃)(CH₂—)(N(CH₃)₂)—* |
| M45 | 2,5-dimethylpiperazine-1,4-diyl | *—CH(CH₃)—* | phenyl(H,H,H,H)—C(=O)—C(CH₃)(CH₂—)(N(CH₃)₂)—* |
| M46 | 2,6-dimethylpiperazine-1,4-diyl | *—CH(CH₃)—* | phenyl(H,H,H,H)—C(=O)—C(CH₃)(CH₂—)(N(CH₃)₂)—* |
| M47 | *—N(piperidin-4-yl)—(CH₂)₃—(piperidin-4-yl)N—* | *—CH(CH₃)—* | phenyl(H,H,H,H)—C(=O)—C(CH₃)(CH₂—)(N(CH₃)₂)—* |
| M48 | *—NH—(CH₂)₂—O—(CH₂CH₂O)₂—(CH₂)₂—NH—* | Single bond | phenyl(H,H,H,H)—C(=O)—C(CH₃)(CH₂—)(N(CH₃)₂)—* |

TABLE 7-continued

| | | | |
|---|---|---|---|
| M49 | *—NH—(CH₂)₂—O—(CH₂CH₂O)₂—(CH₂)₂—NH—* | Single bond | (structure: phenyl-C(=O)-C(CH₃)(CH₂-)(N(CH₃)₂)) |

| Exemplary compound | *—N—X₁—N—* with X₃------X₂ | Y₁—* |
|---|---|---|
| M43 | *—N(piperazine)N—* | acrylate-O-(CH₂CH₂O)₄-C(=O)-CH₂CH₂-* |
| M44 | *—N(piperazine)N—* | acrylate-O-(CH₂CH₂O)₄-C(=O)-CH₂CH₂-* |
| M45 | *—N(piperazine)N—* | trimethylolpropane tri(ethoxylate) triacrylate structure; $l + m + n = -3$ |
| M46 | *—N(piperazine)N—* | trimethylolpropane tri(ethoxylate) triacrylate structure; $l + m + n = -3$ |
| M47 | *—N(piperazine)N—* | trimethylolpropane tri(ethoxylate) triacrylate structure; $l + m + n = -3$ |

TABLE 7-continued
| | | |
|---|---|---|
| M48 | 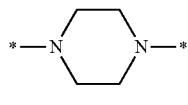 | 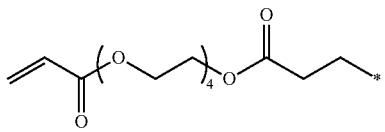 |
| M49 | 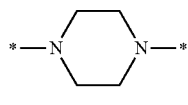 | 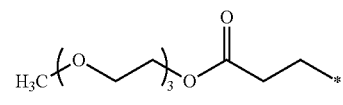 |
TABLE 8
| Exemplary compound | *—Y$_2$—* | *—Y$_3$—* | 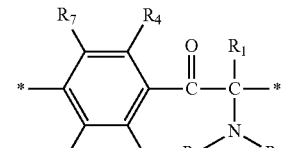 |
|---|---|---|---|
| M50 | 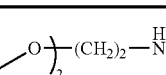 | Single bond | 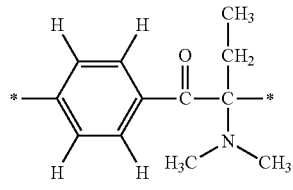 |
| M51 | 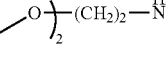 | 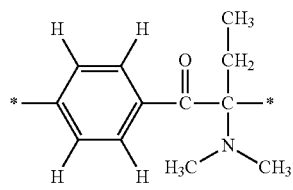 | 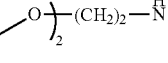 |
| M52 | 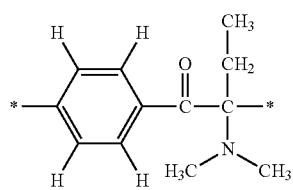 | 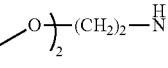 | 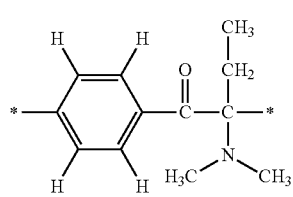 |
| M53 | 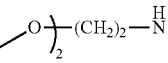 | Single bond | 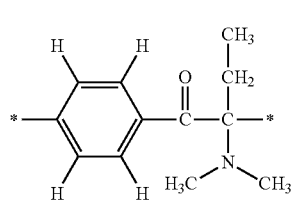 |
| M54 |  | Single bond |  |

TABLE 8-continued

| Exemplary compound | *—N—X₁—N—* with X₃----X₂ | Y₁—* |
|---|---|---|
| M55 | *—NH—(CH₂)₆—NH—* | *—CH(CH₃)—* linked to 4-(2-(dimethylamino)-2-methyl-1-oxobutyl)phenyl group |
| M55 | *—NH—(CH₂)₆—NH—* | Single bond to 4-(2-(dimethylamino)-2-methyl-1-oxobutyl)phenyl group |
| M56 | *—NH—(1,3-C₆H₄)—NH—* | Single bond to 4-(2-(dimethylamino)-2-methyl-1-oxobutyl)phenyl group |
| M50 | piperazine-1,4-diyl | CH₂=CH—C(=O)—O—(CH₂)₄—O—C(=O)—CH₂CH₂—* |
| M51 | piperazine-1,4-diyl | CH₂=CH—C(=O)—(O—CH₂CH₂)₄—O—C(=O)—CH₂CH₂—* |
| M52 | piperazine-1,4-diyl | H₃C—(O—CH₂CH₂)₃—O—C(=O)—CH₂CH₂—* |
| M53 | piperazine-1,4-diyl | CH₂=CH—C(=O)—(O—CH₂CH₂)₄—O—C(=O)—CH₂CH₂—* |
| M54 | piperazine-1,4-diyl | C₆H₅—(O—CH₂CH₂)₂—O—C(=O)—CH₂CH₂—* |
| M55 | piperazine-1,4-diyl | CH₂=CH—C(=O)—(O—CH₂CH₂)₄—O—C(=O)—CH₂CH₂—* |

TABLE 8-continued

| | | |
|---|---|---|
| M55 | piperazine | pentaerythritol-based triacrylate with PEG chains, $l+m+n=\sim3$ |
| M56 | piperazine | acrylate-$(OCH_2CH_2)_4$-O-C(O)-CH_2CH_2-* |

TABLE 9

| Exemplary compound | *—$Y_2$—* | *—$Y_3$—* | photoinitiator group (with $R_1$–$R_7$) |
|---|---|---|---|
| M57 | *—NH—(1,3-C$_6$H$_4$)—NH—* | Single bond | 4-substituted phenyl C(O)C(CH$_3$)(CH$_2$CH$_3$)N(CH$_3$)$_2$ |
| M58 | *—NH—(1,4-C$_6$H$_4$)—NH—* | Single bond | 4-substituted phenyl C(O)C(CH$_3$)(CH$_2$CH$_3$)N(CH$_3$)$_2$ |
| M59 | *—NH—(1,4-C$_6$H$_4$)—NH—* | Single bond | 4-substituted phenyl C(O)C(CH$_3$)(CH$_2$CH$_3$)N(CH$_3$)$_2$ |
| M60 | *—NHCH$_2$—(4-CH$_3$-1,3-C$_6$H$_3$)—CH$_2$NH—* | Single bond | 4-substituted phenyl C(O)C(CH$_3$)(CH$_2$CH$_3$)N(CH$_3$)$_2$ |

TABLE 9-continued

| Exemplary compound | *—NH—X—NH—* (diamine) | linker | Y₁—* |
|---|---|---|---|
| M61 | *—NH—CH₂—(1,3-phenylene)—CH₂—NH—* | Single bond | 4-(2-(dimethylamino)-2-methyl-1-oxobutyl)phenyl group (with CH₃, CH₂, C=O, N(CH₃)₂ substituents) |
| M62 | *—NH—CH₂—(1,3-phenylene)—CH₂—NH—* | Single bond | same aroyl-aminoketone group as M61 |
| M63 | *—NH—CH₂—(1,3-phenylene)—CH₂—NH—* | Single bond | same aroyl-aminoketone group as M61 |

| Exemplary compound | $\begin{array}{c} X_3\text{------}X_2 \\ *-N-X_1-N-* \end{array}$ | Y₁—* |
|---|---|---|
| M57 | *—N(piperazine)N—* | $H_3C-(O-CH_2CH_2)_3-O-C(=O)-CH_2CH_2-*$ |
| M58 | *—N(piperazine)N—* | $CH_2=CH-C(=O)-(O-CH_2CH_2)_4-O-C(=O)-CH_2CH_2-*$ |
| M59 | *—N(piperazine)N—* | $H_3C-(O-CH_2CH_2)_3-O-C(=O)-CH_2CH_2-*$ |
| M60 | *—N(piperazine)N—* | $CH_2=CH-C(=O)-(O-CH_2CH_2)_4-O-C(=O)-CH_2CH_2-*$ |
| M61 | *—N(piperazine)N—* | $CH_2=CH-C(=O)-(O-CH_2CH_2)_4-O-C(=O)-CH_2CH_2-*$ |
| M62 | *—N(piperazine)N—* | $H_3C-(O-CH_2CH_2)_3-O-C(=O)-CH_2CH_2-*$ |
| M63 | *—N(piperazine)N—* | $CH_2=CH-C(=O)-O-(CH_2)_4-O-C(=O)-CH_2CH_2-*$ |

TABLE 10

| Exemplary compound | *—Y₂—* | *—Y₃—* | ![structure with R₁-R₇] |
|---|---|---|---|
| M64 | *—NH—CH₂—(m-C₆H₄)—CH₂—NH—* | *—CH(CH₃)—* | phenyl-C(=O)-C(CH₃)(CH₂)-N(CH₃)₂ |
| M65 | *—N(H)—CH₂—(m-C₆H₄)—CH₂—N(H)—* | *—CH(CH₃)—* | phenyl-C(=O)-C(CH₂)-N(CH₃)₂ |
| M66 | *—NH—(p-C₆H₄)—O—(p-C₆H₄)—NH—* | Single bond | phenyl-C(=O)-C(CH₂)-N(CH₃)₂ |
| M67 | *—N(H)—(p-C₆H₄)—O—(p-C₆H₄)—N(H)—* | Single bond | phenyl-C(=O)-C(CH₂)-N(CH₃)₂ |
| M68 | *—NH—(p-C₆H₄)—C(=O)—(p-C₆H₄)—NH—* | Single bond | phenyl-C(=O)-C(CH₂)-N(CH₃)₂ |
| M69 | *—N(H)—(p-C₆H₄)—C(=O)—(p-C₆H₄)—N(H)—* | Single bond | phenyl-C(=O)-C(CH₂)-N(CH₃)₂ |
| M70 | *—N(CH₃)—(p-C₆H₄)—C(=O)—(p-C₆H₄)—N(CH₃)—* | Single bond | phenyl-C(=O)-C(CH₂)-N(CH₃)₂ |

TABLE 10-continued

| Exemplary compound | $*-N-X_1-N-*$ with $X_3\cdots X_2$ | $Y_1-*$ |
|---|---|---|
| M64 | *—N(piperazine)N—* | CH$_2$=CH–C(=O)–(O–CH$_2$CH$_2$)$_4$–O–C(=O)–CH$_2$CH$_2$–* |
| M65 | *—N(piperazine)N—* | H$_3$C–(O–CH$_2$CH$_2$)$_3$–O–C(=O)–CH$_2$CH$_2$–* |
| M66 | *—N(piperazine)N—* | CH$_2$=CH–C(=O)–(O–CH$_2$CH$_2$)$_4$–O–C(=O)–CH$_2$CH$_2$–* |
| M67 | *—N(piperazine)N—* | H$_3$C–(O–CH$_2$CH$_2$)$_3$–O–C(=O)–CH$_2$CH$_2$–* |
| M68 | *—N(piperazine)N—* | CH$_2$=CH–C(=O)–(O–CH$_2$CH$_2$)$_4$–O–C(=O)–CH$_2$CH$_2$–* |
| M69 | *—N(piperazine)N—* | H$_3$C–(O–CH$_2$CH$_2$)$_3$–O–C(=O)–CH$_2$CH$_2$–* |
| M70 | *—N(piperazine)N—* | CH$_2$=CH–C(=O)–(O–CH$_2$CH$_2$)$_4$–O–C(=O)–CH$_2$CH$_2$–* |

TABLE 11

| Exemplary compound | *—Y$_2$—* | *—Y$_3$—* | (benzoyl-amino structure with R$_1$–R$_7$) |
|---|---|---|---|
| M71 | 4,4'-bis(methylamino)benzophenone linker: *—N(CH$_3$)—C$_6$H$_4$—C(=O)—C$_6$H$_4$—N(CH$_3$)—* | Single bond | 4-(2-(dimethylamino)-2-methylpropanoyl)phenyl group |
| M72 | 3,3'-bis(amino)benzophenone linker: *—NH—C$_6$H$_4$—C(=O)—C$_6$H$_4$—NH—* | Single bond | 4-(2-(dimethylamino)-2-methylpropanoyl)phenyl group |

TABLE 11-continued

| Exemplary compound | (structure) | | (structure) |
|---|---|---|---|
| M73 | *—NH—(3-C₆H₄)—C(=O)—(3-C₆H₄)—NH—* | Single bond | *—C₆H₄—C(=O)—C(CH₃)(CH₂CH₃)(N(CH₃)₂)—* |
| M74 | *—NH—(4-C₆H₄)—CH₂—(4-C₆H₄)—NH—* | Single bond | *—C₆H₄—C(=O)—C(CH₃)(CH₂CH₃)(N(CH₃)₂)—* |
| M75 | *—NH—(4-C₆H₄)—CH₂—(4-C₆H₄)—NH—* | Single bond | *—C₆H₄—C(=O)—C(CH₃)(CH₂CH₃)(N(CH₃)₂)—* |
| M76 | *—NH—(4-C₆H₄)—SO₂—(4-C₆H₄)—NH—* | Single bond | *—C₆H₄—C(=O)—C(CH₃)(CH₂CH₃)(N(CH₃)₂)—* |
| M77 | *—NH—(4-C₆H₄)—SO₂—(4-C₆H₄)—NH—* | Single bond | *—C₆H₄—C(=O)—C(CH₃)(CH₂CH₃)(N(CH₃)₂)—* |

| Exemplary compound | $*-N-X_1-N-*$ with $X_3\cdots X_2$ | $Y_1-*$ |
|---|---|---|
| M71 | piperazine | $H_3C-(O-CH_2CH_2)_3-O-C(=O)-CH_2CH_2-*$ |
| M72 | piperazine | $CH_2=CH-C(=O)-(O-CH_2CH_2)_4-O-C(=O)-CH_2CH_2-*$ |
| M73 | piperazine | $H_3C-(O-CH_2CH_2)_3-O-C(=O)-CH_2CH_2-*$ |
| M74 | piperazine | $CH_2=CH-C(=O)-(O-CH_2CH_2)_4-O-C(=O)-CH_2CH_2-*$ |
| M75 | piperazine | $H_3C-(O-CH_2CH_2)_3-O-C(=O)-CH_2CH_2-*$ |

TABLE 11-continued
| | | |
|---|---|---|
| M76 | 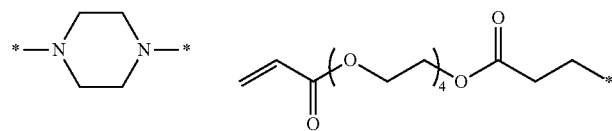 | |
| M77 | 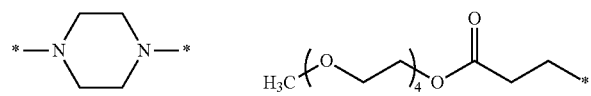 | |
TABLE 12
| Exemplary compound | *—Y$_2$—* | *—Y$_3$—* | (structure with R$_1$–R$_7$) |
|---|---|---|---|
| M78 | *—O—(CH$_2$—CH$_2$—O)$_4$—* | Single bond | |
| M79 | *—O—(CH(CH$_3$)—CH$_2$—O)$_3$—* | Single bond | |
| M80 | *—O—(CH$_2$—CH$_2$—CH$_2$—CH$_2$—O)$_{11}$—* | Single bond | |
| M81 | *—O—(CH$_2$)$_6$—O—* | Single bond | |
| M82 | *—O—CH$_2$—C$_6$H$_4$—CH$_2$—O—* | Single bond | |

TABLE 12-continued
| | | | |
|---|---|---|---|
| M83 |  | Single bond | 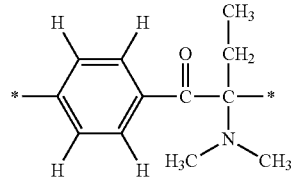 |
| M84 | 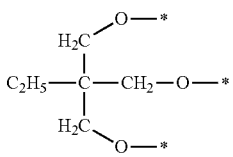 | Single bond | 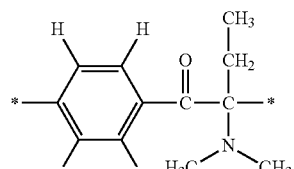 |
| M85 | 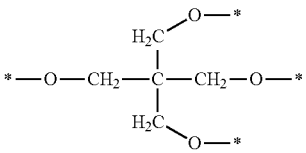 | Single bond | 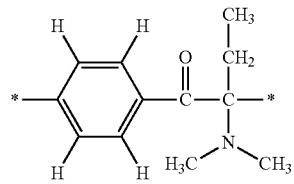 |
| M86 |  | Single bond | 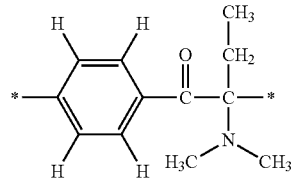 |
| Exemplary compound | $\overset{X_3\text{------}X_2}{*-N-X_1-N-*}$ | $Y_1-*$ |
|---|---|---|
| M78 | 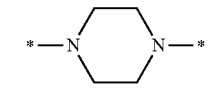 | 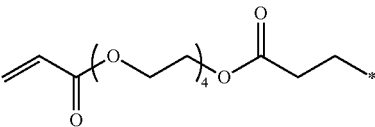 |
| M79 |  | 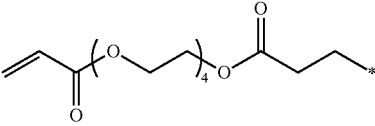 |
| M80 | 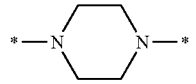 | 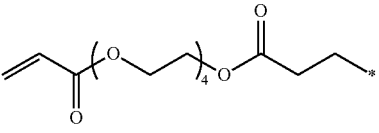 |
| M81 |  | 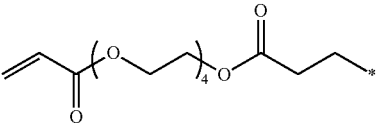 |
| M82 | 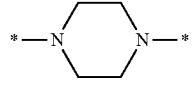 | 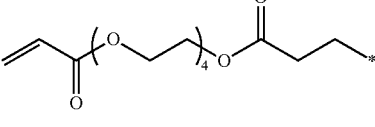 |

TABLE 12-continued

| | | |
|---|---|---|
| M83 | *—N⌐⌐N—* (piperazine) | acrylate-O-(CH2CH2O)4-C(=O)-CH2CH2-* |
| M84 | *—N⌐⌐N—* (piperazine) | acrylate-O-(CH2CH2O)4-C(=O)-CH2CH2-* |
| M85 | *—N⌐⌐N—* (piperazine) | acrylate-O-(CH2CH2O)4-C(=O)-CH2CH2-* |
| M86 | *—N⌐⌐N—* (piperazine) | H3C—(CH2)17—N(C(=O)-*) |

Among the compounds M1 to M86 described above, the compounds M1, M4, M7, M14, M23, M28, M31, M32, M41, M43, M45, M50, M55, M64, and M7.8 are particularly preferred in view of a good balance between light curability and low migration and easy availability of raw materials.

The novel compound of the present invention represented by the general formula 1 described above can be industrially produced through [Step I] to [Step VI] described below.

[Step I]

Halogenated benzene is reacted with an acid halide compound having a halide atom at the α-position to synthesize an alkyl acetophenone derivative having a halogen atom at the α-carbon atom of carbonyl. The reaction in [Step I] can be performed by Friedel-Crafts acylation reaction in the presence of anhydrous aluminum chloride.

Examples of the halogenated benzene include fluorobenzene, chlorobenzene, bromobenzene, and the like. Also, examples of the acid halide compound having a halide atom at the α-position include 2-bromopropionic acid bromide, 2-bromopropionic acid chloride, 2-bromovaleric acid bromide, 2-bromovaleric acid chloride, 2-bromohexanoic acid bromide, 2-bromooctanoic acid bromide, and the like.

[Step II]

Next, a secondary monoamine compound ($NH(R_2)(R_3)$) is reacted to convert the α-position into an amino group. Examples of the secondary monoamine compound ($NH(R_2)(R_3)$) include dimethylamine, diethylamine, methylbutylamine, methyloctylamine, methyldodecylamine, ethylhexylamine, diethanolamine, diisopropanolamine, diisobutanolamine, 2,2'-diethoxydiethylamine, 2,2'-dimethoxydiethylamine, morpholine, pyrrolidine, piperizine, N-methylpiperazine, 2,6-dimethylmorpholine, and the like. The reaction can be performed under the conditions of a temperature condition of 0° C. to 80° C. in the presence of a base, for example, a carbonate salt such as calcium carbonate, potassium carbonate, sodium carbonate, or the like, a tertiary amine such as triethylamine, diisopropylethylamine, or the like. When secondary amine is reacted as the base, production can be performed by using an excessive amount.

[Step III]

Next, benzyl bromide having as a substituent (—$Y_3$—C(=O)—OR) (wherein R is an alkyl group or a hydrogen atom) as a substituent on an aromatic nucleus is reacted with a tertiary amine of an acetophenone derivative, leading to a quaternary ammonium salt. Then, α-aminoacetophenone intermediate compound A (general formula 3) represented by general formula 3 is synthesized by 1,2-rearrangement reaction (Stevens rearrangement) through alkali treatment. The resultant α-aminoacetophenone intermediate compound (general formula 3) has a halogen atom on the aromatic ring of an acetophenone portion and has a carboxyl group on the aromatic ring of a benzyl group substituted at the α-position.

[Chem. 55]

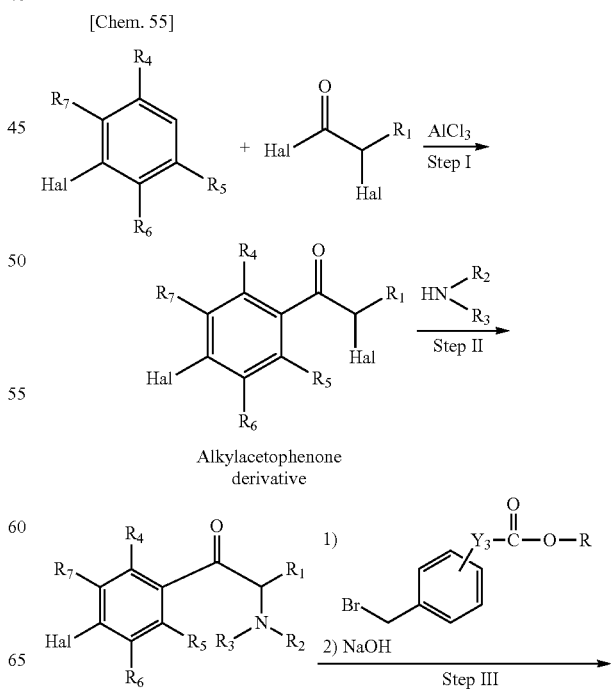

Alkylacetophenone derivative

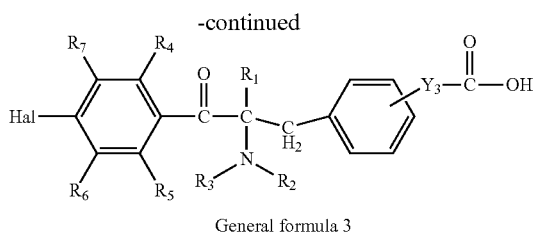

General formula 3

(In the reaction formula, "Hal" represents a halogen atom.)

As described above, $Y_3$ in benzyl bromide having a substituent (—$Y_3$—C(=O)—OR) as a substituent on an aromatic nucleus is a single bond, an alkylene group having 1 to 3 carbon atoms, or an alkylidene group having 2 or 3 carbon atoms, and a single bond, a methylene group, or an ethylidene group is preferred in view of easy availability of a raw material. R is preferably a hydrogen atom or an alkyl group such as a methyl group, an ethyl group, or the like. Therefore, examples of the benzyl bromide compound having a substituent (—$Y_3$—C(=O)—OR) (wherein R is a methyl group, an ethyl group, or a hydrogen atom) as a substituent on an aromatic nucleus include methyl bromomethylbenzoate, methyl 2-[4-(bromomethyl)phenyl]propionate, ethyl 2-[4-(bromomethyl)phenyl]acetate, and the like.

Also, the formation of quaternary ammonium in [Step III] can be performed at 20° C. to 100° C., and subsequent 1,2-rearrangment reaction (Stevens rearrangement) can be performed by using an aqueous sodium hydroxide solution as the base at 20° C. to 80° C.

[Step IV]

Next, a carboxyl group of the α-aminoacetophenone intermediate compound (general formula 3) is condensationsented by the general formula 3 is converted to an acid chloride by using thionyl chloride or the like and is then reacted with the di- or higher functional amine, a method in which the α-aminoacetophenone intermediate compound represented by the general formula 3 is reacted with the di- or higher functional alcohol by using an active esterification agent such as dicyclohexyl carbodiimide (DCC) or the like, a method in which the α-aminoacetophenone intermediate compound represented by the general formula 3 is converted to a mixed acid anhydride by using acid anhydride such as acetic anhydride or the like and is then reacted with a di- or higher functional alcohol, and the like.

On the other hand, when the di- or higher functional alcohol is used as a compound represented by the general formula 4, examples of a method for synthesizing the intermediate compound B include a method in which a carboxyl group arranged on the aromatic ring of the intermediate compound represented by the general formula 3 is converted to an acid chloride by using thionyl chloride or the like and is then reacted with the di- or higher functional alcohol, a method in which the intermediate compound is reacted with the di- or higher functional alcohol by dehydration condensation using an acid catalyst such as para-toluenesulfonic acid or the like, a method in which the intermediate compound is reacted with the di- or higher functional alcohol by using an active esterification agent such as dicyclohexyl carbodiimide (DCC) or the like, a method in which the intermediate compound is converted to a mixed acid anhydride by using acid anhydride such as acetic anhydride or the like and is then reacted with the di- or higher functional alcohol, and the like.

[Chem. 56]

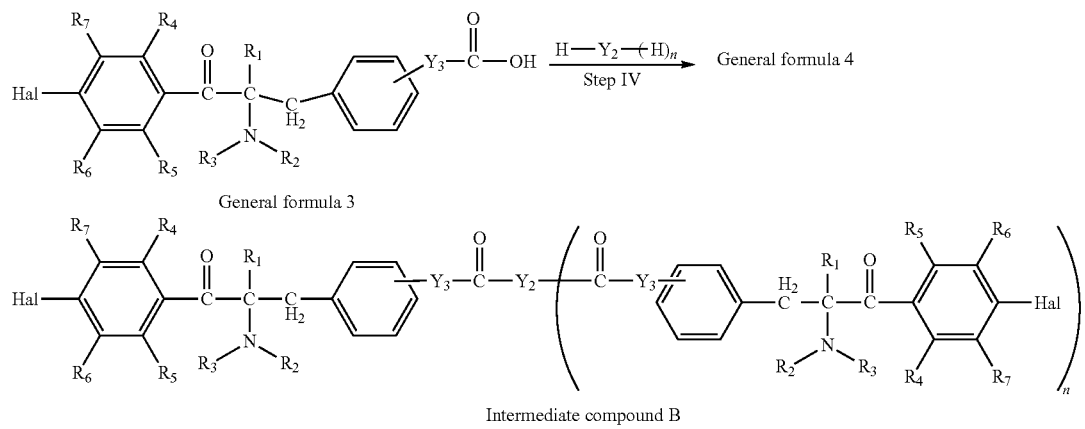

reacted with a di- or higher functional primary or secondary amine or di- or higher functional alcohol (general formula 4) to induce an intermediate compound B composed of a polyamide compound and a polyester compound.

For example, when difunctional diamine is used as a compound represented by the general formula 4, 2 moles of the α-aminoacetophenone intermediate compound (general formula 3) is reacted with 1 mole of the difunctional diamine, whereby the intermediate compound B having a molecular structure having two symmetrical amide groups can be synthesized. Examples of a method include a method in which a carboxyl group arranged on the aromatic ring of the α-aminoacetophenone intermediate compound repre- (In the reaction formula, "Hal" represents a halogen atom.)

Examples of the primary or secondary amine as the compound represented by the general formula 4 include alkylamines such as ethylenediamine, 1,3-diaminopropane, 1,2-diaminopropane, 1,4-diaminobutane, 1,2-diamino-2-methylpropane, 2-methyl-1,3-propanediamine, 1,5-diaminopentane, 2,2-dimethyl-1,3-propanediamine, 1,6-diaminohexane, 1,2-diaminocyclohexane, 1,3-diaminocyclohexane, 1,4-diaminocyclohexane, 2,2'-diamino-N-methyldiethylamine, 1,7-diaminoheptane, 1,3-bis(aminomethyl)cyclohexane, 1,4-bis(aminomethyl)cyclohexane, 1,8-diaminooctane, N-(3-aminopropyl)-N-methyl-1,3-propanediamine, 1,10-diaminododecane, 1,11- diaminoundecane, 1,12-diaminododecane, 1,18-diaminooctadecane, bis(4-aminocyclohexyl)methane, piperazine, 2-methylpiperazine, 2,5-dimethylpiperazine, 2,3-dimethylpiperazine, 2,5-diazabicyclo[2.2.1]heptane, homopiperazine, N,N'-dimethylethylenediamine, N,N'-ethylenediethyldiamine, N,N'-bis[2-(methylamino)ethyl]methylamine, 1,1-tris(aminomethyl)ethane, ethylidyne tris(methylamine), and the like; polyalkylene ether amines such as 2,2'-oxybis(ethylamine), 1,8-diamino-3,6-dioxaoctane, 3,6,9-trioxaundecane-1,11-diamine, 4,9-dioxa-1,12-dodecanediamine, 4,7,10-trioxa-1,13-tridecanediamine, 3,6,9,12-tetraoxatetradecane-1,14-diamine, and the like; aromatic diamines such as m-xylenediamine, p-xylenediamine, 1,3-phenylenediamine, 1,4-phenylenediamine, 1,5-diaminonaphthalene, 3,3'-dimethylbenzidine 3,3'-diethylbenzidine, 3,3'-dimethoxybenzidine, 3,3',5,5'-tetramethylbenzidine, 2,2'-dimethylbenzidine, 1,3,5-tris(4-aminophenyl)benzene, 2,7-diaminofluorene, 4,4'-diaminobenzophenone, 3,3'-diaminobenzophenone, 3,3'-diaminodiphenylmethane, 4,4'-ethylenedianiline, 1,1-bis(4-aminophenyl)cyclohexane 9,9-bis(4-aminophenyl)fluorene, 1,4-bis[2-(4-aminophenyl)-2-propyl]benzene, 2,2-bis(4-aminophenyl)hexafluoropropane, 4,4'-diaminodiphenylsulfone, 3,3'-diaminodiphenylsulfone, 1,4-bis(4-aminophenoxy)benzene, 1,3-bis(3-aminophenoxy)benzene, 1,3-bis(4-aminophenoxy)benzene, 2,2-bis[4-(4-aminophenoxy) phenyl]hexafluoropropane, 2,2-bis[4-(4-aminophenoxy)phenyl]propane, 4,4'-bis(4-aminophenoxy)biphenyl, bis[4-(4-aminophenoxy)phenyl]sulfone, 1,4-bis(4-amino-2-trifluoromethylphenoxy)benzene, and the like.

Examples of the di- or higher functional alcohol as the compound represented by the general formula 4 include linear alkylene diols such as ethylene glycol, diethylene glycol, 1,3-propanediol, 1,4-butanediol, 1,5-petanediol, 1,6-hexanediol, 1,7-heptanediol, 1,8-octanediol, 1,9-nonanediol, 1,10-decanediol, 1,12-dodecanediol, 1,14-tetradecanediol, 1,16-hexadecanediol, 1,18-octadecanediol, 1,20-icosanediol, and the like, and ethylene oxide-modified products and propylene oxide-modified products thereof; ether glycol such as polyoxyethylene glycol, polyoxypropylene glycol, and the like; modified polyether polyols produced by ring-opening polymerization of these linear alkylenediols and various cyclic ether bond-containing compounds such as ethylene oxide, propylene oxide, tetrahydrofuran, ethyl glycidyl ether, propyl glycidyl ether, butyl glycidyl ether, phenyl glycidyl ether, allyl glycidyl ether, and the like; difunctional hydroxyl group-containing compounds such as lactone-based polyester polyol and the like, which are produced by polycondensation reaction of the linear alkylenediols and various lactones such as s-caprolactone and the like; and tri- or higher functional polyols such as trimethylolethane, trimethylolpropane, 2,2,4-trimethyl-1,3-pentanediol, glycerin, hexanetriol, pentaerythritol, and ethylene oxide-modified products and propylene oxide-modified products thereof.

[Step V]

Then, an aryl halogen portion at a terminal portion of the molecule of the intermediate compound B is substituted by a difunctional cyclic amine represented by general formula 5, thereby synthesizing intermediate product C having a secondary amine at a terminal of its molecule.

[Chem. 57]

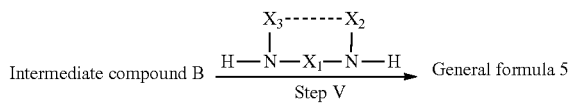

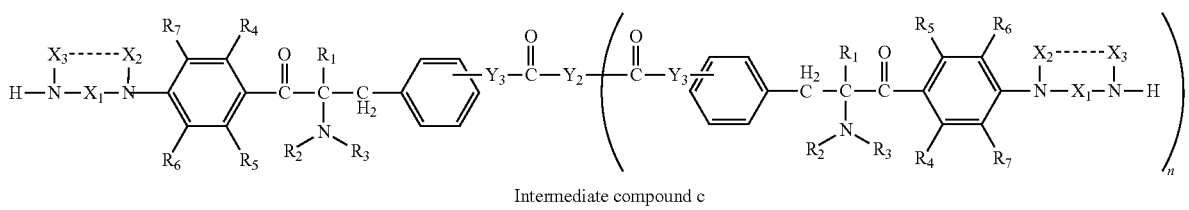

Intermediate compound c

The reaction can be performed under a temperature condition of 60° C. to 160° C. In this reaction, the difunctional cyclic amine represented by the general formula 5 can be excessively used or an inorganic carbonate salt such as potassium carbonate can be used as a scavenger for the acid generated in the system. Examples of the difunctional cyclic amine represented by the general formula 5 include piperazine, 2-methylpiperazine, 2,5-dimethylpiperazine, 2,3-dimethylpiperazine, 2,5-diazabicyclo[2.2.1]heptane, homopiperazine, and the like.

[Step VI]

Next, as a final reaction, the novel compound of the present invention represented by the general formula 1 can be produced by reacting the secondary amine located at a structural terminal of the intermediate compound C produced in [Step V] with a (meth)acrylic acid ester compound, isocyanuric acid ester, glycidyl ether, or alkyl halide. Specifically, [Step VI] can be classified into (Step VI-1) to (Step VI-9) below according to the compound reacted with the intermediate compound C.

(Step VI-1)

The secondary amine located at a structural terminal of the intermediate compound C is reacted with a halogenated alkane having 3 to 18 carbon atoms and represented by Hal-R' in a reaction formula below (the alkane may have a halogen atom or hydroxyl group not involved in the reaction), whereby a novel compound represented by general formula 1-1 below in which $Y_1$ is an alkyl group (y1-1) having 3 to 18 carbon atoms and having no substituent or having a halogen atom or a hydroxyl group as a substituent can be produced.

[Chem. 58]

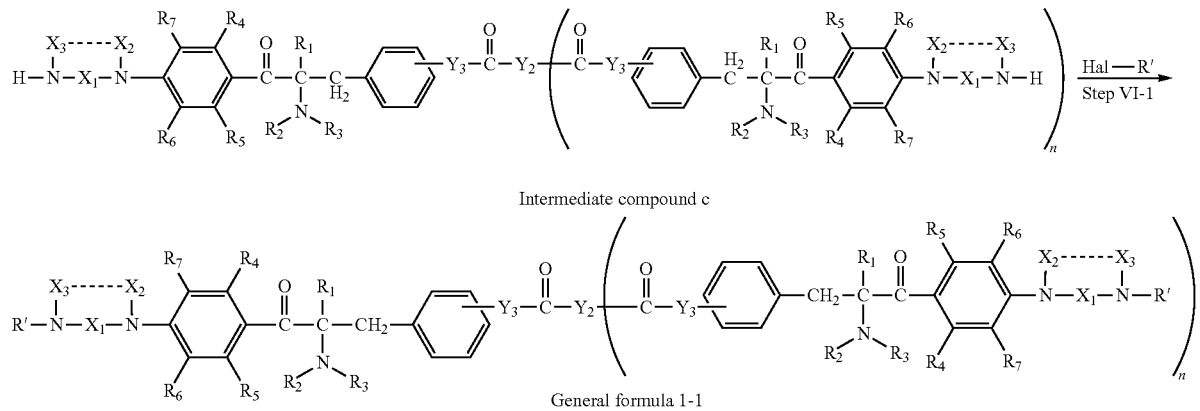

Intermediate compound c

General formula 1-1

(In the formula, Hal represents a halogen atom, and R' represents an alkyl group which may have a halogen atom or a hydroxyl group.)

Examples of the halogenated alkane having 3 to 18 carbon atoms and represented by Hal-R' include chloroalkanes such as 1-chloropropane, 2-chloropropane, 1-chlorobutane, 2-chlorobutane, 2-methyl-2-chloropropane, 2-methyl-1-chloropropane, 1-chloropentane, 2-chloropentane, 3-chloropentane, 2-chloro-2-methylbutane, 1-chloro-2-ethylbutane, 1-chlorohexane, 2-chlorohexane, 3-chlorohexane, 2-chloromethylpentane, 1-chloroheptane, 2-chloroheptane, 3-chloroheptane, 1-chlorooctane, 2-chlorooctane, 3-chlorooctane, 1-chloro-1,1,3,3-tetramethylbutane, 1-chloro-2,2,4,4-tetramethylbutane, 1-chloro-3-methylheptane, 1-chloro-2-ethylhexane, 1-chlorononane, 2-chlorononane, 3-chlorononane, 1-chloro-1,1,3-trimethylhexane, 1-chloro-1,1,3,3-tetramethylpentane, 1-chlorodecane, 2-chlorodecane, 3-chlorodecane, 1-chloro-1,1,3,3,5,5-hexamethylhexane, 1-chloro-8-methylnonane, 1-chloroundecane, 2-chloroundecane, 3-chloroundecane, 1-chlorododecane, 2-chlorododecane, 3-chlorododecane, 1-chlorotridecane, 2-chlorotridecane, 3-chlorotridecane, 1-chlorotetradecane, 2-chlorotetradecane, 3-chlorotetradecane, 1-chloropentadecane, 2-chloropentadecane, 3-chloropentadecane, 1-chlorohexadecane, 2-chlorohexadecane, 3-chlorohexadecane, 1-chloroheptadecane, 2-chloroheptadeane, 3-chloroheptadecane, 1-chlorooctadecane, 2-chlorooctadecane, 3-chlorooctadecane, and the like; bromoalkanes such as 1-bromopropane, 2-bromopropane, 1-bromobutane, 2-bromobutane, 2-methyl-2-bromopropane, 2-methyl-1-bromopropane, 1-bromopentane, 2-bromopentane, 3-bromopentane, 2-bromo-2-methylbutane, 1-bromo-2-ethylbutane, 1-bromohexane, 2-bromohexane, 3-bromohexane, 2-bromomethylpentane, 1-bromoheptane, 2-bromoheptane, 3-bromoheptane, 1-bromooctane, 2-bromooctane, 3-bromooctane, 1-bromo-1,1,3,3-tetramethylbutane, 1-bromo-2,2,4,4-tetramethylbutane, 1-bromo-3-methylheptane, 1-bromo-2-ethylhexane, 1-bromononane, 2-bromononane, 3-bromononane, 1-bromo-1,1,3-trimethylhexane, 1-bromo-1,1,3,3-tetramethylheptane, 1-bromodecane, 2-bromodecane, 3-bromodecane, 1-bromo-1,1,3,3,5,5-hexamethylhexane, 1-bromo-8-methylnonane, 1-bromoundecane, 2-bromoundecane, 3-bromoundecane, 1-bromododecane, 2-bromododecane, 3-bromododecane, 1-bromotridecane, 2-bromotridecane, 3-bromotridecane, 1-bromotetradecane, 2-bromotetradecane, 3-bromotetradecane, 1-bromopentadecane, 2-bromopentadecane, 3-bromopentadecane, 1-bromohexadecane, 2-bromohexadecane, 3-bromohexadecane, 1-bromoheptadecane, 2-bromoheptadecane, 3-bromoheptadecane, 1-bromooctadecane, 2-bromooctadecane, 3-bromooctadecane, and the like; idoalkanes such as 1-idopropane, 2-idopropane, 1-idobutane, 2-idobutane, 2-methyl-2-idopropane, 2-methyl-1-idopropane, 1-idopentane, 2-idopentane, 3-idopentane, 2-ido-2-methylbutane, 1-ido-2-ethylbutane, 1-idohexane, 2-idohexane, 3-idohexane, 2-idomethylpentane, 1-idoheptane, 2-idoheptane, 3-idoheptane, 1-idooctane, 2-idooctane, 3-idooctane, 1-ido-1,1,3,3-tetramethylbutane, 1-ido-2,2,4,4-tetramethylbutane, 1-ido-3-methylheptane, 1-ido-2-ethylhexane, 1-idononane, 2-idononane, 3-idononane, 1-ido-1,1,3-trimethylhexane, 1-ido-1,1,3,3-tetramethylpentane, 1-idodecane, 2-idodecane, 3-idodecane, 1-ido-1,1,3,3,5,5-hexamethylhexane, 1-ido-8-methylnonane, 1-idoundecane, 2-idoundecane, 3-idoundecane, 1-idododecane, 2-idododecane, 3-idododecane, 1-idotridecane, 2-idotridecane, 3-idotridecane, 1-idotetradecane, 2-idotetradecane, 3-idotetradecane, 1-idopentadecane, 2-idopentadecane, 3-idopentadecane, 1-idohexadecane, 2-idohexadecane, 3-idohexadecane, 1-idoheptadecane, 2-idoheptadecane, 3-idoheptadecane, 1-idooctadecane, 2-idooctadecane, 3-idooctadecane, and the like.

Also, when the halogenated alkane having 3 to 18 carbon atoms and represented by Hal-R' further has a halogen atom in the alkane structure, examples thereof include 1-bromo-3-fluoropropane, 1-bromo-3-chloropropane, 1-ido-3-fluoropropane, 1-ido-3-chloropropane, 1-bromo-2-fluoropropane, 1,1,1-trifluoro-3-idopropane, 1,1,1,2,2-pentafluoro-3-idopropane, 1-bromo-4-fluorobutane, 1-bromo-3-fluorobutane, 1-bromo-4-chlorobutane, 1,1,1-trifluoro-4-idobutane, 1,1,1,2,2,3,3-pentafluoro-4-idobtane, 1-bromo-5-fluoropentane, 1-ido-5-fluoropentane, 1,1,1,2,2-pentafluoro-5-idopentane, 1-bromo-6-fluorohexane, 1-ido-6-fluorohexane, 1,1,1-trichloro-6-idohexane, 1-bromo-7-fluoroheptane, 1-ido-7-fluoroheptane, 1-bromo-8-fluorooctane, 1-ido-8-fluorooctane, 1-bromo-9-fluorononane, 1-ido-9-fluorononane, 1-bromo-10-fluorodecane, 1-ido-10-fluorodecane, 1-bromo-12-fluorododecane, 1-ido-12-fluorododecane, 1-bromo-18-fluorooctadecane, 1-ido-18-fluorooctadecane, 1,1,1-trichloro-18-idooctadecane, and the like.

Further, when the halogenated alkane having 3 to 18 carbon atoms and represented by Hal-R' further has a hydroxyl group in the alkane structure, examples thereof include 3-bromo-1-propanol, 3-iodo-1-propanol, 4-iodo-2-methyl-2-butanol, 4-bromo-2-methyl-2-butanol, 1-iodo-2-methyl-2-propanol, 1-bromo-2-methyl-2-propanol, 1-iodo-4-butanol, 1-bromo-4-butanol, 1-iodo-2-butanol, 1-bromo-2-butanol, 5-iodo-1-pentanol, 5-bromo-1-pentanol, 1-iodo-6-hexanol, 1-bromo-6-hexanol, 5-iodo-3-methyl-1-pentanol, 5-bromo-3-methyl-1-pentanol, 1-iodo-8-octanol, 1-bromo-8-octanol, 1-iodo-12-dodecanol, 1-bromo-12-dodecanol, 1-iodo-18-octadecanol, 1-bromo-18-octadecanol, and the like.

The reaction in the (Step VI-1) can be performed by using, as a basic catalyst, a carbonate salt such as potassium carbonate or the like in a polar solvent such as N,N-dimethylformamide or the like or using as a basic catalyst a tertiary amine such as triethylamine or the like in a halogenated solvent such as dichloromethane, chloroform, or the like.

(Step VI-2)

The secondary amine located at a structural terminal of the intermediate compound C is reacted with a halogenated aromatic compound represented by Hal-Aral in a reaction formula below, whereby a novel compound in which $Y_1$ is an aralkyl group (y1-2) can be produced.

benzyl bromide, phenethyl iodide, phenylbenzyl bromide, methoxyphenylbenzyl bromide, naphthylmethyl bromide, methoxynaphthylmethyl bromide, phenylpropyl iodide, phenylpropenyl iodide, phenoxybenzyl bromide, methylthiobenzyl bromide, terphenylmethyl bromide, and the like. The reaction can be performed under the same reaction conditions as in (Step VI-1).

(Step VI-3)

The secondary amine located at a structural terminal of the intermediate compound C is reacted with a halogenated polyether compound represented by structural formula (y1-3r) below

[Chem. 60]

$$R_9-O(-R_8-O)_m-R_8\text{-Hal} \quad (y1\text{-}3r)$$

(in the formula, $R_8$ represents an alkylene group having 2 to 4 carbon atoms, $R_9$ represents a hydrogen atom, a phenyl group, or an alkyl group having 1 to 4 carbon atoms, and m represents an integer of 0 to 20), whereby a novel compound in which $Y_1$ is a structural formula (y1-3) can be produced.

[Chem. 59]

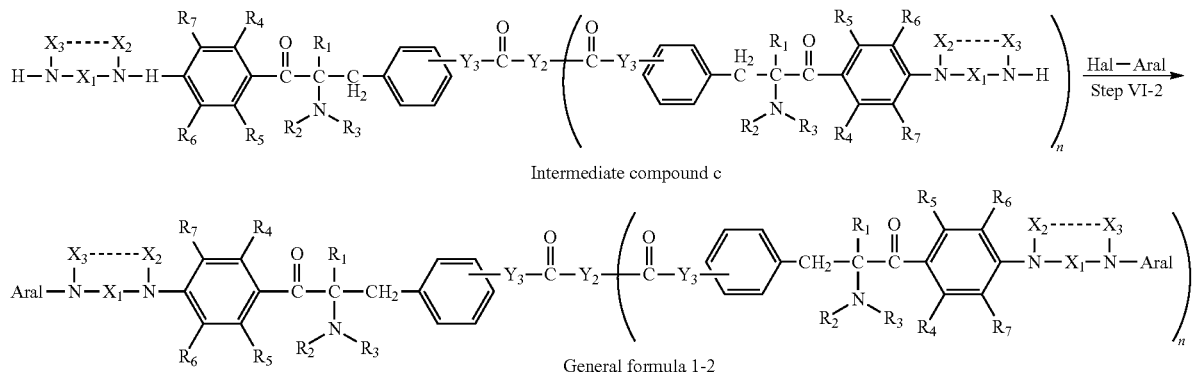

(In the formula, Hal represents a halogen atom, and Aral represents an aralkyl group.)

Examples of the halogenated aromatic compound represented by Hal-Aral in the reaction formula include benzyl chloride, benzyl bromide, methoxybenzyl chloride, methoxybenzyl bromide, chlorobenzyl bromide, hydroxy-

[Chem. 61]

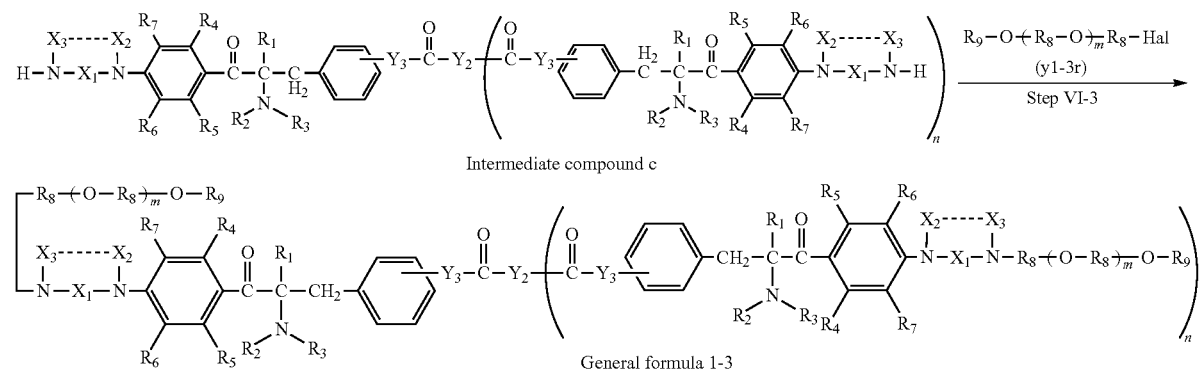

Examples of $R_8$ as an alkylene group having 2 to 4 carbon atoms in the structural formula (y1-3r) and the general formula 1-3 include a n-propylene group, a 1,2-propylene group, a n-butylene group, a 2-methy-propane-1,2-diyl group, and the like, and examples of $R_9$ as an alkyl group having 1 to 4 carbon atoms include a methyl group, an ethyl group, a propyl group, an isopropyl group, a n-butyl group, an isobutyl group, a tert-butyl group, a sec-butyl group, and the like. The reaction in (Step VI-3) can be performed under the conditions of 20° C. to 120° C. in the presence of a basic catalyst such as potassium carbonate or the like.

(Step VI-4)

The secondary amine located at a structural terminal of the intermediate compound C is reacted by Michael addition reaction with a (meth)acryloyl group of a compound represented by structural formula (y1-4r) below

[Chem. 62]

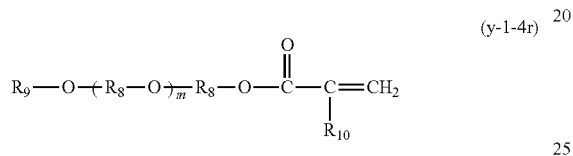

(y-1-4r)

(in the formula, $R_8$ represents an alkylene group having 2 to 4 carbon atoms; $R_9$ represents a hydrogen atom, a phenyl group, or an alkyl group having 1 to 4 carbon atoms, $R_{10}$ represents a hydrogen atom or a methyl group, and m represents an integer of 0 to 20), whereby a novel compound in which $Y_1$ in the general formula 1 is a structural formula (y1-4) can be produced.

[Chem. 63]
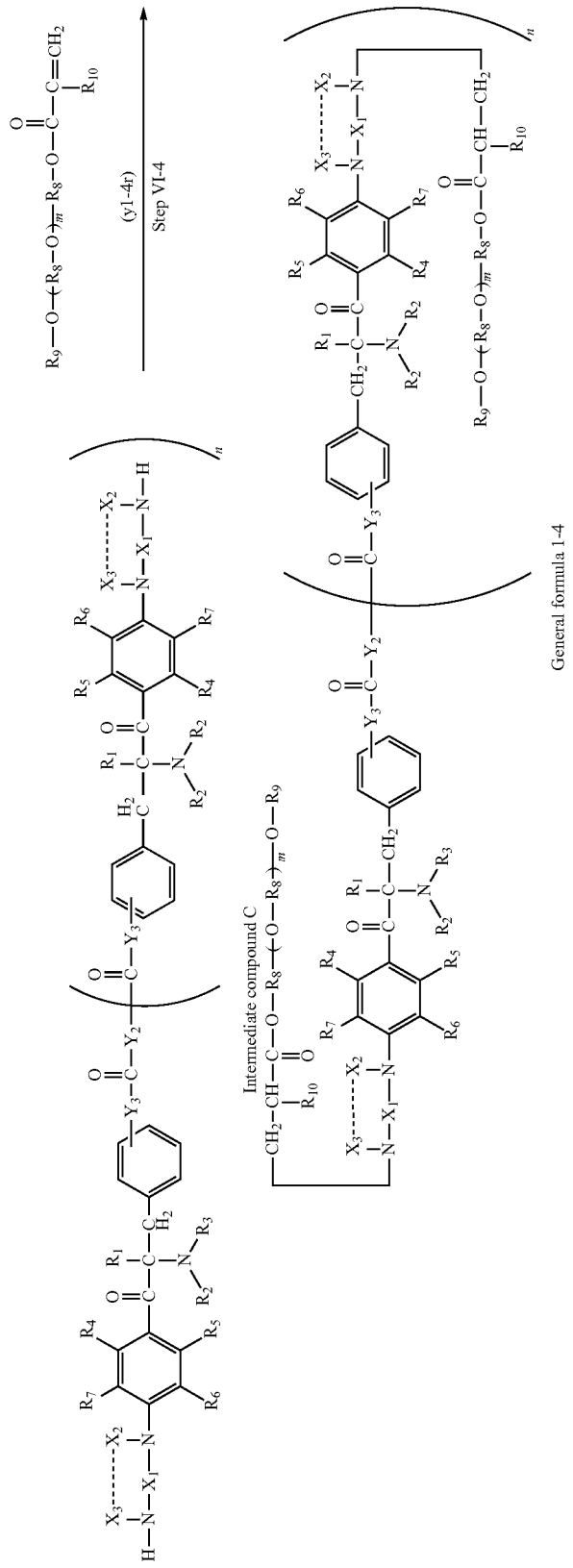

Examples of $R_8$ as an alkylene group having 2 to 4 carbon atoms in the structural formula (y1-4r) and the general formula 1-4 include a n-propylene group, a 1,2-propylene group, a n-butylene group, a 2-methy-propane-1,2-diyl group, and the like, and examples of $R_9$ as an alkyl group having 1 to 4 carbon atoms include a methyl group, an ethyl group, a propyl group, an isopropyl group, a n-butyl group, an isobutyl group, a tert-butyl group, a sec-butyl group, and the like.

The Michael addition reaction in (Step VI-4) can be performed under known common reaction conditions. A general method is, for example, a method of mixing the intermediate compound C with the compound represented by the structural formula (y1-4r) and having the function as a Michael acceptor at 0° C. to 150° C. in a reaction vessel, and a catalyst and a solvent can be used.

Examples of the catalyst which can be used include tetrabutylammonium hydroxide, tetramethylguanidine, diazabicycloundecene, 1,4-diazabicyclo[2.2.2], sodium tert-butyrate, and the like.

Examples of an organic solvent include saturated hydrocarbon solvents such as pentane, hexane, heptane, cyclohexane, and the like; aromatic hydrocarbon solvents such as toluene, xylene, and the like; alcohol solvents such as methanol, ethanol, isopropanol, 2-butanol, tert-butanol, ethylene glycol, carbitol, and the like; ether solvents such as dimethyl ether, diethyl ether, 1,4-dioxane, tetrahydrofuran (THF), and the like; amide solvents such as dimethylformamide (DMF) and the like; halogen solvents such as chloroform, dichloromethane, and the like; dimethylsulfoxide (DMSO); and the like.

The mixing ratio between the intermediate compound C and the compound represented by the structural formula (y1-4r) and having the function as the Michael acceptor is not particularly limited, but the equivalent ratio [(i)/(ii)] of the secondary amino group (i) in the intermediate compound C to the (meth)acryloyl group (ii) in the compound represented by the structural formula (y1-4r) is preferably 1/1.5 to 1/30. With the equivalent ratio [(i)/(ii)] exceeding 1/1.5, the possibility of migration from a coating film of the intermediate compound C or the decomposed product thereof is increased, while with the equivalent ratio [(i)/(ii)] of less than 1/30, the curing performance of the Michael addition reaction product tends to be degraded. From the viewpoint of the curing performance of the Michael addition reaction product and the eluted substance amount of the coating film, the equivalent ratio [(i)/(ii)] is particularly preferably 1/2 to 1/20.

Examples of the structural formula (y1-4r) having the function as the Michael acceptor include methoxyethyl (meth)acrylate, methoxypolyethylene glycol (meth)acrylate, ethoxypolyethylene glycol (meth)acrylate, butoxypolyethylene glycol (meth)acrylate, methoxypolypropylene glycol (meth)acrylate, and the like. The reaction can be performed under the conditions of 20° C. to 120° C. in the presence of a catalyst such as diazabicycloundecene (DBU) or the like.

(Step VI-5)

The secondary amine located at a structural terminal of the intermediate compound C is reacted with a (meth)acryloyl group of a compound represented by structural formula (y1-5r) below

[Chem. 64]

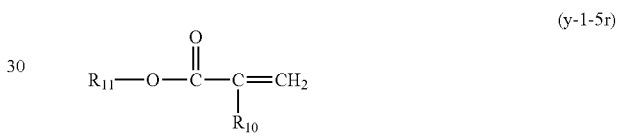

(y-1-5r)

(in the formula, $R_{10}$ represents a hydrogen atom or a methyl group, and $R_{11}$ represents an alkyl group having 1 to 18 carbon atoms or an aryl group having 6 to 18 carbon atoms), whereby a novel compound in which $Y_1$ in the general formula 1 is a structural formula (y1-5r) can be produced.

[Chem. 65]

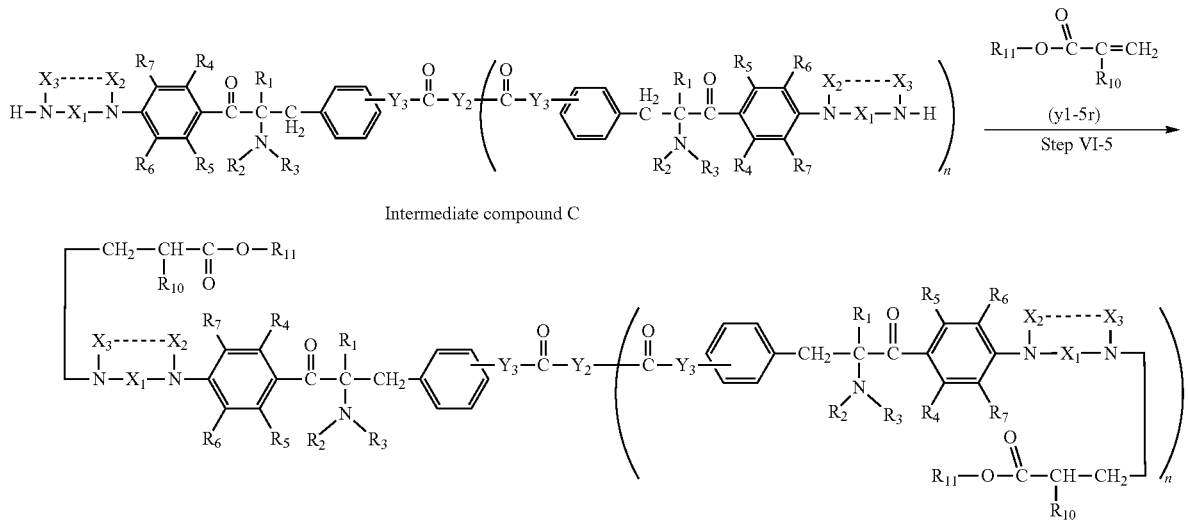

General formula 1-5

Examples of $R_{11}$ as an alkyl group having 1 to 18 carbon atoms include linear or branched alkyl groups such as a methyl group, an ethyl group, a propyl group, an isopropyl group, a n-butyl group, an isobutyl group, a tert-butyl group, a sec-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a 2-ethylbutyl group,

[Chem. 66]

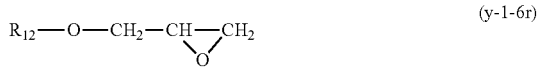

(y-1-6r)

(in the formula, $R_{12}$ represents an alkyl group having 1 to 18 carbon atoms), whereby a novel compound in which $Y_1$ is a structural formula (y1-6) can be produced.

[Chem. 67]

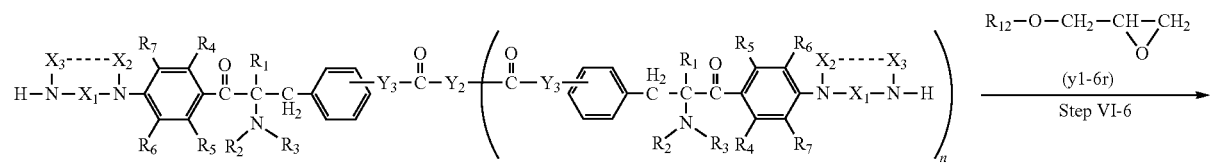

Intermediate compound C

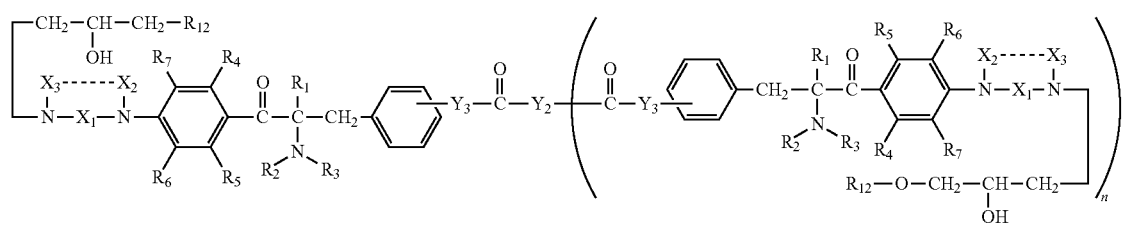

General formula 1-6 an isopentyl group, a 1-methylpentyl group, a 1,3-dimethylbutyl group, a 1-methylhexyl group, an isoheptyl group, a 1,1,3,3-tetramethylbutyl group, a 2,2,4,4-tetramethylbutyl group, a 1-methylheptyl group, a 3-methylheptyl group, a 2-ethylhexyl group, a 1,1,3-trimethylhexyl group, a 1,1,3,3-tetramethylpentyl group, an isodecyl group, a 1-methylundecyl group, a 1,1,3,3,5,5-hexamethylhexyl group, and the like; cycloalkyl groups such as a cycloheptyl group, a cyclohexyl group, a cyclopentyl group, and the like. On the other hand, examples of an aryl group having 6 to 18 carbon atoms include a phenyl group, a benzyl group, a phenethyl group, a biphenyl group, a naphthyl group, a tolyl group, a xylyl group, a mesityl group, a cumenyl group, a chlorophenyl group, a bromophenyl group, a chloromethylphenyl group, a hydroxyphenyl group, a methoxyphenyl group, an ethoxyphenyl group, a phenoxyphenyl group, an acetoxyphenyl group, a benzoyloxyphenyl group, a methylthiophenyl group, a phenylthiophenyl group, a methylaminophenyl group, a dimethylaminophenyl group, an acetylaminophenyl group, a carboxyphenyl group, a methoxycarbonylphenyl group, a phenoxycarbonylphenyl group, a N-phenylcarbamoylphenyl group, a cyanophenyl group, a sulfophenyl group, a sulfonatophenyl group, a phosphonophenyl group, a phosphonatophenyl group, and the like.

(Step VI-6)

The secondary amine located at a structural terminal of the intermediate compound C is reacted with an epoxy group of an epoxy compound represented by structural formula (y1-6r) below Examples of $R_{12}$ as an alkyl group having 1 to 18 carbon atoms in the structural formula (y1-6r) and the general formula (1-6) include linear or branched alkyl groups such as a methyl group, an ethyl group, a propyl group, an isopropyl group, a n-butyl group, an isobutyl group, a tert-butyl group, a sec-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a 2-ethylbutyl group, an isopentyl group, a 1-methylpentyl group, a 1,3-dimethylbutyl group, a 1-methylhexyl group, an isoheptyl group, a 1,1,3,3-tetramethylbutyl group, a 2,2,4,4-tetramethylbutyl group, a 1-methylheptyl group, a 3-methylheptyl group, a 2-ethylhexyl group, a 1,1,3-trimethylhexyl group, a 1,1,3,3-tetramethylpentyl group, an isodecyl group, a 1-methylundecyl group, a 1,1,3,3,5,5-hexamethylhexyl group, and the like; cycloalkyl groups such as a cycloheptyl group, a cyclohexyl group, a cyclopentyl group, and the like.

The reaction with an epoxy compound in (Step VI-6) is performed by a reaction method of mixing the intermediate compound C with the compound represented by the structural formula (y1-6r) under a temperature condition of 0° C. to 150° C. in a reaction vessel. In this method, a catalyst and a solvent can be used.

Examples of the catalyst which can be used include triethylamine, diisopropylethylamine, benzyldiethylamine, imidazole, tetrabutylammonium bromide, tri-n-octylphosphine, triphenylphosphine, and the like.

Examples of an organic solvent include aromatic hydrocarbon solvents such as toluene, xylene, and the like; ethers such as dimethyl ether, diethyl ether, 1,4-dioxane, tetrahydrofuran (THF), and the like; ketone solvents such as acetone, 2-butanone, methyl isobutyl ketone, and the like; amide solvents such as dimethylformamide (DMF) and the like; halogen solvents such as chloroform, dichloromethane, and the like; dimethylsulfoxide (DMSO) and the like.

(Step VI-7)

The secondary amine located at a structural terminal of the intermediate compound C is reacted with an epoxy group of an epoxy compound represented by structural formula (y1-7r) below

[Chem. 68]

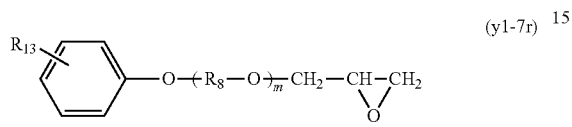

(y1-7r)

(in the formula, $R_8$ represents an alkylene group having 2 to 4 carbon atoms, $R_{13}$ represents a hydrogen atom, an alkyl group having 1 to 6 carbon atoms, or a halogen atom, and m represents an integer of 0 to 20), whereby a novel compound in which $Y_1$ is a structural formula (y1-7) can be produced.

[Chem. 69]
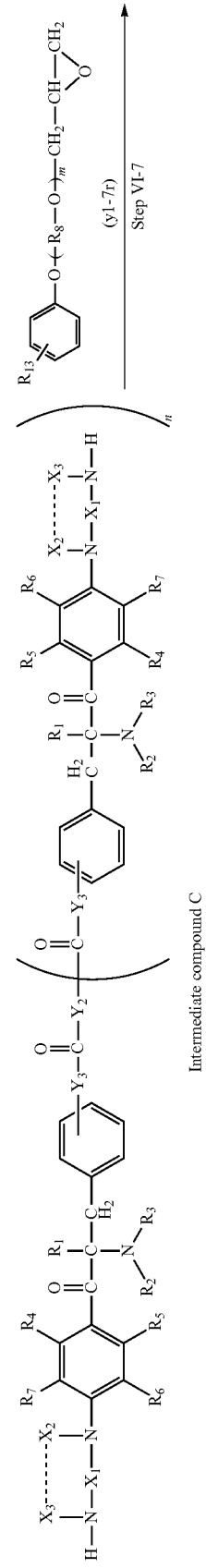
Intermediate compound C
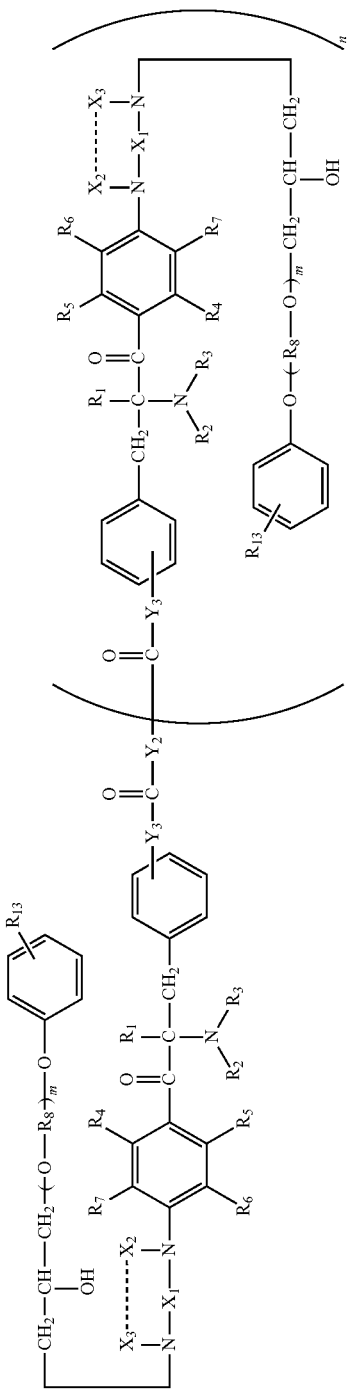
General formula 1-7

Examples of $R_8$ in the structural formula (y1-7r) and the general formula (1-7) represents the same meaning as $R_8$ in the structural part (y1-3), and examples of $R_{13}$ as an alkyl group having 1 to 6 carbon atoms include a methyl group, an ethyl group, a propyl group, an isopropyl group, a n-butyl group, an isobutyl group, a tert-butyl group, a sec-butyl group, a pentyl group, a hexyl group, a 2-ethylbutyl group, an isopentyl group, a 1-methylpentyl group, a 1,3-dimethylbutyl group, and the like. Examples of a halogen atom include a bromine atom, a chlorine atom, and a fluorine atom.

The reaction with an epoxy compound in Step VI-7 is performed by, for example, a reaction method of mixing the intermediate compound C with the compound represented by the structural formula (y1-7r) at 0° C. to 150° C. in a reaction vessel. In this method, a catalyst and a solvent can be used.

Examples of the catalyst which can be used include triethylamine, diisopropylethylamine, benzyldiethylamine, imidazole, tetrabutylammonium bromide, tri-n-octylphosphine, triphenylphosphine, and the like.

Examples of an organic solvent include aromatic hydrocarbon solvents such as toluene, xylene, and the like; ethers such as dimethyl ether, diethyl ether, 1,4-dioxane, tetrahydrofuran (THF), and the like; ketone solvents such as acetone, 2-butanone, methyl isobutyl ketone, and the like; amide solvents such as dimethylformamide (DMF) and the like; halogen solvents such as chloroform, dichloromethane, and the like; dimethylsulfoxide (DMSO) and the like.

(Step VI-8)

The secondary amine located at a structural terminal of the intermediate compound C is reacted with a (meth) acryloyl group of a compound represented by structural formula (y1-8r) below

[Chem. 70]

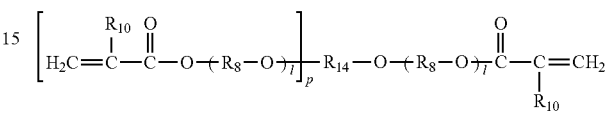

(y1-8r)

(in the formula, $R_8$ represents an alkylene group having 2 to 4 carbon atoms, $R_{10}$ represents a hydrogen atom or a methyl group, $R_{14}$ represents a hydrocarbon group having 5 to 18 carbon atoms and (p+1) bonds, 1 represents an integer of 0 to 20, and p represents an integer of 1 to 3), whereby a novel compound in which $Y_1$ in the general formula 1 is a structural formula (y1-8) can be produced.

[Chem. 71]
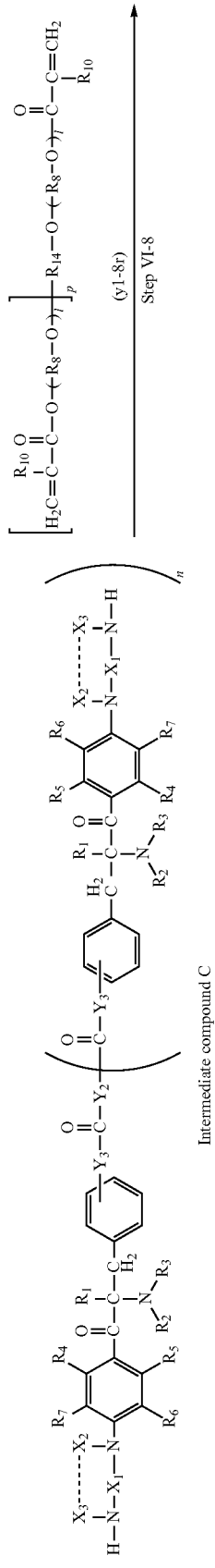
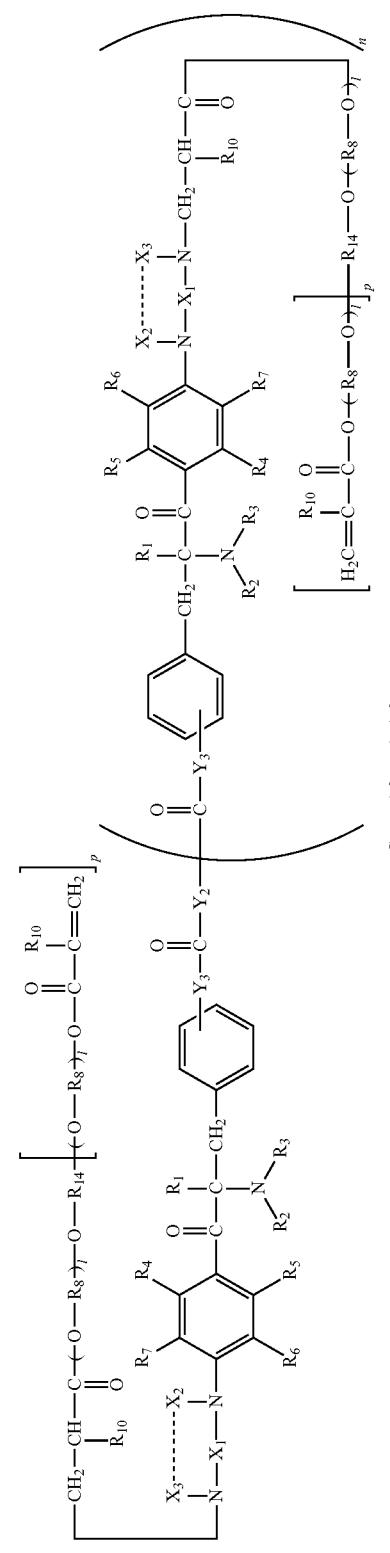

In the formula, $R_8$ in the structural formula (y1-8r) and the general formula (1-8) represents the same meaning as $R_8$ in the structural part (y1-3), and examples of $R_{14}$ as a hydrocarbon group having 3 to 25 carbon atoms and (p+1) bonds include aliphatic polyhydric alcohol residues such as a glycerol residue, a trimethylolpropane residue, a pentaerythritol residue, and the like; a n-propylene group, a 1,2-propylene group, a n-butylene group, a 2-methyl-propane-1,2-diyl group, a 1,5-pentanediyl group, a 1,6-hexanediyl group, a 1,7-heptanediyl group, a 1,8-octanediyl group, a 1,9-nonanediyl group, a 1,10-decanediyl group, a 3,8-decanediyl group, a 1,11-undecanediyl group, a 1,12-dodecanediyl group, a 1,13-tridecanediyl group, a 1,14-tetradecanediyl group, a 1,15-pentadecanediyl group, a 1,16-hexadecanediyl group, a 1,17-heptadecanediyl group, a 1,18-octadecanediyl group, a 1,19-nonadecanediyl group, a 1,20-eicosanediyl group, a 1,21-heneicosanediyl group, a 1,22-docosanediyl group, 1,23-tricosanediyl group, a 1,24-tetracosanediyl group, a 1,25-pentacosanediyl group, and the like.

Herein, the term "residue" represents a hydrocarbon structural part excluding a hydroxyl group of a polyhydric alcohol.

The Michael addition reaction in (Step VI-8) can be performed under known common reaction conditions. A general method is, for example, a method of mixing the intermediate compound C with the compound represented by the structural formula (y1-8r) and having the function as a Michael acceptor at 0° C. to 150° C. in a reaction vessel, and a catalyst and a solvent can be used.

Examples of the catalyst which can be used include tetrabutylammonium hydroxide, tetramethylguanidine, diazabicycloundecene, 1,4-diazabicyclo[2.2.2], sodium tert-butyrate, and the like.

Examples of an organic solvent include saturated hydrocarbon solvents such as pentane, hexane, heptane, cyclohexane, and the like; aromatic hydrocarbon solvents such as toluene, xylene, and the like; alcohol solvents such as methanol, ethanol, isopropanol, 2-butanol, tert-butanol, ethylene glycol, carbitol, and the like; ether solvents such as dimethyl ether, diethyl ether, 1,4-dioxane, tetrahydrofuran (THF), and the like; amide solvents such as dimethylformamide (DMF) and the like; halogen solvents such as chloroform, dichloromethane, and the like; dimethylsulfoxide (DMSO); and the like.

The mixing ratio between the intermediate compound C and the compound represented by the structural formula (y1-8r) and having the function as the Michael acceptor is not particularly limited, but the equivalent ratio [(1)/(ii)] of the secondary amino group (i) in the intermediate compound C to the (meth)acryloyl group (ii) in the compound represented by the structural formula (y1-8r) is preferably 1/1.5 to 1/30. With the equivalent ratio [(i)/(ii)] exceeding 1/1.5, the possibility of migration from a coating film of the intermediate compound C or the decomposed product thereof is increased, while with the equivalent ratio [(i)/(ii)] of less than 1/30, the curing performance of the Michael addition reaction product tends to be degraded. From the viewpoint of the curing performance of the Michael addition reaction product and the eluted substance amount of the coating film, the equivalent ratio [(i)/(ii)] is particularly preferably 1/2 to 1/20.

Examples of the compound represented by the structural formula (y1-8r) and having the function as the Michael acceptor include, but are not limited to, difunctional acrylates such as diethylene glycol di(meth)acrylate, dipropylene glycol di(meth)acrylate, tripropylene glycol di(meth)acrylate, 3-methyl-1,5-pentanediol di(meth)acrylate, hexanediol di(meth)acrylate, neopentylglycol di(meth)acrylate, and the like; trimethylolpropane tri(meth)acrylate and modified products thereof modified with alkylene oxides such as ethylene oxide, propylene oxide, and the like; pentaerythritol tri or tetra(meth)acrylate and modified products thereof modified with alkylene oxides such as ethylene oxide, propylene oxide, and the like; ditrimethylolpropane tetra (meth)acrylate and modified products thereof modified with alkylene oxides such as ethylene oxide, propylene oxide, and the like; polyfunctional (meth)acrylates such as dipentaerythritol tetra-, penta-, or hexa(meth)acrylate, caprolactone-modified products thereof, and the like; epoxy(meth)acrylate produced by reaction of polyglycidyl ether such as bisphenol A diglycidyl ether, trimethylolpropane triglycidyl ether, or the like with (meth)acrylic acid; urethane (meth)acrylate produced by reaction of a polyisocyanate compound such as isophorone diisocyanate or hexamethylene diisocyanate trimer or the like with a hydroxyl group-containing acrylate such as hydroxyethyl (meth)acrylate, pentaerythritol tri(meth)acrylate, or the like; polyester (meth)acrylate produced by reaction of a polybasic acid such as trimellitic acid, succinic acid, or the like with polyol such as ethylene glycol, neopentylglycol, or the like and a hydroxyl group-containing (meth)acrylate such as hydroxyethyl (meth)acrylate, pentaerythritol tri(meth)acrylate, or the like; high-molecular-weight poly(meth)acrylate produced by reaction of a polymer of glycidyl (meth)acrylate and monofunctional (meth)acrylate with (meth)acrylic acid; and the like. These reactive compounds may be used alone or as a mixture of a plurality of compounds.

(Step VI-9)

The secondary amine located at a structural terminal of the intermediate compound C is reacted with an isocyanate group of an isocyanate compound represented by structural formula (y1-9r) below

[Chem. 72]

$$R_{15}\text{—NCO} \qquad (y1\text{-}9r)$$

(in the formula, $R_{15}$ represents an alkyl group having 4 to 18 carbon atoms, an aliphatic cyclic hydrocarbon group having 6 to 10 carbon atoms, an aromatic group, or an acryloyloxyethyl group), whereby a novel compound in which $Y_1$ is a structural formula (y1-9) can be produced.

[Chem. 73]

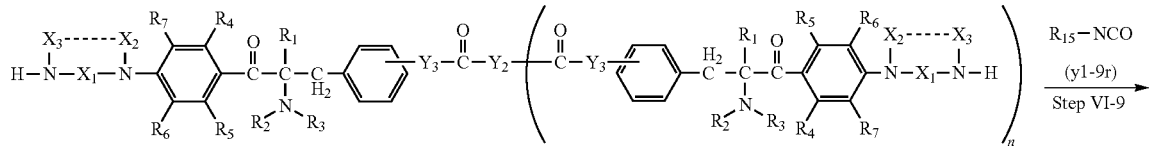

Intermediate compound C

-continued

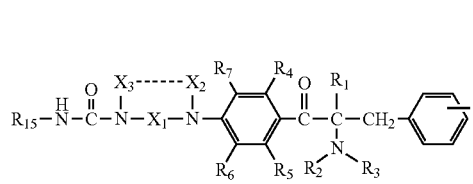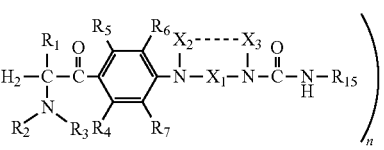

General formula 1-9

Examples of an isocyanate compound represented by the structural formula (y1-9r) include alkyl isocyanates having 4 to 18 carbon atoms, such as propyl isocyanate, butyl isocyanate, hexyl isocyanate, dodecyl isocyanate, octadecyl isocyanate, and the like; isocyanate group-containing aliphatic cyclic hydrocarbons such as cyclohexyl isocyanate, adamantyl isocyanate, and the like; isocyanate group-containing aromatic hydrocarbons such as phenyl isocyanate, benzyl isocyanate, phenethyl isocyanate, toluidyl isocyanate, and the like.

The reaction of the intermediate compound C with the isocyanate compound represented by the structural formula (y1-9r) in (Step VI-9) can be performed by, for example, a method of mixing the both compounds at 0° C. to 150° C. in a reaction vessel, and a catalyst and a solvent can be used.

Examples of the catalyst which can be used include triethylamine, diazabicycloundecene, dibutyltin dilaurate, tri-n-octylphosphine, triphenylphosphine, and the like.

Examples of an organic solvent include aromatic hydrocarbon solvents such as toluene, xylene, and the like; ether solvents such as dimethyl ether, diethyl ether, 1,4-dioxane, tetrahydrofuran (THF), and the like; ketone solvents such as acetone, 2-butanone, methyl isobutyl ketone, and the like; amide solvents such as dimethylformamide (DMF) and the like; halogen solvents such as chloroform, dichloromethane, and the like; dimethylsulfoxide (DMSO); and the like.

The novel compound of the present invention described in detail above is useful as a photopolymerization initiator and a photocurable composition can be produced by mixing with a photocurable compound such as a photocurable monomer, a photocurable resin, or the like.

That is, the photocurable composition of the preset invention is characterized by using the novel compound of the present invention as a photopolymerization initiator and containing a photocurable compound, and a maleimide compound having an ethylenically double bond, a maleic acid ester compound, a fumaric acid ester compound, a (meth)acrylate compound, or the like can be used as the photocurable compound according to application.

Specifically, the photocurable composition of the present invention can be used for various applications such compositions for a printing ink, an ink for ink jet recording, a coating material, a molding resin, a cast molding resin, a resin for optical shaping, a sealing agent, a dental polymer resin, a photosensitive resin for printing plates, a color proof for printing, a resist for color filters, a resist for black matrixes, a photospacer for liquid crystals, a screen material for rear projection, an optical fiber, a rib material for plasma display, a dry film resist, a resist for printed boards, a solder resist, a photoresist for semiconductors, resist for microelectronics, resist for manufacturing micromachine components, an etching resist, a micro-lens array, an insulating material, a hologram material, an optical switch, a material for light guides, an overcoat agent, powder coating, an adhesive, a pressure-sensitive adhesive, a mold release agent, an optical recording medium, an adhesive/pressure-sensitive adhesive, a release coat agent, an image recording material using micro capsules, and the like. As described above, the photocurable composition of the present invention can decrease the migration of the photopolymerization initiator and decomposed product thereof after curing and can exhibit excellent curability, and is thus very effective in safety and sanitation. For example, the photocurable composition of the present invention can be preferably used as a printing ink for offset printing, such as package printing for food packages, toys, sanitary/cosmetic/medical products, and the like, an ink for ink jet recording, and the like.

When the photocurable composition of the present invention is used as a printing ink, the photocurable compound is preferably a polyfunctional (meth)acrylate compound having a plurality of reactive groups contributing to curing by irradiation. Examples thereof include monomer-type polyvalent (meth)acrylates such as difunctional acrylates diethylene glycol di(meth)acrylate, dipropylene glycol di(meth)acrylate, tripropylene glycol di(meth)acrylate, 3-methyl-1,5-pentanediol di(meth)acrylate, hexanediol di(meth)acrylate, neopentylglycol di(meth)acrylate, and the like, polyfunctional (meth)acrylates such as trimethylolpropane tri(meth)acrylate and tri(meth)acrylates of trihydric alcohols produced by modifying trimethylolpropane with alkylene oxides such as ethylene oxide, propylene oxide, and the like, pentaerythritol tri- or tetra(meth)acrylate and tri- or tetra (meth)acrylates of tetrahydric alcohols produced by modifying pentaerythritol with alkylene oxides such as ethylene oxide, propylene oxide, and the like, ditrimethylolpropane tetra(meth)acrylate and tri- or tetra(meth)acrylates of tetrahydric alcohols produced by modifying ditrimethylolpropane with alkylene oxides such as ethylene oxide, propylene oxide, and the like, dipentaerythritol tetra-, penta- or hexa (meth)acrylate, caprolactone-modified product of dipentaerythritol, and the like;

oligomer-type polyvalent (meth)acrylates such as epoxy (meth)acrylate produced by reaction of polyglycidyl ether such as bisphenol A diglycidyl ether, trimethylolpropane triglycidyl ether, or the like with (meth)acrylic acid; urethane (meth)acrylate produced by reaction of a polyisocyanate compound such as isophorone diisocyanate or hexamethylene diisocyanate trimer or the like with a hydroxyl group-containing acrylate such as hydroxyethyl (meth)acrylate, pentaerythritol tri(meth)acrylate, or the like; polyester (meth)acrylate produced by reaction of a polybasic acid such as trimellitic acid, succinic acid, or the like with polyol such as ethylene glycol, neopentylglycol, or the like and a hydroxyl group-containing (meth)acrylate such as hydroxyethyl (meth)acrylate, pentaerythritol tri(meth)acrylate, or the like; high-molecular-weight poly(meth)acrylate produced by reaction of a polymer of glycidyl (meth)acrylate and monofunctional (meth)acrylate with (meth)acrylic acid; and the like.

Among these, the tri- or higher functional monomer-type (meth)acrylate compound is most preferred as the reactive compound because it can be strongly fixed as a cured film including a polymer after curing. Also, in the present invention, the oligomer-type polyvalent (meth)acrylate is preferably mixed as a binder resin in addition to the tri- or higher functional monomer-type (meth)acrylate compound. In this case, the mixing ratio of the tri- or higher functional monomer-type (meth)acrylate compound to the oligomer-type polyvalent (meth)acrylate is preferably such that the mass ratio [former/latter] is 10/100 to 300/100.

Also, when the viscosity of an ink is desired to be decreased, a monofunctional (meth)acrylate compound or monofunctional vinyl ether compound, which is a monomer-type monofunctional compound, can also be used as the photopolymerizable compound from the viewpoint of adjustment of the viscosity of a photocurable printing ink of the present invention.

Examples of the monofunctional (meth)acrylate compound include (meth)acrylic acid alkyl esters such as methyl acrylate, ethyl acrylate, butyl acrylate, 2-ethylhexyl acrylate, and the like; hydroxyalkyl (meth)acrylates such as 2-hydroxyethyl acrylate, 2-hydroxypropyl acrylate, and the like; alkoxyalkyl (meth)acrylates such as butoxyethyl acrylate, methoxybutyl (meth)acrylate, and the like; polyalkylene glycol (meth)acrylates such as polyethylene glycol mono (meth)acrylate, methoxydiethylene glycol (meth)acrylate, phenoxypolyethylene glycol (meth)acrylate, polypropylene glycol mono(meth)acrylate, methoxypolypropylene glycol (meth)acrylate, nonylphenoxypolypropylene glycol (meth)acrylate, and the like; cycloakyl (meth)acrylates such as cyclohexyl (meth)acrylate, dicyclopentadienyl (meth)acrylate, isobornyl (meth)acrylate, and the like; (meth)acrylates such as benzyl (meth)acrylate, 2-hydroxyethyl (meth)acryloyl phosphate, tetrahydrofurfuryl (meth)acrylate, diethylaminoethyl (meth)acrylate, dimethylaminomethyl S (meth) acrylate, and the like; (meth)acrylamides such as diacetone (meth)acrylamide, acryloylmorpholine, and the like.

On the other hand, examples of the monofunctional vinyl ether compound include alkyl vinyl ethers and cycloalkyl vinyl ethers such as ethyl vinyl ether, isobutyl vinyl ether, 2-ethylhexyl vinyl ether, cyclohexyl vinyl ether, and the like; hydroxyl group-containing vinyl ethers such as 2-hydroxyethyl vinyl ether, 3-hydroxypropyl vinyl ether, and the like.

When the monofunctional (meth)acrylate compound or monofunctional vinyl ether compound is used, the amount of use is preferably an amount which does not increase the migration of unreacted monomers and does not induce a decrease in abrasion resistance of an ink coating film, and specifically within a range of 30% by mass or less in the photopolymerization compound (A).

Besides the photopolymerization initiator of the present invention and the photopolymerizable compound, the photocurable printing ink of the present invention can contain a pigment, a binder resin, other various additives, etc.

With respect to the mixing ratio of each of the components, preferably, the pigment is 1 to 70 parts by mass and the binder resin is 3 to 70 parts by mass relative to 100 parts by mass of a mixture of the photocurable compound and the polymerization initiator. In view of the balance between the color density of a printed matter and printability, the pigment is preferably 5 to 30 parts by mass and the binder resin is preferably 5 to 50 parts by mass relative to 100 parts by mass of a mixture of the photocurable compound and the initiator. The resultant offset ink is preferably designed to generally have 3 to 200 Pa·s (25° C.) depending on the printing machined used.

In this case, an inorganic pigment or an organic pigment can be used as the pigment used. Examples of the inorganic pigment which can be used include chrome yellow, Prussian blue, barium sulfate, cadmium red, titanium oxide, zinc flower, alumina white, calcium carbonate, ultramarine blue, carbon black, graphite, Bengara, iron oxide, and carbon black produced by a contact method, a furnace method, a thermal method, or the like. In the present invention, as described above, excellent curability is exhibited even by using carbon black which easily absorbs UV light at a long wavelength, and thus a UV printing ink having good curability can be produced by mixing carbon black.

Examples of the organic pigment which can be used include various known common pigments such as azo pigments (including an azo lake, an insoluble azo pigment, a condensed azo pigment, a chelate azo pigment, and the like), polycyclic pigments (for example, a phthalocyanine pigment, a perylene pigment, a perinone pigment, an anthraquinone pigment, a quinacridone pigment, a dioxazine pigment, a thioindigo pigment, an isoindolinone pigment, a quinophthalone pigment, and the like), dye chelates (for example, a basic dye-type chelate, an acid dye-type chelate, and the like), nitro pigments, nitroso pigments, aniline black, various fluorescent pigments, metal powder pigments, and the like.

The average particle diameter of the pigment is appropriately designed according to application. For example, when the photocurable composition of the present invention is applied to a printing ink such as an offset ink or the like, the average particle diameter of the pigment is preferably within a range of 10 to 500 nm and more preferably about 50 to 300 nm.

When the pigment is used, a pigment dispersant is preferably used for the purpose of enhancing dispersion stability with the photopolymerizable compound and the like. Specific examples thereof include, but are not limited to, "Ajisper PB821", "PB822", and "PB817" manufactured by Ajimonoto Fine-Techno Co., Ltd., "Solsperse 5000", "24000GR", "32000", "33000", "36000", "39000", and "44000" manufactured by Lubrizol Corporation, "Disparlon DA-703-50", "DA-705", and "DA-725" manufactured by Kusumoto Chemical, Ltd., "DISPERBYK111", "YK168", and "YK180" manufactured by BYK Inc., and the like. The amount of the pigment dispersant used is preferably within a range of 3% to 80% by mass and particularly preferably within a range of 5% to 60% by mass relative to the pigment. When the amount of use is less than 3% by mass, dispersion stability tends to be unsatisfactory, while when the amount exceeds 80% by mass, the ink viscosity tends to increase.

Next, the binder resin may be any general resin which has proper affinity and dispersibility with the pigment and rheological properties required for the printing ink, and the oligomer-type polyvalent (meth)acrylates exemplified as the photopolymerizable compound (A) can be used. Other examples include nonreactive resins such as diallyl phthalate resins, epoxy resins, polyurethane resins, polyester resins, petroleum resins, rosin ester resins, poly(meth)acrylic acid esters, cellulose derivatives, vinyl chloride-vinyl acetate copolymer, polyamide resins, polyvinyl acetal resins, butadiene-acrylonitrile copolymer, and the like. Also, resins each having at least one polymerizable group in the resin molecule, such as an epoxy acrylate resin, urethane acrylate resin, polyester acrylate resin, and the like, can be used.

Among the binder resins described above, the diallyl phthalate resins are preferred from the viewpoint of excellent printability, little elusion of a low-molecular-weight component derived from the resins, and excellent solubility in the photocurable composition. However, there is concern that 2-hydroxyethyl acrylate having high skin irritation remains in the diallyl phthalate resins, and thus the urethane acrylate resins are preferred from the viewpoint of safety and sanitation. Among the urethane acrylate resins, a urethane (meth)acrylate resin having a (meth)acryloyl group concentration of 1.5 to 4.0 mmol/g is particularly preferred in view of excellent printability and excellent curability, the urethane (meth)acrylate resin being produced by reacting a polyfunctional aromatic isocyanate (a) with a hydroxyl group-containing mono(meth)acrylate (b) at a ratio such that the ratio [(b')/(a')] of hydroxyl group (b') of the latter to isocyanate group (a') of the former (a) is within a range of 0.99 to 0.40 and then reacting the resultant reaction product with polyol (c).

The urethane (meth)acrylate resin having a (meth)acryloyl group concentration of 1.5 to 4.0 mmol/g produces a printing ink having good printability because the aromatic polyisocyanate (a) is used as a raw material polyisocyanate. Further, when the aromatic polyisocyanate (a) is reacted with the hydroxyl group-containing mono(meth)acrylate (b) at a ratio such that the amount of the latter is relatively large and then subjected to crosslinking with the polyol (c), the (meth)acryloyl group concentration can be increased and the molecular weight can be made relatively low, and thus both the excellent curability and printability as a printing ink can be achieved. When the ratio [(b')/(a')] exceeds 0.99, the hydroxyl group-containing mono(meth)acrylate (b) having high skin irritation easily remains in the printing ink, thereby causing the problem with safety and sanitation in handling the printing ink. In addition, the molecular weight of the finally obtained resin is not increased, thereby causing a decrease in curability and misting property. On the other hand, when the ratio [(b')/(a')] is less than 0.40, there remain many isocyanate groups contributing to the crosslinking reaction with the polyol (c) in the next step, and thus gelation easily occurs during synthesis. In addition, even if the resin can be synthesized, aromaticity of the finally obtained urethane (meth)acrylate resin is decreased, thereby decreasing offset printability.

Examples of the polyfunctional aromatic isocyanate (a) used include diisocyanate compounds such as 2,4-tolylene diisocyanate, 2,6-tolylene diisocyanate, 1,3-xylylene diisocyanate, diphenylmethane-4,4-diisocyanate, 1,5-naphthalene diisocyanate, and the like; polymethylene polyphenyl polyisocyanate; and polyfunctional polyisocyanate compounds each containing a component having three or more isocyanate groups in one molecule, such as adducts of these isocyanate compounds and polyfunctional alcohols. These polyfunctional aromatic isocyanates may be used alone or in combination of two or more. In the present invention, the chemical structure of the polyfunctional isocyanate compound as a raw material is provided with an aromatic structure, and thus when the printing ink using the finally obtained urethane (meth)acrylate resin is produced, excellent curability can be exhibited.

Among these, the polyfunctional polyisocyanate compounds each containing a component (tri- or higher functional component) having three or more isocyanate groups in one molecule are particularly preferred because the UV curable ink having more excellent curability can be designed. Specifically, the content of the tri- or higher functional component is preferably 30% by mass or more. An example of the aromatic polyisocyanate containing a tri- or higher functional component is polymethylene polyphenyl polyisocyanate, and polymethylene polyphenyl polyisocyanate having a viscosity of 100 to 700 mPa·s is particularly preferred. The viscosity is a value measured by an E-type viscometer (25° C.).

Examples of the hydroxyl group-containing mono(meth)acrylate (b) reacted with the polyfunctional aromatic isocyanate (a) include hydroxyl group-containing (meth)acrylates such as hydroxyethyl (meth)acrylate, hydroxypropyl (meth)acrylate, hydroxybutyl acrylate, hydroxyethyl vinyl ether, and the like; ethylene oxide adducts of the hydroxyl group-containing (meth)acrylates; propylene oxide adducts, tetramethylene glycol adducts, and lactone adducts of the hydroxyl group-containing (meth)acrylates; and the like. These hydroxyl group-containing mono(meth)acrylates (b) may be used alone or in combination of two or more. Among these, hydroxyethyl acrylate and hydroxypropyl acrylate are particularly preferred in view of excellent curability of the composition.

A method of reacting the polyfunctional aromatic isocyanate (a) with the hydroxyl group-containing mono(meth)acrylate (b) is, for example, a method of adding the polyfunctional aromatic isocyanate (a) and, if required a known common urethanization catalyst, heating the mixture to 20° C. to 120° C., continuously or intermittently adding a predetermined amount of the hydroxyl group-containing mono(meth)acrylate (b) to the reaction system, and performing reaction.

In this case, in combination with the polyfunctional aromatic isocyanate (a) and the hydroxyl group-containing mono(meth)acrylate (b), a higher alcohol such as lauryl alcohol, stearyl alcohol, or oleyl alcohol and a hydroxyl group-containing oil and fat such as castor oil are added at a ratio of 0.1 to 30 parts by mass in a total of 100 parts by mass of the reaction raw materials. Therefore, flowability and misting resistance of the finally obtained printing ink can be significantly improved.

Next, the intended urethane (meth)acrylate resin can be produced by reacting the resultant reaction product with the polyol (c). The polyol (c) is preferably an aliphatic polyhydric alcohol having a molecular weight within a range of 90 to 400 in view of curability and printability. That is, with the molecular weight of less than 90, the effect of properly improving offset printability is decreased, while with the molecular weight exceeding 400, the functional group concentration of the finally obtained urethane (meth)acrylate resin is decreased, thereby decreasing the curability improving effect.

From this viewpoint, examples of the polyol include difunctional polyols such as neopentyl glycol, 1,3-butanediol, 1,4-butanediol, tripropylene glycol, and the like; trifunctional polyols such as glycerin, trimethylolpropane, and the like; tetrafunctional polyols such as pentaerythritol, ditrimethylolpropane, and the like; hexafunctional polyols such as dipentaerythritol and the like; ethylene oxide adducts (addition of 1 to 4 moles per molecule on average) of the trifunctional polyols, propylene oxide adducts (addition of 1 to 4 moles per molecule on average) of the trifunctional polyols, 1,3-butanediol adducts (addition of 1 to 2 moles per molecule on average) of the trifunctional polyols, ethylene oxide adducts (addition of 1 to 3 moles per molecule on average) of the tetrafunctional polyols, ethylene oxide adducts (addition of 1 to 3 moles per molecule on average) of the hexafunctional polyols, and the like. These polyols (c) may be used alone or in combination of two or more. Among these, the trifunctional polyols such as glycerin, trimethylolpropane, and the like, neopentyl glycol, 1,6-hexanediol, and tripropylene glycol are preferred from the viewpoint that the urethane (meth)acrylate resin having a proper branched structure can be produced, and excellent offset printability ad curability can be exhibited, and the trifunctional polyols such as glycerin, trimethylolpropane, and the like are particularly preferred in view of excellent curability.

In this case, the polyol (c) is preferably added at a ratio of 1% to 15% by mass relative to the total mass of the component (a) to the component (c) in view of the point that the (meth)acryloyl group concentration in the finally obtained urethane (meth)acrylate resin (A) is increased, and curability and printability are significantly improved.

The reaction product of the aromatic polyisocyanate (a) and the hydroxyl group-containing mono(meth)acrylate (b) is reacted with the polyol (c) by, for example, a method of adding the polyol (c) to the reaction product, heating the mixture to 20° C. to 120° C., and performing reaction until an infrared absorption spectrum at 2250 cm$^{-1}$ showing an isocyanate group disappears.

The urethane (meth)acrylate resin produced as described above is a urethane (meth)acrylate resin having a high (meth)acryloyl group concentration and having a structure in which the reaction product of the aromatic polyisocyanate (a) and the hydroxyl group-containing mono(meth)acrylate (b) is linked through the polyol (c). Specifically, the urethane (meth)acrylate resin (A) has a (meth)acryloyl group concentration within a range of 1.5 to 4.0 mmol/g, and thus excellent curability can be exhibited.

The urethane (meth)acrylate resin (A) produced as described above preferably has a weight-average molecular weight (Mw) within a range of 3,000 to 40,000 from the viewpoint that the printing ink has excellent flowability, misting property, and printability.

In order to further enhance curability, the photocurable printing ink of the present invention may use a photosensitizer or amine-based sensitizer in addition to the components described above.

Examples of the photosensitizer include, but are not particularly limited to, thioxanthone-based photosensitizers such as 2,4-diethyl thioxanthone, 2,4-diisopropyl thioxanthone, and the like, benzophenone-based photosensitizers such as 4,4'-bis(diethylamino)benzophenone and the like, anthraquinone, and the like.

On the other hand, examples of the amine-based sensitizer include an aminobenzoate compound ("Genopol AB-2" manufactured by RAHN Corporation), a compound having two dimethylaminobenzoate structures in one molecule ("ESACURE A198" manufactured by Lamberti Co., Ltd.), a compound having aminobenzoyl groups at both ends of a polyethylene glycol chain ("Omnipol ASA" manufactured by IGM Resins, Inc.), ethyl-4-dimethylaminobenzoate ("ESACURE A198" manufactured by Lamberti Co., Ltd.), and the like. Among these, compounds having a relatively high molecular weight, such as an aminobenzoate compound ("Genopol AB-2" manufactured by RAHN Corporation), a compound having two dimethylaminobenzoate structures in one molecule ("ESACURE A198" manufactured by Lamberti Co., Ltd.), and a compound having aminobenzoyl groups at both end of a polyethylene glycol chain ("Omnipol ASA" manufactured by IGM Resins, Inc.) are particularly preferred from the viewpoint of preventing migration.

The amount of the amine-based sensitizer used is preferably 5 to 100 parts by mass relative to 100 parts by mass of the sensitizer (C).

The photosensitizer or the amine-based sensitizer is preferably used in an amount of 0.03 to 20 parts by mass and more preferably 0.1 to 10 parts by mass relative to the total amount of the photocurable printing ink.

Also, a known photopolymerization initiator can be simultaneously used within a range in which the effect of the present invention is not impaired. Preferred examples thereof include benzoin isobutyl ether, 2,4-diethyl thioxanthone, 2-isopropyl thioxanthone, 2,4,6-trimethylbenzoyl diphenylphosphine oxide, 2-benzyl-2-dimethylamino-1-(4-morpholinophenyl)-butan-1-one, bis(2,6-dimethoxybenzoyl)-2,4,4-trimethylpentyl phosphine oxide, bis(2,4,6-trimethylbenzoyl)-phenylphosphine oxide, and the like. Besides these, a molecular cleavage-type such as 1-hydroxycyclohexyl phenyl ketone, benzoin ethyl ether, benzyl dimethyl ketal, 2-hydroxy-2-methyl-1-phenylpropan-1-one, 1-(4-isopropylphenyl)-2-hydroxy-2-methylpropan-1-one, 2-methyl-1-(4-methylthiophenyl)-2-morpholinopropan-1-one, or the like may be combined. Further, a hydrogen abstraction-type photopolymerization initiator such as benzophenone, 4-phenylbenzophenone, isophthalphenone, 4-benzoyl-4'-methyldiphenyl sulfide, or the like can be combined.

If required, various coupling agents, an extender pigment, an antioxidant, a polymerization inhibitor, a stabilizer, a filler, other auxiliaries, etc. can be further added within a range without deviating from the object of the present invention, particularly within a range in which storage stability, heat resistance, solvent resistance, and the like can be maintained.

The extender pigment is widely used for the purpose of improving the physical properties and imparting functionality, such as adjusting ink flowability, preventing misting during printing, and preventing permeation to a paper substrate. Examples of the extender pigment include known common organic pigments for coloring, for example, extender pigments for printing inks described in "Pigment Handbook" (edited by Japan Pigment Technology Association), and calcium carbonate, magnesium carbonate, kaolin clay, talc, bentonite, mica, barium sulfate, silica, aluminum hydroxide, and the like can be used.

The coupling agent is a compound which chemically combines both an inorganic material and an organic material or enhances the function of a composite material by improving affinity accompanied with chemical reaction. Examples thereof include silane-based compounds such as γ-(2-aminoethyl)aminopropyl trimethoxysilane, γ-(2-aminoethyl) aminopropylmethyl dimethoxysilane; γ-methacryloxypropyl trimethoxysilane; γ-glycidoxypropyl trimethoxysilane, and the like, titanium-based compounds such as tetra-isopropoxytitanium, tetra-n-butoxytitanium, and the like, and aluminum-based compounds such as aluminum isopropylate, and the like. The addition amount is 0.1 to 10 parts by mass and preferably 0.2 to 5 parts by mass relative to 100 parts by mass of the photocurable printing ink of the present invention.

Examples of the antioxidant include phenol-based antioxidants such as 2,6-di-tert-butyl-p-cresol, butylated hydroxyanisole, 2,4,6-tri-tert-butylphenol, 2,2'-methylenebis(4-methyl-6-tert-butylphenol), and the like, and an antioxidant of 2,2,6,6-tetramethylpiperizine derivative referred to as "HALS", phosphorus-based and sulfur-based secondary antioxidants. On the other hand, examples of the polymerization inhibitor include, but are not limited to, nitrosoamine salts and the like. These antioxidants or polymerization inhibitors can be used alone or in combination of two or more. The addition amount of each of the agents is 0.01 to 2.0 parts by mass and preferably 0.03 to 1.0 parts by mass relative to 100 parts by mass of the photocurable composition of the present invention.

Examples of other auxiliaries include those for the purpose of imparting abrasion resistance, a blocking preventing property, a slippage or scratch preventing property, such as paraffin wax, polyethylene wax, polypropylene wax, polytetrafluoroethylene wax, and silicon compounds; and an ultraviolet absorber, an infrared absorber, an antibacterial agent, and the like according to required performance. The amount of the auxiliary added is preferably 0 to 10 parts by mass relative to 100 parts by mass of the whole amount of the composition.

The photocurable printing ink of the present invention may be produced by mixing the components, and the order and method of mixing are not particularly limited. For example, the components can be mixed between room temperature and 100° C. by using a kneading/mixing adjuster such as a kneader, a three-roll mill, a sand mill, a gate mixer, an ultrasonic homogenizer, a high-pressure homogenizer, a paint shaker, a sand grinder, a dyno mill, a disper mat, a beads mill, a SC mill, a nanomizer, or the like. Among these, a kneader, a three-roll mill, or a beads mill is preferably used for production in view of efficient production of an offset ink having high viscosity.

A printed matter can be produced by printing the photocurable printing ink of the present invention on a printing substrate and optically polymerizing and curing the ink. The light used is ultraviolet light, ionizing radiations such as electron beams, α-rays, β-rays, and γ-rays, microwaves, high-frequency waves, visible light, infrared light, laser beams, or the like. Among these, ultraviolet light is preferred.

The ultraviolet light at a wavelength of 180 to 400 nm is effective, and light at a wavelength of 254 nm, 308 nm, 313 nm, or 365 nm is particularly effective for curing the photocurable composition and the photocurable ink composition of the present invention. Examples of a light source include a low-pressure mercury lamp, a high-pressure mercury lamp, an ultrahigh-pressure mercury lamp, a metal halide lamp, a chemical lamp, a black light lamp, a mercury-xenon lamp, an excimer lamp, a short-arc lamp, a helium-cadmium laser, an argon laser, an excimer laser, and a LED lamp.

The amount of ultraviolet irradiation cannot be unconditionally determined because it is affected by the type of the light source used and the amounts of the compound (M) and reaction product, but is preferably within a range of 10 to 2000 J/m$^2$ in view of productivity.

When the photocurable printing ink of the present invention described in detail above is used as an offset ink for multicolor printing, the photocurable printing ink of the present invention may be used as an ink of one of the four-process colors such as yellow, magenta, cyan, and black or may be used for all of the colors. For example, a printed matter is applied to food packaging, the photocurable composition of the present invention is preferably used for all colors in order to minimize migration.

Examples of the printing substrate used in the printed matter of the present invention include, but are not particularly limited to, various types of synthetic paper such as woodfree paper, coated paper, art paper, simili paper, thin paper, cardboard, and the like, films or sheets of polyester resins, acrylic resins, vinyl chloride resins, vinylidene chloride resins, polyvinyl alcohol, polyethylene, polypropylene, polyacrylonitrile, ethylene-vinyl acetate copolymer, ethylene-vinyl alcohol copolymer, ethylene-methacrylic acid copolymer, nylon, polylactic acid, polycarbonate, and the like, cellophane, aluminum foils, and other various substrates having been used as printing substrates.

When used as a cured product produced by curing as described above, for example, used as the photocurable printing ink, the printed matter produced by printing on the substrate contains, as decomposed residues of the novel compound of the present invention represented by the general formula 1, a benzaldehyde compound (2a) represented by structural formula 2a below

[Chem. 74]

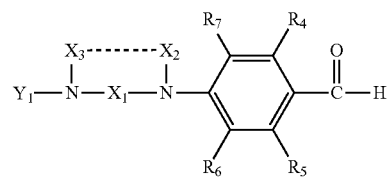

General formula 2a (in the formula, $X_1$, $X_2$, $X_3$, $Y_1$, and $R_4$ to $R_7$ represent the same meanings as in the general formula 1) and an alkyl benzyl ketone compound (2b) represented by structural formula 2b

[Chem. 75]

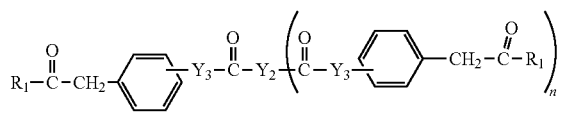

General formula 2b (in the formula, $R_1$, $Y_2$, $Y_3$, and n represent the same meanings as in the general formula 1).

Specifically, the compound represented by the general formula 1 generates radicals by absorption of ultraviolet light and initiates polymerization and contains compounds represented by the general formula 2a and the general formula 2b accompanied with emission of an amine compound [$NHR_2R_3$] as described below.

[Chem. 76]

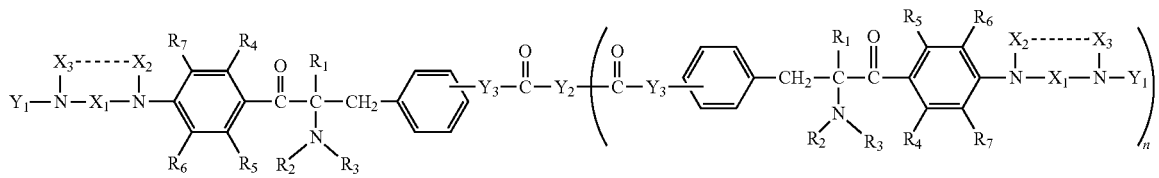

General formula 1

↓ Light irradiation

-continued

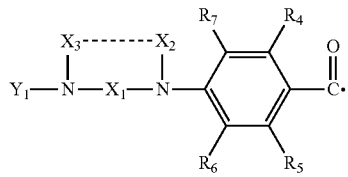
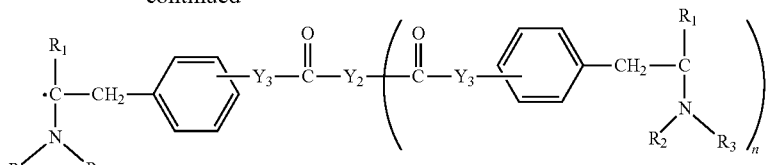

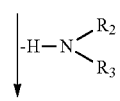

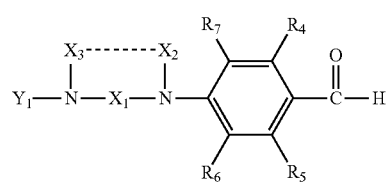

General formula 2a
Benzaldehyde compound (2a)

General formula 2b
Alkyl benzyl ketone compound (2b)

For example, in the case of the compound (M1), radicals are generated by ultraviolet irradiation to initiate polymerization, and byproducts are allowed to remain in the cured product as described below.

[Chem. 77]

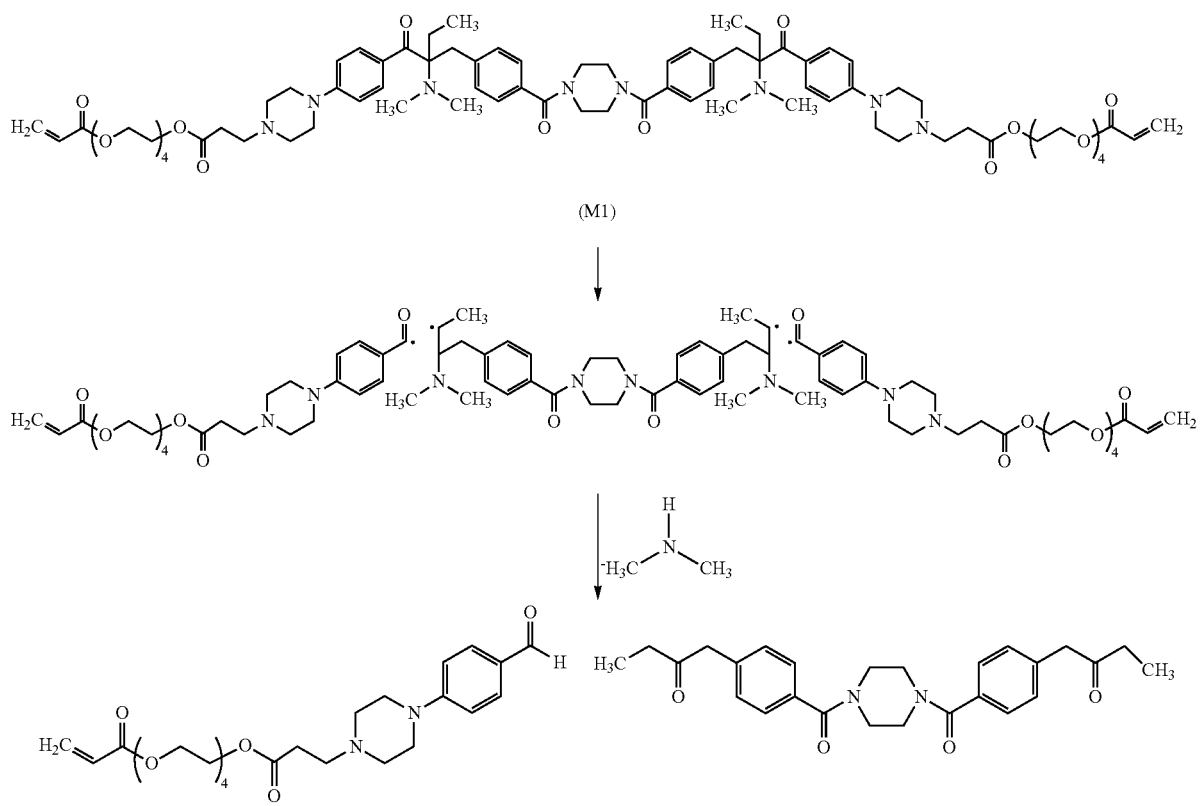

The printed matter of the present invention contains the benzaldehyde compound (2a) and the alkyl benzyl ketone compound (2b) during printing and is characterized in that the migration concentration of the benzaldehyde compound (2a) measured under conditions described below is 50 ppb or less, and the migration concentration of the alkyl benzyl ketone compound (2b) measured under conditions described below is 50 ppb or less.

[Measurement Condition]

Non-printed milk carton white paper is placed so that the back surface thereof is in contact with a cured ink layer uniformly printed on milk carton paper, and is pressed under a press pressure of 40 kg/cm$^2$ in an atmosphere of 25° C. for 48 hours. After pressing, a liquid container with a volume of 1000 ml is formed from the non-printed milk carton white paper, and 1000 ml of an aqueous ethanol solution (mixed solution of 95% by weight of ethanol and 5% by weight of pure water) is poured in the liquid container, which is then closed and allowed to stand in an environment at room temperature of 25° C. for 24 hours. As a result, an ink component migrated to the back surface of the milk carton white paper is extracted in the aqueous ethanol solution.

Then, the aqueous ethanol solution is removed from the liquid container, and the elusion concentration of each of the compound (2a) and the compound (2b) is quantitatively determined as the migration concentration by LC/MS/MS analysis.

Also, when the photocurable composition of the present invention is used as a coating material, in addition to the additives and coloring agent, various additives such as a flowability regulator such as silicone, polyamide, or the like, inorganic fine particles of silica, titanium oxide, zinc oxide, or the like, a silicon-based, fluorine-based, or acrylic leveling agent, an ultraviolet absorber, an anti-sagging agent, a thickener, etc. can be mixed in amounts generally used.

Further, when the photocurable composition of the present invention is used for an ink for ink jet recording not using a plate, it is possible to use the composition containing 0.1 to 30 parts by mass of the pigment, 0 to 20 parts by mass of the binder resin compound, and 40 to 90 parts by mass of (meth)acrylate derivative and/or low-viscosity monomer relative to 100 parts by mass of the total of the photopolymerization initiator and photocurable compound of the present invention. However, from the viewpoint of balance between the color density of the printed matter and ink ejection suitability, the composition preferably contains 0.2 to 20 parts by mass of the pigment, 0 to 10 parts by mass of the binder resin compound, and 50 to 80 parts by mass of acrylate derivative and/or low-viscosity monomer relative to 100 parts by mass of the photocurable composition. The ink for ink jet recording produced as described above is preferably designed so as to have generally 1 to 100 mPa·s (25° C.) depending on the ink jet apparatus used.

Also, when the photocurable ink for ink jet recording is used for multicolor printing, the photocurable composition of the present invention may be used for one of the colors of the inks used, for example, the four-process color inks such as yellow, magenta, cyan, and black, or when a dark color and light color of the same color system are added to each of the colors, the photocurable composition may be used for one of the colors including light-color light magenta and dark-color red in addition to magenta, light-color light cyan and dark-color blue in addition to cyan, and light-color gray or light black and dark-color matte black in addition to black. The composition may be used for all of the colors.

In addition, if required, a surfactant, a leveling additive, a matting agent, a polyester resin, a polyurethane resin, a vinyl resin, an acrylic resin, a rubber resin, or wax for adjusting film physical properties can be added within a range in which ejection stability is not impaired.

EXAMPLES

The present invention is described in further detail below by examples, but the present invention is not limited to these examples.

[$^1$H-NMR Measurement Condition]
Apparatus: FT-NMR manufactured by JEOL Ltd. JNM-LA300 (300 MHz)
Measurement solvent: deuterochloroform (CDCl$_3$-d1)
Internal standard material: tetramethylsilane (TMS)

Example 1: Synthesis of Exemplary Compound (M1)

[Step I]

[Chem. 78]

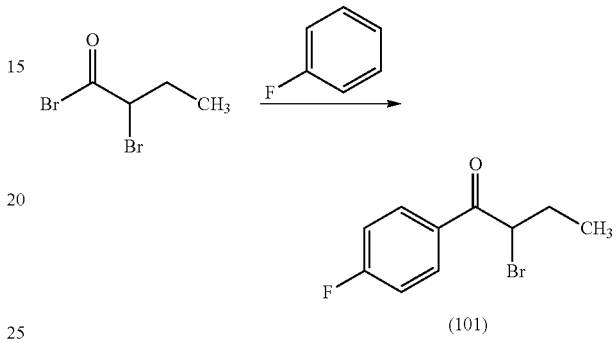

A 1-L flask provided with a stirrer, a thermometer, a nitrogen inlet tube, an alkali trap, and a dropping funnel, 121.8 g of aluminum chloride (anhydrous) and 300 mL of dehydrated dichloromethane were charged and ice-cooled with an ice bath under a nitrogen stream. Then, 200 g of 2-bromobutyryl bromide was added to the resultant mixture. A mixed solution of 83.6 g fluorobenzene and 100 mL of dehydrated dichloromethane was added dropwisely to the flask over 20 minutes by using the dropping funnel. After the addition, the ice bath was removed, and in this state, the mixture was continuously stirred for 2 hours.

After the completion of stirring, the reaction solution was poured into 1 L of ice water and continuously stirred for 2 hours. After standing, the reaction solution was separated into liquids, and a lower layer was recovered. The lower layer was washed twice with 2N hydrochloric acid, washed once with an aqueous saturated sodium hydrogen carbonate solution, and then washed twice with saturated saline. The residue was dried with magnesium sulfate for 24 hours, and then dichloromethane was distilled off under reduced pressure to produce 2-bromo-1-(4-fluorophenyl)-1-butanone (101).

Yield amount: 214.3 g, yield: 100% by mass

[Step II]

[Chem. 79]

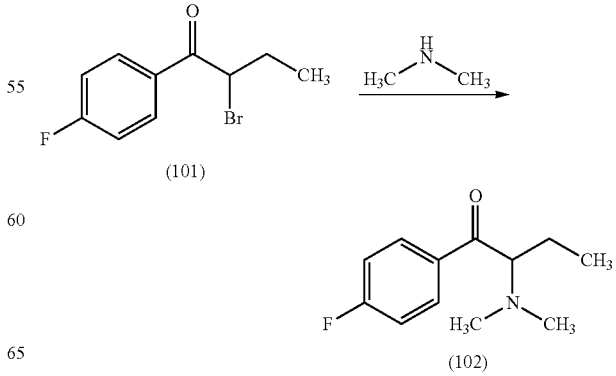

In a 2-L flask provided with a stirrer and a thermometer, 157.7 g of the intermediate (101) and 750 mL of methyl ethyl ketone were charged and ice-cooled by using an ice bath. Then, 174 g of a 50 mass % aqueous dimethylamine solution was added dropwisely to the flask over 30 minutes by using the dropping funnel. After the completion of addition, the ice bath was removed, and in this state, the mixture was continuously stirred for 24 hours. After disappearance of the intermediate (1010) was confirmed by thin-layer chromatography, methyl ethyl ketone and dimethyl amine were distilled off under reduced pressure, and toluene was poured into the residue. The resultant mixture was washed twice with water and further washed once with saturated saline, and then an upper layer was recovered and dried with magnesium sulfate for 24 hours. Then, toluene was distilled off under reduced pressure to produce intermediate (102).

Yield amount: 133.3 g, yield: 99% by mass
[Step III]

[Chem. 80]

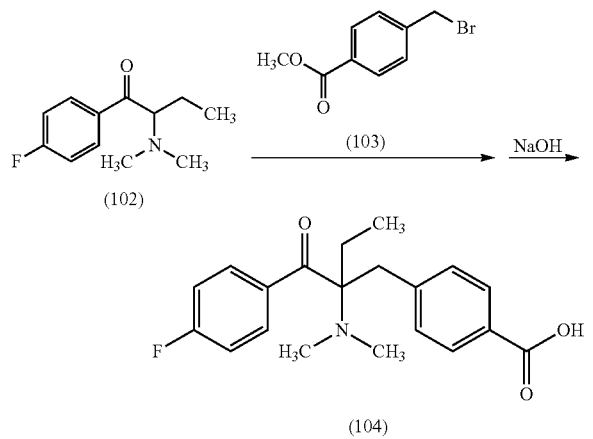

In a 500-mL flask provided with a stirrer, a thermometer, and a condenser, 79.5 g of the intermediate (102), 87.0 g of methyl 4-(bromomethyl)benzoate (103), and 120 mL of IPA were charged and stirred at 50° C. for 24 hours. Then, 105 mL of a 8M aqueous sodium hydroxide solution was added to the resultant mixture and stirred at 50° C. for 1 hour. After the completion of stirring, IPA was distilled off, and the residue was adjusted to pH 5.5 by using 12N hydrochloric acid and then extracted with ethyl acetate. Then, hexane was added to the extract, and the precipitated crystal was separated by filtration to produce an intermediate (104).

Yield amount: 94.5 g, yield: 65.5% by mass
[Step IV]

[Chem. 81]

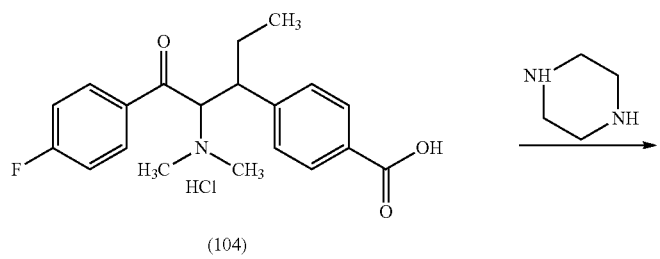

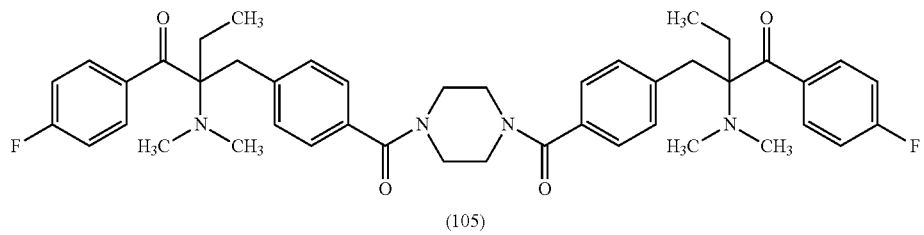

(105)

In a 1000-mL flask provided with a stirrer, a thermometer, and a dropping funnel, 35.0 g of 2-chloro-4,6-dimethoxy-1,3,5-triazine and 400 mL of dehydrated dichloromethane were charged and ice-cooled by using an ice bath. Then, 80.8 g of N-methylmorpholine was added dropwisely to the flask over 10 minutes by using the dropping funnel. After the completion of addition, 76.0 g of the intermediate (104) was added and stirred for 1 hour under ice cooling. Then, 200 mL of dehydrated dichloromethane dissolving 9.5 g of piperazine was added dropwisely to the mixture over 20 minutes by using the dropping funnel. The ice bath was removed, and stirring was continued at room temperature for 1 hour. After the completion of reaction was confirmed by thin-layer chromatography, the reaction was terminated by adding water. The reaction product was transferred to a separatory funnel, and an organic layer as a lower layer was recovered. Further, the organic layer was washed twice with distilled water and then dried with magnesium sulfate for 24 hours. Then, dichloromethane was distilled off under reduced pressure, and the resultant crude product was recrystallized with ethanol to produce an intermediate (105).

Yield amount: 57.5 g, yield: 78.0% by mass

[Step V]

[Chem. 82]

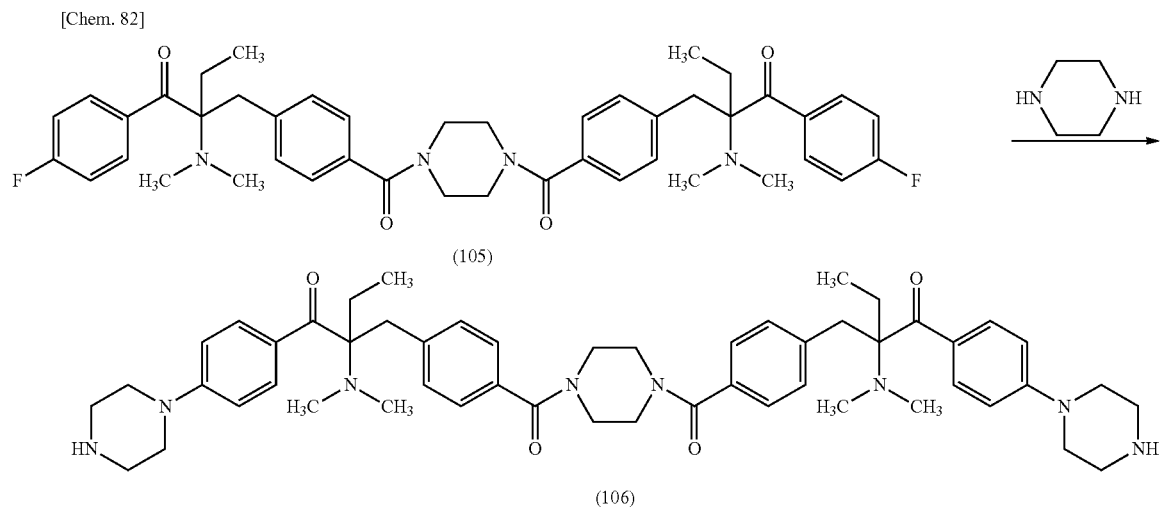

In a 500-mL flask provided with a stirrer, a thermometer, and a condenser, 38.0 g of the intermediate (105), 22.2 g of piperazine, and 120 mL of dimethylsulfoxide (DMSO) were charged and stirred at 100° C. for 40 hours. After the completion of reaction, distilled water and methylene chloride were added, and a methylene chloride layer was washed with water three times and washed with saturated saline one time and dried with magnesium sulfate for 24 hours. Then, dichloromethane was distilled off under reduced pressure to produce an intermediate (106).

Yield amount: 43.9 g, yield: 98.0% by mass

[Step VI]

Figure 3:
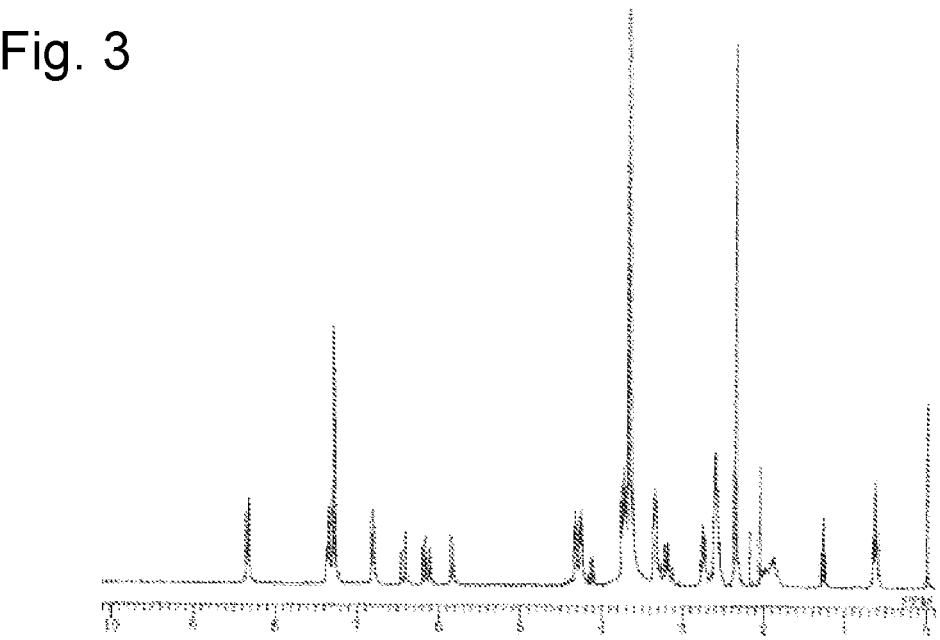
FIG. 3 is a ¹H-NMR chart of a compound M1 produced in Example 1.

In a 300-mL flask provided with a stirrer, a condenser, and a thermometer, 30.3 g of tetraethylene glycol diacrylate ("Light Acrylate 4EG-A" manufactured by Kyoeisha Chemical Co., Ltd.), 17.4 g of the intermediate (106), and 100 mL of ethanol were added and stirred at room temperature for 24 hours. The solvent was distilled off by concentration under reduced pressure, and the resultant reaction mixture was purified by silica gel chromatography to produce a photopolymerization initiator (M1) of the present invention. FIG. 3 shows a $^1$H-NMR chart of the photopolymerization initiator (M1).

Yield amount: 22.0 g, yield: 91.0% by mass

[Chem. 83]

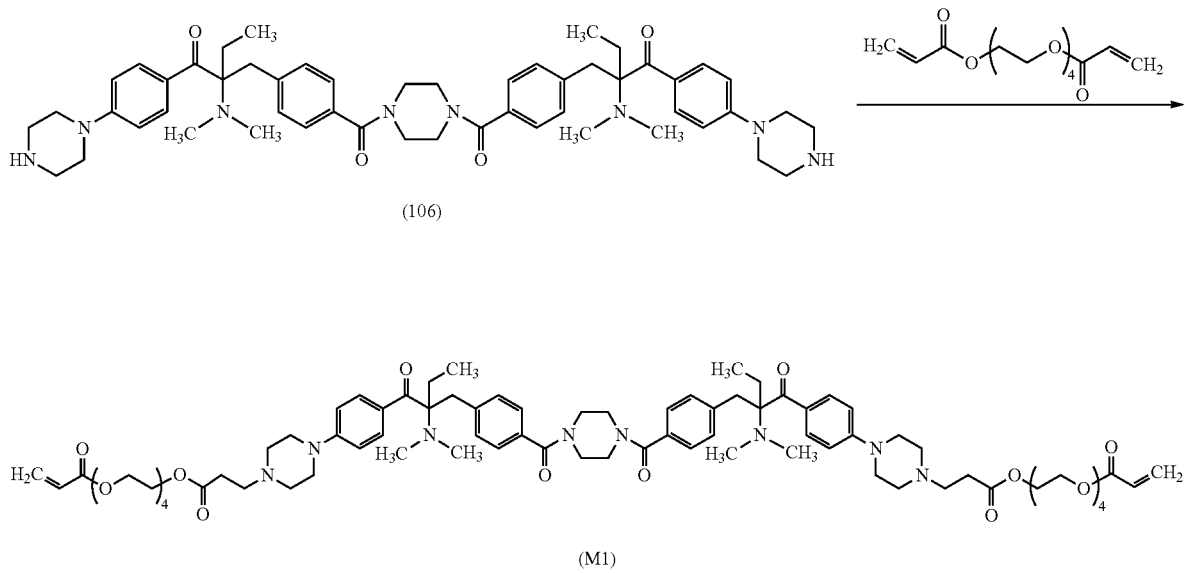

Example 2: Synthesis of Exemplary Compound (M4)

[Chem. 84]

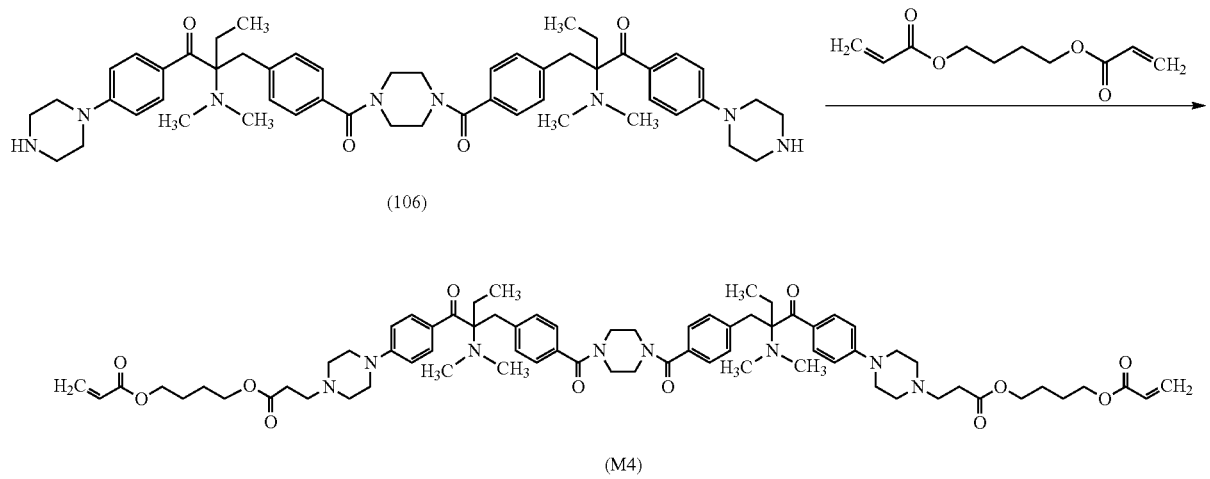

Figure 4:
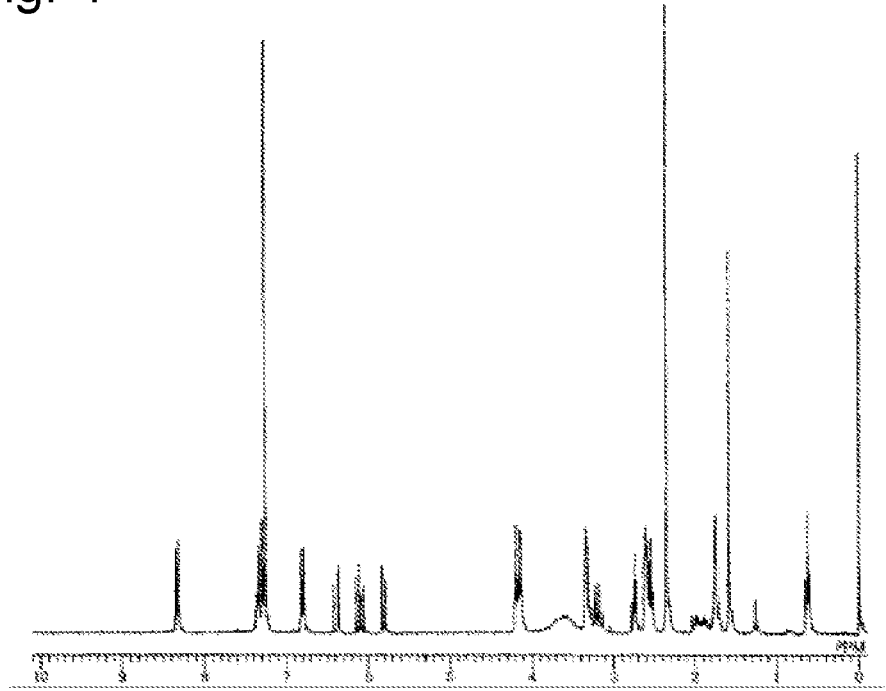
FIG. 4 is a ¹H-NMR chart of a compound M4 produced in Example 2.

A photopolymerization initiator (M4) of the present invention was produced according to the method described in Example 1 except that in [Step VI] of Example 1, 19.8 g of butanediol diacrylate ("Viscoat #195" manufactured by Osaka Organic Chemical Industry Ltd.) was used in place of tetraethylene glycol diacrylate relative to 17.4 g of the intermediate (106) produced in [Step V] of Example 1. FIG. 4 shows a $^1$H-NMR chart of the photopolymerization initiator (M4).

Yield amount: 23.0 g, yield: 90.9% by mass

Example 3: Synthesis of Exemplary Compound (M7)

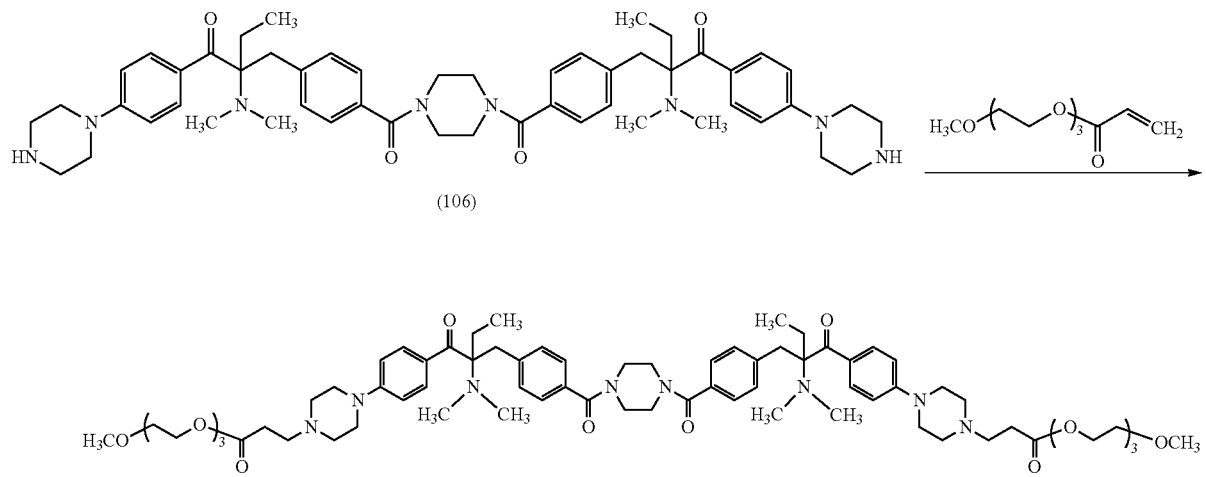

A photopolymerization initiator (M7) of the present invention was produced according to the method described in Example 1 except that in [Step VI] of Example 1, 21.8 g of methoxytriethylene glycol acrylate ("Viscoat #MTG" manufactured by Osaka Organic Chemical Industry Ltd.) was used in place of tetraethylene glycol diacrylate relative to 17.4 g of the intermediate (106) produced in [Step V] of Example 1.

Yield amount: 26.5 g, yield: 95.0% by mass

Example 4: Synthesis of Exemplary Compound (M14)

[Step I]

[Chem. 85]

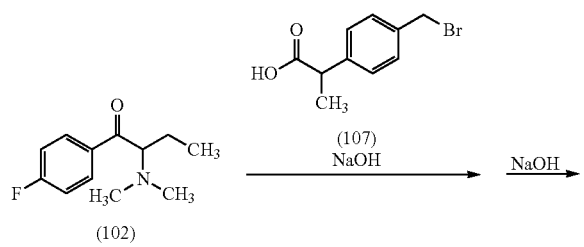

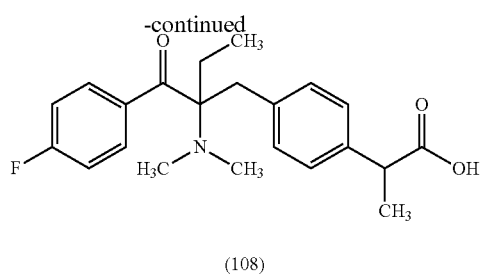

(108)

A 500-mL flask provided with a stirrer, a thermometer, a condenser, 41.9 g of the intermediate (102) produced in [Step II] of Example 1, 53.5 g of 2-[4-(bromomethyl)phenyl]propionic acid (107), and 100 mL of IPA were charged, 27.5 mL of a 8M aqueous sodium hydroxide solution was added at room temperature, and further the resultant mixture was stirred at 50° C. for 2 hours to form a quaternary ammonium salt. Then, 41 mL of a 8M aqueous sodium hydroxide solution was added and stirred at 50° C. for 1 hour. After the completion of stirring, IPA was distilled off, and the residue was adjusted to pH 5.5 by using 6N hydrochloric acid and then extracted with toluene. The extract was washed with water, and the solvent was distilled off under reduced pressure. The resultant crude reaction product was purified by silica gel chromatography to produce an intermediate (108).

Yield amount: 39.0 g, yield: 52.5% by mass

[Step II]

[Chem. 86]

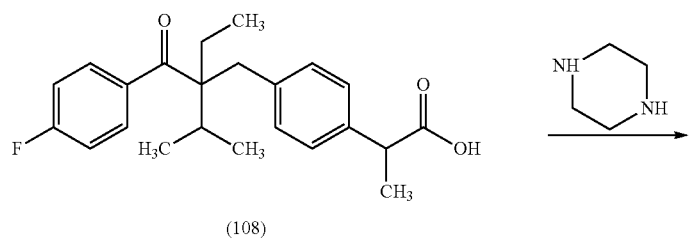

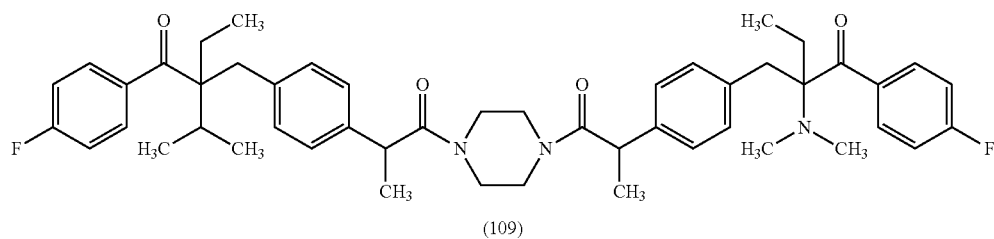

In a 500-mL flask provided with a stirrer, a thermometer, and a dropping funnel, 19.0 g of the intermediate (108), 80 mL of dichloromethane, and 0.5 mL of N,N-dimethylformamide were charged, and 6.7 g of thionyl chloride was slowly added dropwisely to the resultant mixture, followed by stirring for 30 minutes. Then, 50 mL of a dehydrated dichloromethane solution dissolving 2.2 g of piperazine was added dropwisely to the flask by using the dropping funnel. Then, 11.4 g of triethylamine was added dropwisely and stirred at room temperature for 1 hour. After the completion of reaction was confirmed by thin-layer chromatography, the reaction was terminated by adding water. The reaction product was transferred to a separatory funnel, and an organic layer as a lower layer was recovered. The organic layer was further washed with distilled water two times and then dried with magnesium sulfate for 24 hours. Dichloromethane was distilled off under reduced pressure, and the resultant crude product was recrystallized with ethanol to produce an intermediate (109).

Yield amount: 17.2 g, yield: 85.0% by mass

[Step III]

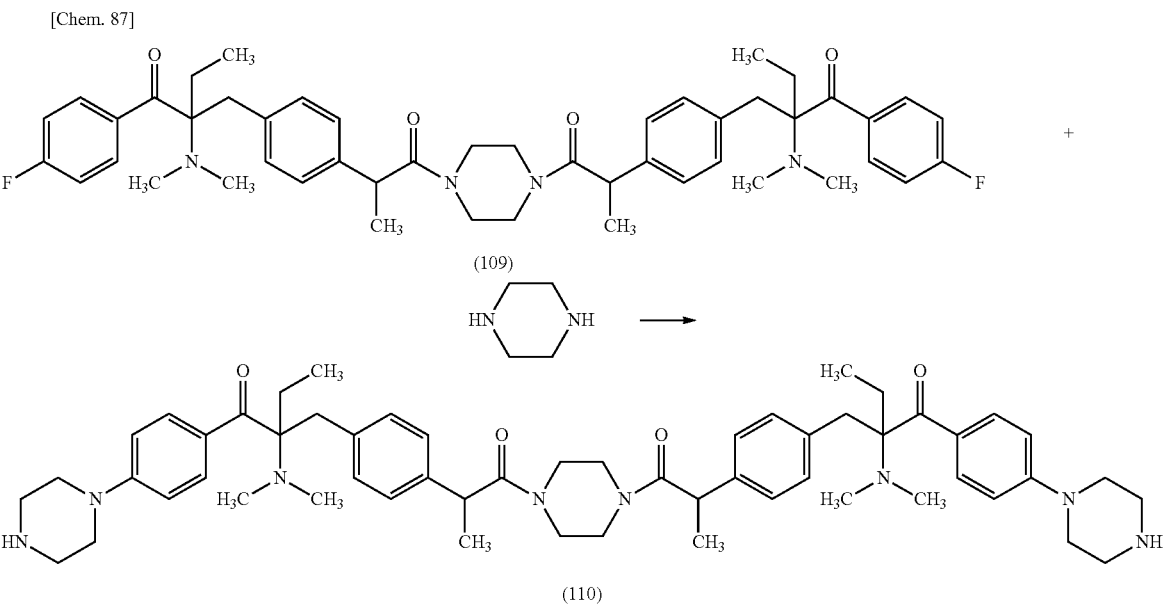

In a 300-mL flask provided with a stirrer, a thermometer, and a condenser, 14.8 g of the intermediate (109), 8.6 g of piperazine, 5.5 g of anhydrous potassium carbonate, and 30 mL of dimethylsulfoxide (DMSO) were charged and stirred at 100° C. for 24 hours. After the completion of reaction, distilled water and methylene chloride were added, and a methylene chloride layer was washed with water three times, washed with saturated saline one time, and dried with magnesium sulfate for 24 hours. Then, dichloromethane was distilled off under reduced pressure to produce an intermediate (110).

Yield amount: 18.0 g, yield: 97.5% by mass

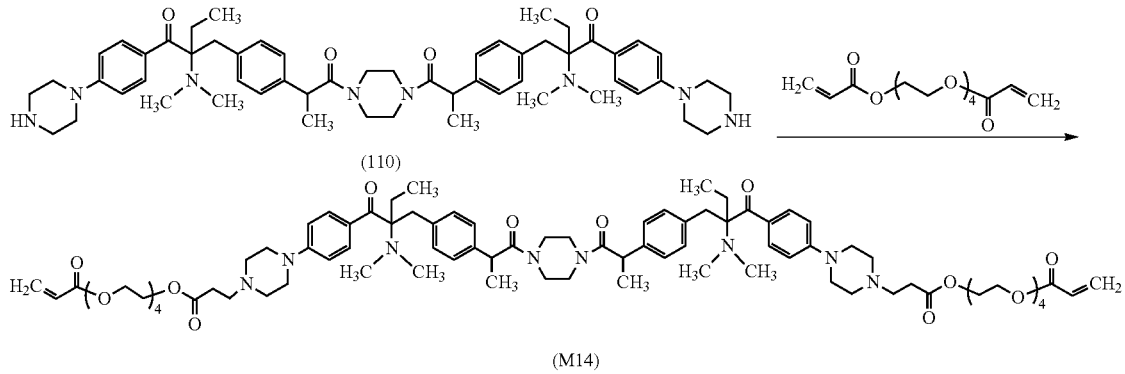

[Step IV]

In a 300-mL flask provided with a stirrer, a condenser, and a thermometer, 15.5 g of tetraethylene glycol diacrylate ("Light Acrylate 4EG-A" manufactured by Kyoeisha Chemical Co., Ltd.), 15.5 g of the intermediate (110), and 100 mL of ethanol were added and stirred at room temperature for 24 hours. The solvent was distilled off by concentration under reduced pressure, and the resultant reaction mixture was purified by silica gel chromatography to produce a photopolymerization initiator (M14) of the present invention.

Yield amount: 25.1 g, yield: 96.3% by mass

Example 5: Synthesis of Exemplary Compound (M23)

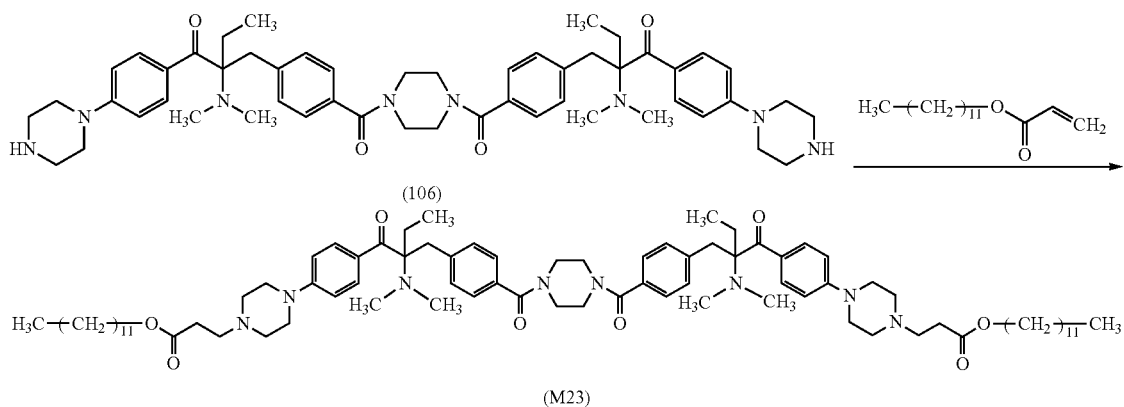

A photopolymerization initiator (M23) of the present invention was produced according to the method described in Example 1 except that in Step V of Example 1, 16.8 g of dodecyl acrylate (LA manufactured by Osaka Organic Chemical Industry Ltd.) was used in place of tetraethylene glycol diacrylate relative to 17.4 g of the intermediate (106) produced in Step V of Example 1.

Yield amount: 22.1 g, yield: 93.8% by mass

Example 6: Synthesis of Exemplary Compound (M28)

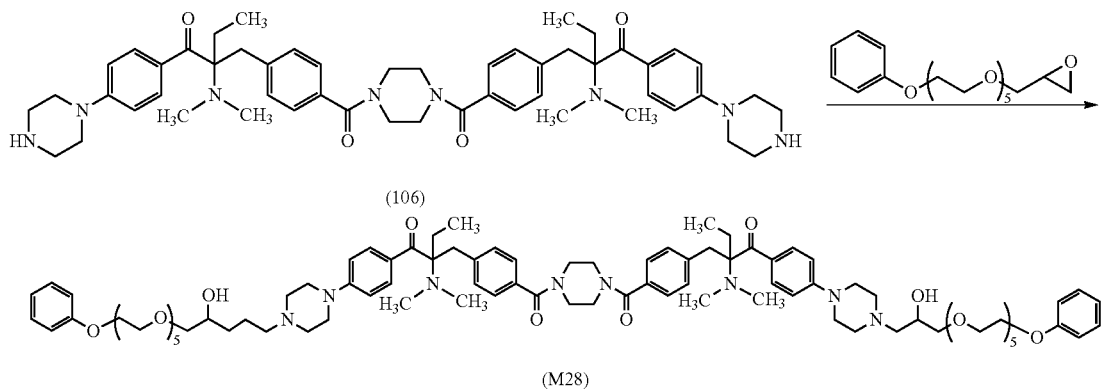

In a 200-mL flask provided with a stirrer, a condenser, and a thermometer, 13.0 of the intermediate (106) produced in Step V of Example 1, 13.9 g of ethylene oxide-modified phenyl glycidyl ether ("EX-145" manufactured by Nagase Chemtex Corporation), and 60 mL of toluene were added and reacted by heating under reflux for 6 hours. After cooling to room temperature, toluene was distilled off under reduced pressure, and the resultant reaction mixture was purified by silica gel chromatography to produce a photopolymerization initiator (M28) of the present invention.

Yield amount: 20.9 g, yield: 86.5% by mass

Example 7: Synthesis of Exemplary Compound (M31)

[Chem. 91]

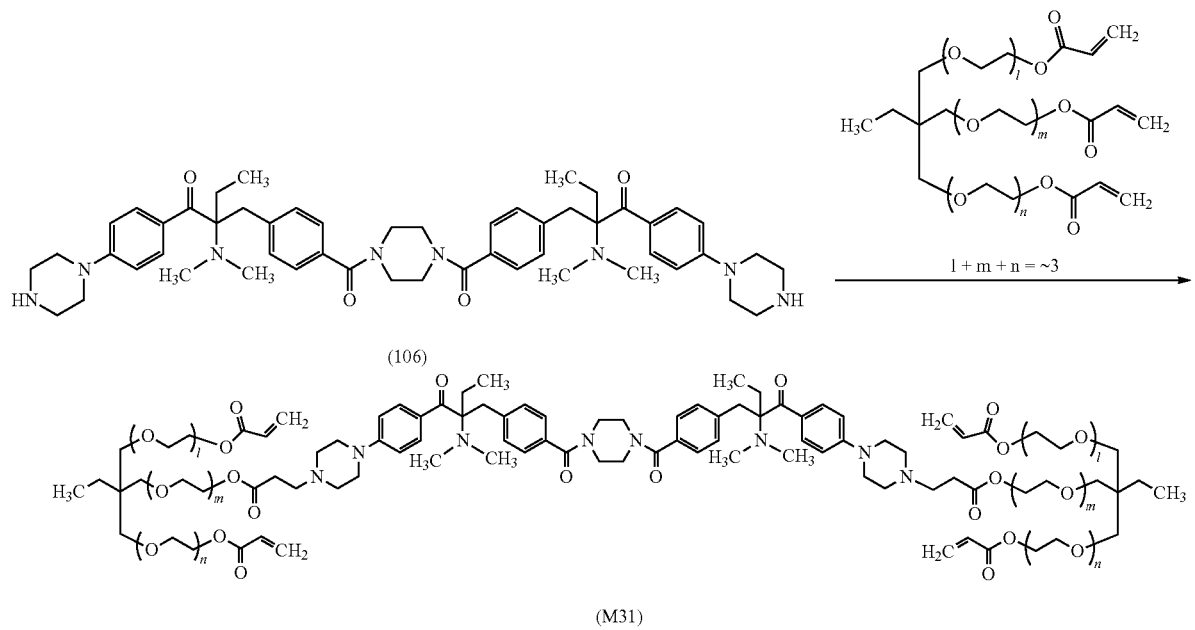

Figure 5:
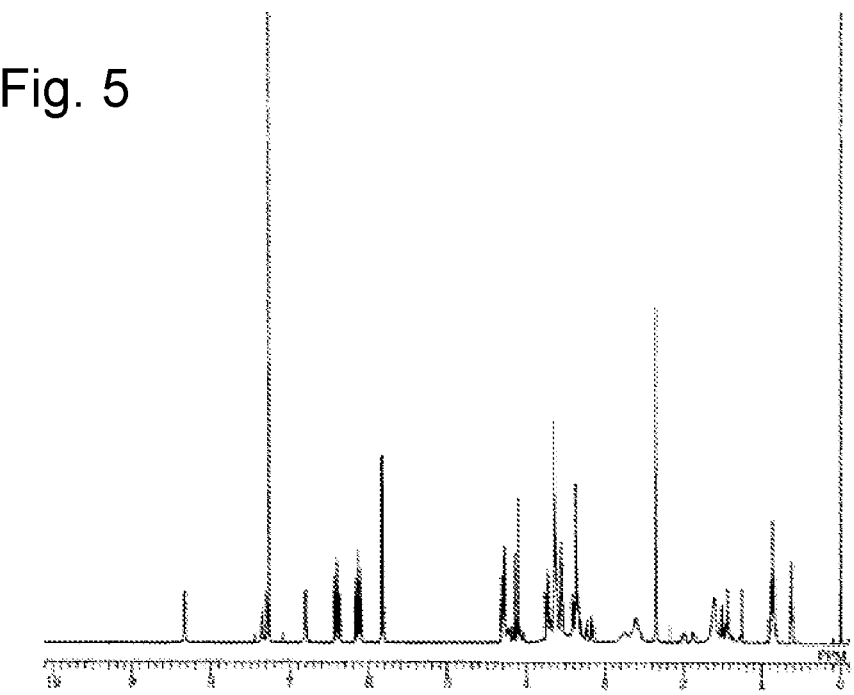
FIG. 5 is a ¹H-NMR chart of a compound M31 produced in Example 7.

In a 300-mL flask provided with a stirrer, a condenser, and a thermometer, 17.4 of the intermediate (106) produced in Step V of Example 1, 25.7 g of ethylene oxide-modified trimethylolpropane triacrylate (M3130 manufactured by MIWON Chemical Co., Ltd.), 43 mg of p-methoxyphenol, and 150 mL of ethanol were added and stirred at 50° C. for 24 hours. Then, the solvent was distilled off under reduced pressure to produce a photopolymerization initiator (M31) of the present invention. FIG. 5 shows a $^1$H-NMR chart of the photopolymerization initiator (M31).

Yield amount: 42.7 g, yield: 99.0% by mass

Example 8: Synthesis of Exemplary Compound (M32)

[Chem. 92]

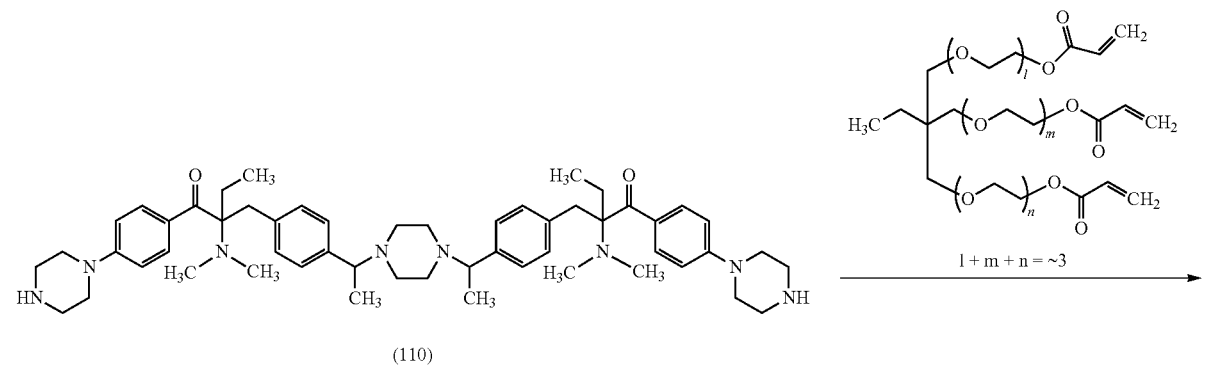

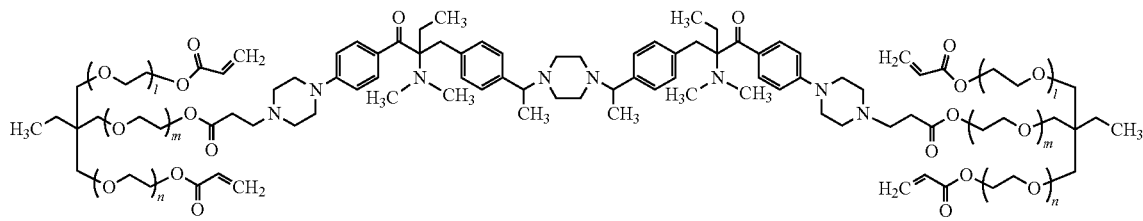

(M32)

Figure 6:
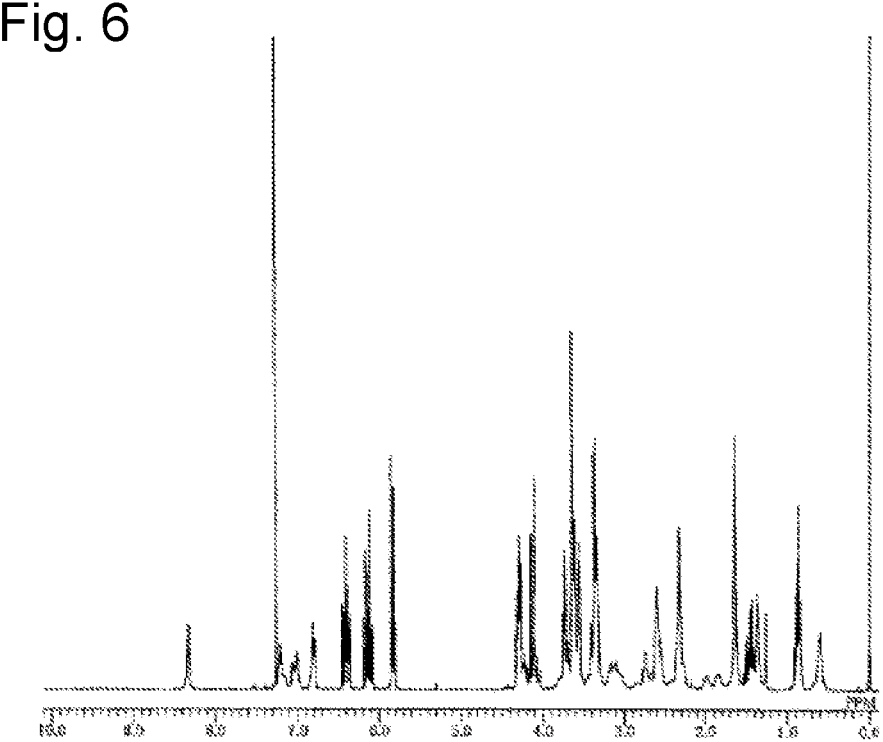
FIG. 6 is a ¹H-NMR chart of a compound M32 produced in Example 8.

In a 300-mL flask provided with a stirrer, a condenser, and a thermometer, 18.5 of the intermediate (110) produced in Step III of Example 4, 25.7 g of ethylene oxide-modified trimethylolpropane triacrylate (M3130 manufactured by MIWON Chemical Co., Ltd.), 44 mg of p-methoxyphenol, and 150 mL of ethanol were added and stirred at 50° C. for 24 hours. Then, the solvent was distilled off under reduced pressure to produce a photopolymerization initiator (M32) of the present invention. FIG. 6 shows a $^1$H-NMR chart of the photopolymerization initiator (M32).

Yield amount: 43.4 g, yield: 98.3% by mass

Example 9: Synthesis of Exemplary Compound (M4.1)

A photopolymerization initiator (M41) of the present invention was produced according to the method described in Example 1 except that in [Step V] of Example 1, 29.4 g of 2,5-dimethylpiperazine was used in place of 22.2 g of piperazine.

Example 10: Synthesis of Exemplary Compound (M43)

A photopolymerization initiator (M43) of the present invention was produced according to the method described in Example 1 except that in [Step II] of Example 1, 256.6 g of methyldodecylamine was used in place of 174 g of a 50 mass % aqueous dimethylamine solution.

Example 11: Synthesis of Exemplary Compound (M45)

[Step I]

[Chem. 93]

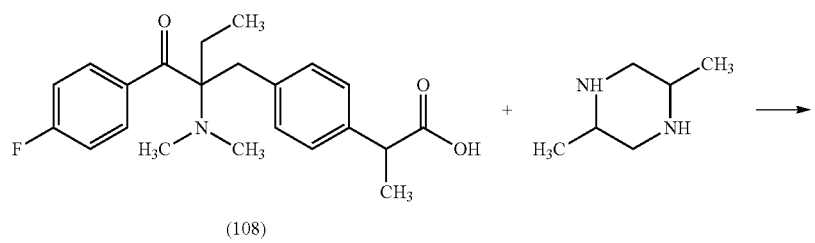

(108)

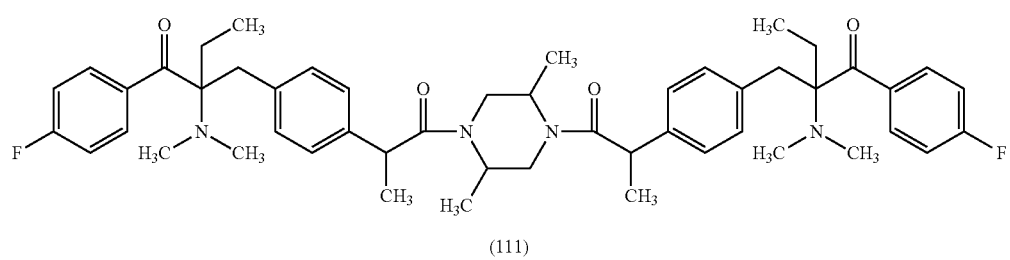

(111)

In Step II of Example 4, 2.92 g of 2,5-dimethylpiperazine was used in place of 2.2 g of piperazine to produce an intermediate (111).

Yield amount: 21.0 g, yield: 79.0% by mass

[Step II]

[Chem. 94]

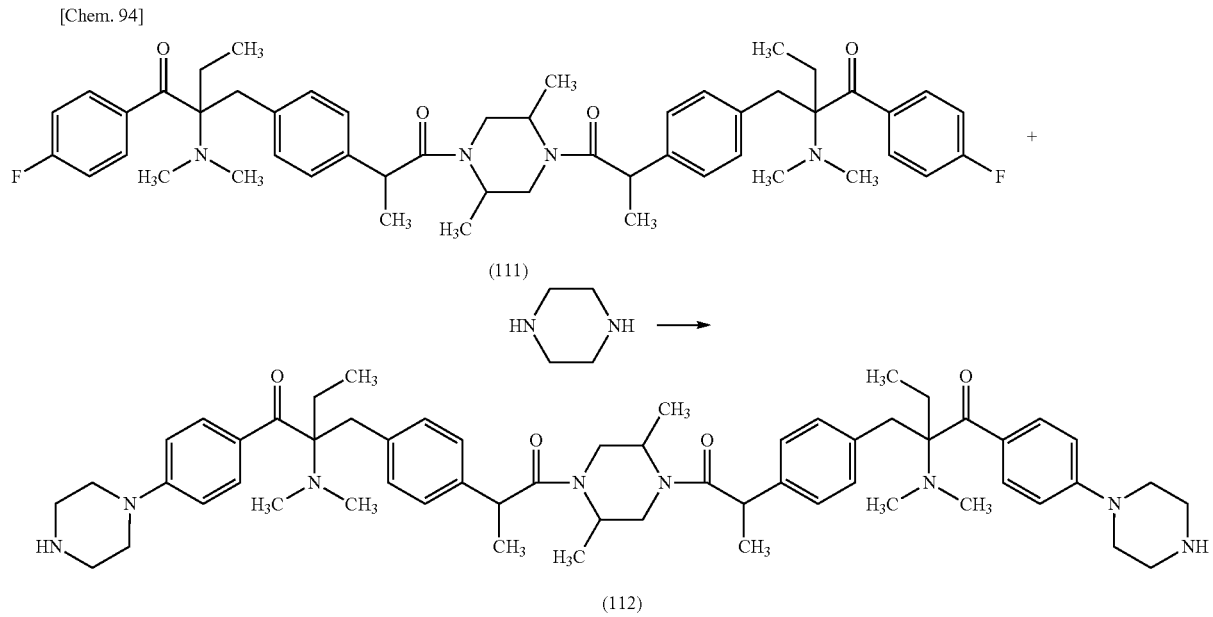

In a 300-mL flask provided with a stirrer, a thermometer, and a condenser, 16.4 g of the intermediate (111), 8.6 g of piperazine, 5.5 g of anhydrous potassium carbonate, and 30 mL of dimethylsulfoxide (DMSO) were charged and stirred at 100° C. for 24 hours. After the completion of reaction, distilled water and methylene chloride were added, and a methylene chloride layer was washed with water three time, washed with saturated saline one time, and then dried with magnesium sulfate for 24 hours. Dichloromethane was distilled off under reduced pressure to produce an intermediate (112).

Yield amount: 18.3 g, yield: 95.8% by mass

[Step III]

[Chem. 95]

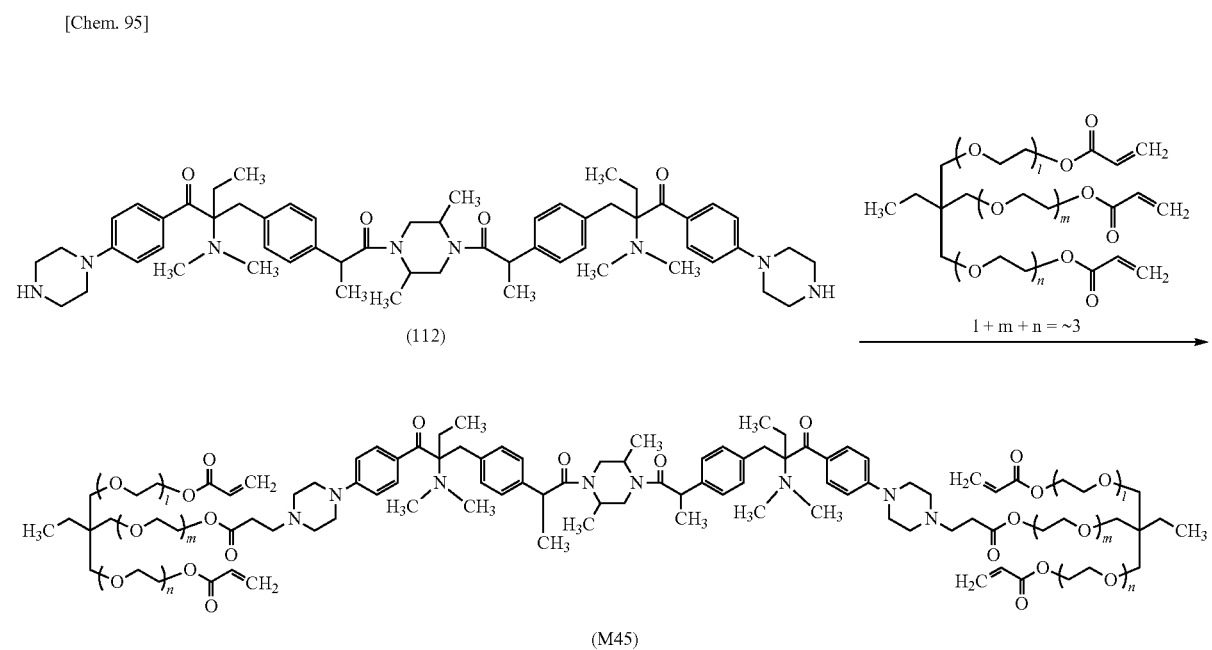

In a 300-mL flask provided with a stirrer, a condenser, and a thermometer, 14.3 g of the intermediate (112), 19.3 g of ethylene oxide-modified trimethylolpropane triacrylate ("M3130" manufactured by MIWON Chemical Co., Ltd.), 34 mg of p-methoxyphenol, and 100 mL of ethanol were added and stirred at 50° C. for 24 hours. The solvent was distilled off under reduced pressure to produce a photopolymerization initiator (M45) of the present invention.

Yield amount: 32.5 g, yield: 96.8% by mass

Example 12: Synthesis of Exemplary Compound (M50)

Figure 7:
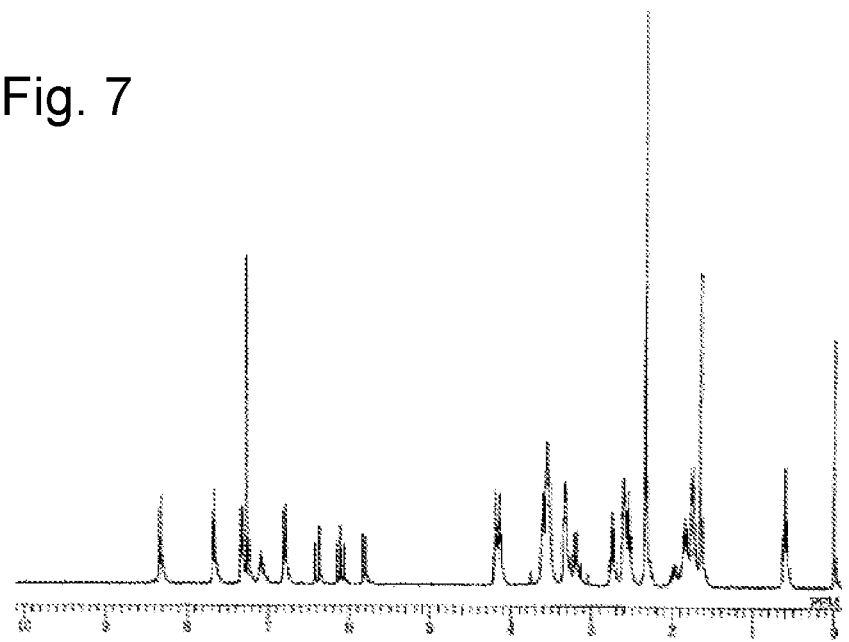
FIG. 7 is a ¹H-NMR chart of a compound M50 produced in Example 12.

A photopolymerization initiator (M50) of the present invention was produced according to the method described in Example 1 except that in synthesis in [Step IV] of Example 1, diethylene glycol bis(3-aminopropyl) ether was used in place of piperazine, and butanediol diacrylate was used in place of ethylene glycol diacrylate. FIG. 7 shows a $^1$H-NMR chart of the photopolymerization initiator (M50).

Example 13: Synthesis of Exemplary Compound (M55)

A photopolymerization initiator (M55) of the present invention was produced according to the method described in Example 4 except that in synthesis in [Step II] of Example 4, 2.97 g of 1,6-diaminohexane was used in place of 2.2 g of piperazine.

Example 14: Synthesis of Exemplary Compound (M64)

Figure 8:
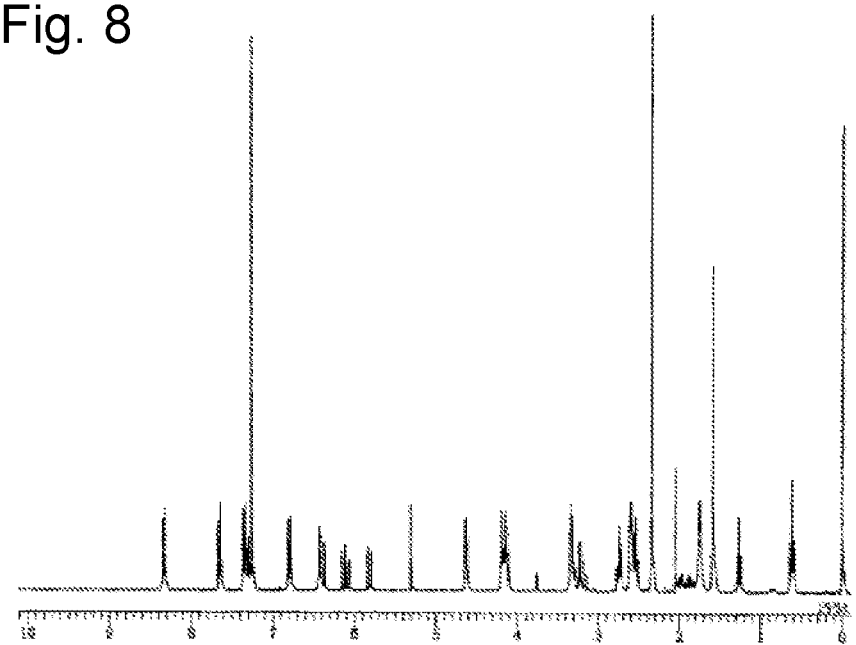
FIG. 8 is a ¹H-NMR chart of a compound M64 produced in Example 14.

A photopolymerization initiator (M64) of the present invention was produced according to the method described in Example 1 except that in [Step IV] of Example 1, 15.1 g of m-xylenediamine was used in place of 9.5 g of piperazine. FIG. 8 shows a $^1$H-NMR chart of the photopolymerization initiator (M64).

Example 15: Synthesis of Exemplary Compound (M78)

A photopolymerization initiator (M78) of the present invention was produced according to the method described in Example 1 except that in [Step IV] of Example 1, 15.1 g of polyethylene glycol (molecular weight 200) was used in place of 9.5 g of piperazine, and 13.5 g of N,N-dimethylaminopyridine was used as a catalyst.

Production Example 1 (Synthesis of Urethane Acrylate Resin)

In a four-neck flask provided with a stirrer, a gas inlet tube, a condenser, and a thermometer, in a first step, 59.4 parts by mass of polymethylene polyphenyl polyisocyanate ("Millionate MR-400" manufactured by Nippon Polyurethane Industry Co., Ltd., dinuclear component 29% by mass, tri-nuclear or higher-nuclear component 71% by mass), 0.1 parts by mass of tertiary butyl hydroxytoluene, 0.02 parts by mass of methoxyhydroquinone, and 0.02 parts by mass of zinc octylate were added and heated to 75° C., and 37.3 parts by mass of 2-hydroxyethyl acrylate was added dropwisely over 1 hour under stirring. After the completion of addition, reaction was performed at 75° C. for 3 hours and then, in second step, 3.3 parts by mass of glycerin was added and further reacted at 75° C. The reaction was performed until an infrared absorption spectrum at 2250 cm$^{-1}$ showing an isocyanate group disappeared, thereby producing a urethane acrylate resin having an acryloyl group concentration of 3.22 mmol/g and a weight-average molecular weight (Mw) of 5438.

Examples 16 to 30 and Comparative Examples 1 and 2

[Method for Producing Photocurable Printing Ink]

Raw materials were mixed according to each of the compositions shown in Table 1, uniformly stirred by using a mixer, and then kneaded by a three-roll mill to produce a base ink for printing ink.

Then, the base ink was mixed with each of the photopolymerization initiators produced in Examples 1 to 37 and Comparative Example 1 or other commercial photopolymerization initiators according to each of the compositions shown in Table 2 to Table 8. The resultant mixture was uniformly stirred by using a mixer and then again kneaded by a three-roll mill to produce a photocurable printing ink of each of the examples and comparative examples.

[Method for Producing Photocurable Printing Ink Printed Matter]

The photocurable printing ink produced as described above was uniformly spread on a rubber roll and a metal roll of a RI tester using a simple coloring device (RI tester, manufactured by Hoei Seikosha Co., Ltd.) and 0.10 ml of the ink, and a printed matter was produced by uniformly applying the ink on the surface of milk carton paper (polyethylene laminate paper) so that the indigo concentration (measured by "SpectroEye" densitometer manufactured by X-Rite Inc.) was 1.6. The RI tester is a tester which applies an ink on paper or a film, and is capable of adjusting the amount of ink transferred and printing pressure.

[Method for Curing Photocurable Printing Ink Using UV Lamp Light Source]

After the photocurable printing ink was applied, the printed matter was irradiated with ultraviolet light (UV), and an ink film was cured ad dried. A UV irradiation apparatus (manufactured by Eye Graphics Co., Ltd., with a cold mirror as an accessory) provided with a water-cooled metal halide lamp (output 100 W/cm one lamp) and a belt conveyor was used. The printed matter was placed on the conveyor and passed immediately below the lamp (irradiation distance, 11 cm) under predetermined conditions described below. The amount of ultraviolet irradiation under each of the conditions was measured by using an accumulated ultraviolet meter (UNIMETR UIT-150-A/receiver UVD-C365 manufactured by Ushio Inc.).

[Method for Evaluating Photocurable Printing Ink Composition: Curability]

Curability was evaluated by confirming the presence of scratch on a surface of the printed matter by a claw scratch method immediately after the printed matter after ink application was irradiated with light using the UV irradiation apparatus. The printed matter was irradiated with ultraviolet light while the conveyor speed (m/min) of the UV irradiation apparatus was changed, and the highest conveyor speed which caused no scratch was described. Therefore, the higher the conveyor speed, the better the dry properties of the ink.

[Method for Evaluating Photocurable Printing Ink Printed Matter: Low Migration Property]

The low migration property was evaluated according to the basic evaluation procedures of the guideline (EuPIA Guideline on Printing Inks, applied to the non-food contact surface of food packaging materials and articles, November 2011 (Replaces the September 2009 version) of EuPIA (European Printing Ink Association).

Figure 2:
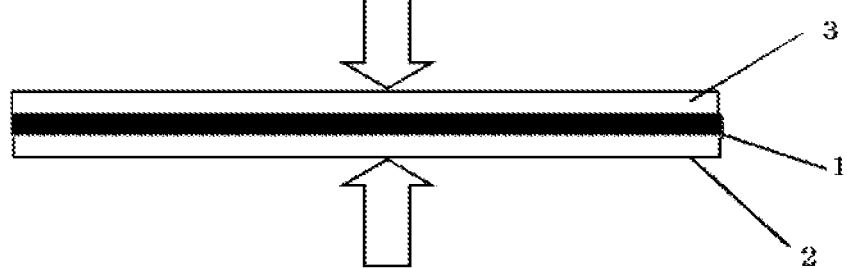
FIG. 2 is a drawing showing milk carton white paper placed so that the back surface thereof is in contact with the upper surface of a printed matter after ultraviolet irradiation and pressed in a direction shown by arrows.

First, the ink layer was dried by two times of UV irradiation of the printed matter at a conveyor speed of 40 m/min. The accumulated amount of ultraviolet light under the conditions was about 120 mJ/cm$^2$. Then, milk carton white paper (hereinafter, non-printed milk carton paper not colored with a ink is referred to as "milk carton white paper") was placed on the cured ink layer on the upper surface of the printed matter so that the back surface of the milk carton white paper was in contact with the cured ink layer, and the milk carton white paper was pressed in an atmosphere of room temperature 25° C. for 48 hours under a press pressure of 40 kg/cm$^2$ by using a hydraulic press machine, thereby transferring (migration) an unreacted component in the cured ink layer to the back surface of the milk carton white paper (refer to FIGS. 1 and 2). After pressing, the milk carton white paper was removed and formed into a liquid container with a volume of 1000 ml. In the liquid container, the back surface to which the ink component had been migrated faced the inside.

Next, 1000 ml of an aqueous ethanol solution (mixed solution containing 95% by weight of ethanol and 5% by weight of pure water) prepared as a pseudo liquid food was poured into the liquid container and closed therein. Under the conditions, the total area of the liquid container inner surface in contact with 1000 ml of the aqueous ethanol solution was about 600 cm$^2$. The closed liquid container was allowed to stand in an atmosphere of room temperature 25° C. for 24 hours, and the ink component transferred to the back surface of the milk carton white paper was extracted with the aqueous ethanol solution.

Then, the aqueous ethanol solution was taken out from the liquid container, and liquid chromatography/mass spectrometry was performed to identify the initiator used and the decomposed products thereof and to quantitatively determine each of the elusion concentrations (migration concentrations).

An ethanol solution of each of the compound M1, the compound M4, the compound M7, the compound M14, the compound M23, the compound M28, the compound M31, the compound M32, the compound M41, the compound M43, the compound M45, the compound M50, the compound M55, the compound M64, and the compound M79 was prepared as a standard sample. Also, a compound having the same molecular structure as each of the benzaldehyde compound (2a) and the benzaldehyde compound (2a), which are decomposed products of each of the compounds, was synthesized, and an ethanol solution thereof was prepared as a standard sample. These standard samples were used for identification, and a calibration curve was previously formed for calculating the elusion concentrations.

For example, in the case of the compound (M1), the benzaldehyde compound (2a) and the benzaldehyde compound (2a) as the decomposed products are as follows.

[Chem. 96]

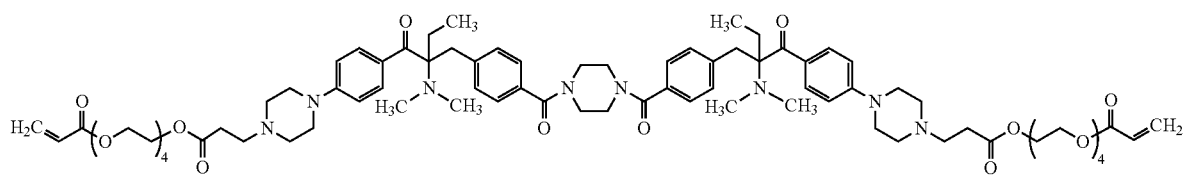

Compound (M1)

Decomposed product

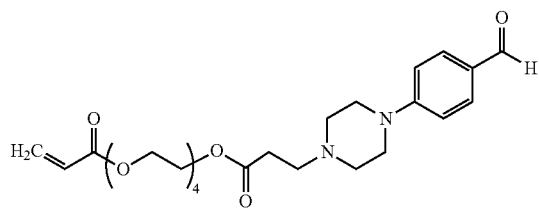

Benzaldehyde compound (2a)

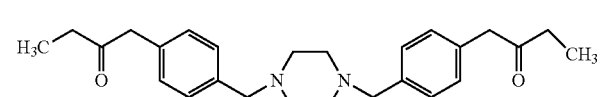

Alkyl benzyl ketone compound (2b)

Similarly, an ethanol solution of each of "Omnipol 910" (polyethylene glycol di{β-4-[4-(2-dimethylamino-2-benzyl) butanoylphenyl]piperazine} propionate, manufactured by Insight High Tecnology Co., Ltd.) and "Irgacure 369" (2-benzyl-2-dimethylamino-1-(4-morpholinophenyl)-butanone-1, manufactured by BASF Inc.), which were used in the comparative examples, was prepared as a standard sample. Also, 1-phenyl-2-butanone, which was a decomposed product of "Omnipol 910" and "Irgacure 369", was synthesized and an ethanol solution thereof was prepared as a standard sample. These standard samples were used for identification, and a calibration curve was formed for calculating the elusion concentrations.

[Method for Evaluating Photocurable Printing Ink Printed Patter: Odor]

The printed matter cured by the curing method described above was cut into a length of 5 cm and a width of 2.5 cm, and 10 segments with this size were prepared. The 10 segments were immediately placed in a collection vial having an outer diameter of 40 mm, a height of 75 mm, an opening inner diameter of 20.1 mm, and a volume of 50 ml, and then the collection vial was closed and stored in a constant-temperature bath of 60° C. for 1 hour to be filled with an odor. Next, the collection vial was allowed to stand until it became room temperature, and then the odor strength

[Chem. 97]

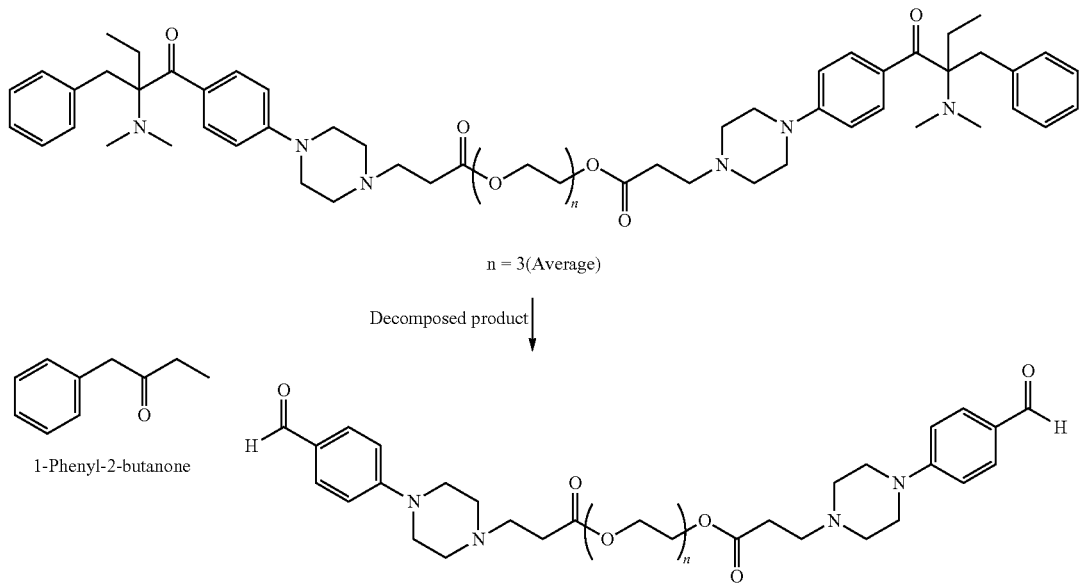

[Chem. 98]

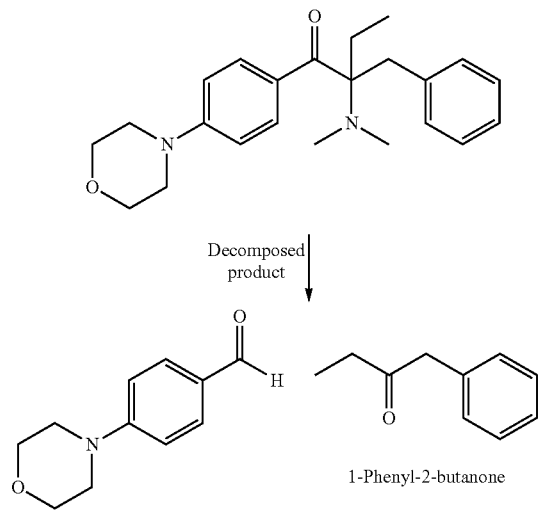

The elusion amount of each of the materials was calculated as described above, and migration was evaluated according to the following criteria.
⊚: Less than 20 ppb
○: 20 to less than 30 ppb
Δ: 30 ppb or more to less than 60 ppb
×: 60 ppb or more of each of samples was evaluated by 10 monitor persons for evaluating the odor strength in 10 ranks.

The odor evaluation results of the 10 persons were averaged to determine the odor strength of each of the samples. This represents that the higher the value, the lower the odor.

⊚: 10 to 9  Δ: 5 to 3
○: 8 to 6  ×: 2 to 1

TABLE 1

|  |  | Example 16 | Example 17 | Example 18 | Example 19 | Example 20 | Example 21 | Example 22 | Example 23 |
|---|---|---|---|---|---|---|---|---|---|
| Pigment | Carbon black | 16.0 | 16.0 | 16.0 | 16.0 | 16.0 | 16.0 | 16.0 | 16.0 |
|  | Phthalocyanine blue | 3.0 | 3.0 | 3.0 | 3.0 | 3.0 | 3.0 | 3.0 | 3.0 |
|  | Dioxazine violet | 2.0 | 2.0 | 2.0 | 2.0 | 2.0 | 2.0 | 2.0 | 2.0 |
| Extender pigment | Talc | 2.0 | 2.0 | 2.0 | 2.0 | 2.0 | 2.0 | 2.0 | 2.0 |
|  | Magnesium carbonate | 2.0 | 2.0 | 2.0 | 2.0 | 2.0 | 2.0 | 2.0 | 2.0 |
| Auxiliary | Polyolefin wax | 2.0 | 2.0 | 2.0 | 2.0 | 2.0 | 2.0 | 2.0 | 2.0 |
|  | Stabilizer solution | 1.0 | 1.0 | 1.0 | 1.0 | 1.0 | 1.0 | 1.0 | 1.0 |
| Photopolymerization initiator | M1 | 3.9 |  |  |  |  |  |  |  |
|  | M4 |  | 3.2 |  |  |  |  |  |  |
|  | M7 |  |  | 3.4 |  |  |  |  |  |
|  | M14 |  |  |  | 3.8 |  |  |  |  |
|  | M23 |  |  |  |  |  | 3.0 |  |  |
|  | M28 |  |  |  |  |  |  | 4.0 |  |
|  | M31 |  |  |  |  |  |  | 5.5 |  |
|  | M32 |  |  |  |  |  |  |  | 5.6 |
|  | α-Hydroxyketone-type initiator | 5.8 | 5.8 | 5.8 | 5.8 | 5.8 | 5.8 | 5.8 | 5.8 |
| Sensitizer | High-molecular-weight tertiary amine compound | 5.0 | 5.0 | 5.0 | 5.0 | 5.0 | 5.0 | 5.0 | 5.0 |
| Monomer | DPHA | 5.0 | 5.0 | 5.0 | 5.0 | 5.0 | 5.0 | 5.0 | 5.0 |
|  | EOTMPTA | 27.4 | 28.1 | 27.9 | 27.5 | 28.3 | 27.3 | 25.8 | 25.7 |
| Binder resin | Urethane acrylate resin | 24.9 | 24.9 | 24.9 | 24.9 | 24.9 | 24.9 | 24.9 | 24.9 |
| Curability* (m/min) |  | 80 | 70 | 70 | 80 | 70 | 70 | 90 | 100 |
| Migration of unreacted photopolymerization initiator |  | ND | ND | ND | ND | ND | ND | ND | ND |
| Migration of benzaldehyde compound (2a) |  | ⊚ | ⊚ | ⊚ | ⊚ | ⊚ | ⊚ | ⊚ | ⊚ |
| Migration of alkyl benzyl ketone compound (2b) |  | ⊚ | ⊚ | ⊚ | ⊚ | ⊚ | ⊚ | ⊚ | ⊚ |
| Migration of 1-phenyl-2-butanone |  | ⊚ | ⊚ | ⊚ | ⊚ | ⊚ | ⊚ | ⊚ | ⊚ |
| Migration of Esacure One |  | ⊚ | ⊚ | ⊚ | ⊚ | ⊚ | ⊚ | ⊚ | ⊚ |
| Odor |  | ○ | ○ | ○ | ○ | ○ | ○ | ○ | ○ |

TABLE 2

|  |  | Example 24 | Example 25 | Example 26 | Example 27 | Example 28 | Example 29 | Example 30 |
|---|---|---|---|---|---|---|---|---|
| Pigment | Carbon black | 16.0 | 16.0 | 16.0 | 16.0 | 16.0 | 16.0 | 16.0 |
|  | Phthalocyanine blue | 3.0 | 3.0 | 3.0 | 3.0 | 3.0 | 3.0 | 3.0 |
|  | Dioxazine violet | 2.0 | 2.0 | 2.0 | 2.0 | 2.0 | 2.0 | 2.0 |
| Extender pigment | Talc | 2.0 | 2.0 | 2.0 | 2.0 | 2.0 | 2.0 | 2.0 |
|  | Magnesium carbonate | 2.0 | 2.0 | 2.0 | 2.0 | 2.0 | 2.0 | 2.0 |
| Auxiliary | Polyolefin wax | 2.0 | 2.0 | 2.0 | 2.0 | 2.0 | 2.0 | 2.0 |
|  | Stabilizer solution | 1.0 | 1.0 | 1.0 | 1.0 | 1.0 | 1.0 | 1.0 |
| Photopolymerization initiator | M41 | 3.9 |  |  |  |  |  |  |
|  | M43 |  | 4.3 |  |  |  |  |  |
|  | M45 |  |  | 5.5 |  |  |  |  |
|  | M50 |  |  |  | 3.6 |  |  |  |
|  | M55 |  |  |  |  | 4.0 |  |  |
|  | M64 |  |  |  |  |  | 4.0 |  |
|  | M79 |  |  |  |  |  |  | 4.0 |
|  | α-Hydroxyketone-type initiator | 5.8 | 5.8 | 5.8 | 5.8 | 5.8 | 5.8 | 5.8 |
| Sensitizer | High-molecular-weight tertiary amine compound | 5.0 | 5.0 | 5.0 | 5.0 | 5.0 | 5.0 | 5.0 |
| Monomer | DPHA | 5.0 | 5.0 | 5.0 | 5.0 | 5.0 | 5.0 | 5.0 |
|  | EOTMPTA | 27.4 | 27.0 | 25.8 | 27.7 | 27.3 | 27.3 | 27.3 |
| Binder resin | Urethane acrylate resin | 24.9 | 24.9 | 24.9 | 24.9 | 24.9 | 24.9 | 24.9 |
| Curability* (m/min) |  | 80 | 70 | 90 | 70 | 80 | 90 | 80 |
| Migration of unreacted photopolymerization initiator |  | ND | ND | ND | ND | ND | ND | ND |
| Migration of benzaldehyde compound (2a) |  | ⊚ | ⊚ | ⊚ | ⊚ | ⊚ | ⊚ | ⊚ |
| Migration of alkyl benzyl ketone compound (2b) |  | ⊚ | ⊚ | ⊚ | ⊚ | ⊚ | ⊚ | ⊚ |
| Migration of 1-phenyl-2-butanone |  | ⊚ | ⊚ | ⊚ | ⊚ | ⊚ | ⊚ | ⊚ |
| Migration of Esacure One |  | ⊚ | ⊚ | ⊚ | ⊚ | ⊚ | ⊚ | ⊚ |
| Odor |  | ○ | ⊚ | ○ | ○ | ⊚ | ⊚ | ⊚ |

TABLE 3

|  |  | Comparative Example 1 | Comparative Example 2 |
|---|---|---|---|
| Pigment | Carbon black | 16.0 | 16.0 |
|  | Phthalocyanine blue | 3.0 | 3.0 |
|  | Dioxazine violate | 2.0 | 2.0 |
| Extender pigment | Talc | 2.0 | 2.0 |
|  | Magnesium carbonate | 2.0 | 2.0 |
| Auxiliary | Polyolefin wax | 2.0 | 2.0 |
|  | Stabilizer solution | 1.0 | 1.0 |
| Photo-polymerization initiator | Irgacure 369 | 1.9 |  |
|  | Omnipol 910 |  | 4.4 |
|  | α-Hydroxyketone-type initiator | 5.8 | 5.8 |
| Sensitizer | High-molecular-weight tertiary amine compound | 5.0 | 5.0 |
| Monomer | DPHA | 5.0 | 5.0 |
|  | EOTMPTA | 29.4 | 26.9 |
| Binder resin | Urethane acrylate resin | 24.9 | 24.9 |
| Curability* (m/min) |  | 100 | 80 |
| Migration of unreacted photopolymerization initiator |  | x | ND |
| Migration of 1-phenyl-2-butanone |  | x | x |
| Migration of Esacure One |  | ⊙ | ⊙ |
| Odor |  | x | Δ |

In the tables, abbreviations are

Carbon black: "Raven 1060 Ultra"

Phthalocyanine blue: blue pigment "FASTOGEN BLUE TGR-1" manufactured by DIC Corporation Dioxazine violet: dioxazine violet "Hostaperm Violet RL 02" manufactured by Clariant Corporation Talc: Hydrated magnesium silicate ("High Filler #5000PJ" manufactured by Matsumura Sangyo Co., Ltd.)

Magnesium carbonate: basic magnesium carbonate ("Magnesium Carbonate TT" manufactured by Naikai Salt Industries Co., Ltd.)

Polyolefin wax: "S-381-N1" manufactured by Shamrock Corporation

Stabilizer solution: mixed solution of 10% by mass of p-methoxyphenol ("Methoquinone") manufactured by Seiko Chemical Co., Ltd. and 90% by amass of ethylene oxide-modified pentaerythritol tetraacrylate ("SR494NS" manufactured by Sartomer Co., Ltd.)

α-Hydroxyketone-type initiator: Oligomer (2-hydroxy-2-methyl-1-[4-(1-methylvinyl)phenyl]propanone), ("Esacure ONE" manufactured by Lamberti Co., Ltd., number-average molecular weight 424.57)

High-molecular-weight tertiary amine compound: "Genopol AB-2" manufactured by RAHN Co., Ltd.)

Irgacure 369: 2-benzyl-2-dimethylamino-1-(4-morpholinophenyl)-butanone-1, number-average molecular weight 367, "Irgacure 369" manufactured by BASF Inc.

Omnipol 910: (polyethylene glycol di{β-4-[4-(2-dimethylamino-2-benzyl)butanoylphenyl]piperazine}propionate, average molecular weight 910), purity 83% by mass ("Omnipol 910" manufactured by Insight High Technology Co., Ltd.)

Urethane acrylate resin: Urethane acrylate resin produced in Production Example 1

DPHA: dipentaerythritol hexaacrylate ("Anilox M-400" manufactured by Toagosei Co., Ltd., 5,000 to 7,000 mPa·s/25° C.)

EOTMPTA: ethylene oxide-modified trimethylolpropane triacrylate ("MIRAMER M3130" manufactured by MIWON Chemical Co., Ltd., viscosity: 50 to 70 mPa·s (25° C.), average number of ethylene oxides added per molecule: 3)

REFERENCE SIGNS LIST 1 cured ink layer
2 milk carton paper
3 milk carton white paper

The invention claimed is:

1. A novel compound having a molecular structure represented by general formula 1 below,

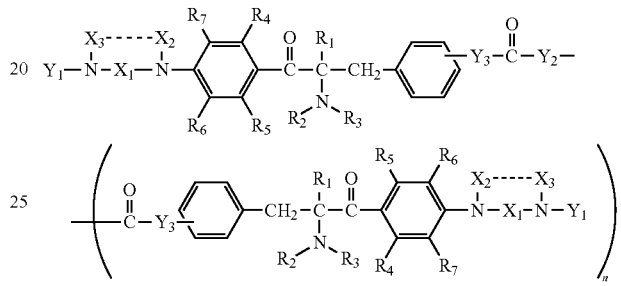

General formula 1 wherein $R_1$ is an alkyl group having 1 to 10 carbon atoms, $R_2$ is an alkyl group having 1 to 12 carbon atoms, a hydroxyalkyl group having 2 to 4 carbon atoms, or an alkyl group having 2 to 4 carbon atoms and substituted by an alkoxy group having 1 or 2 carbon atoms, $R_3$ is an alkyl group having 1 to 12 carbon atoms, a hydroxyalkyl group having 2 to 4 carbon atoms, a methoxyethyl group, or an ethoxyethyl group, $R_2$ and $R_3$ are alkylene groups which are combined to form a cyclic structure together with a nitrogen atom, $R_2$ and $R_3$ are cyclic structure-forming parts which are combined to form a morpholine skeleton, a N-methylpiperazine skeleton, or a 2,6-dimethylmorpholine skeleton together with a nitrogen atom, $R_4$ to $R_7$ are each independently a hydrogen atom, an alkyl group having 1 to 8 carbon atoms, or a phenyl group, $Y_1$ is an alkyl group (y1-1) selected from the group consisting of a dodecyl group, a tridecyl group, a tetradecyl group, a pentadecyl group, a hexadecyl group, a heptadecyl group, an octadecyl group, a 1-methylundecyl group, a 1-chlorododecyl group, a 1,1,1-trichlorododecyl group, a 1-chlorooctadecyl group, a 1,1,1-trichlorooctadecyl group, a 1-hydroxydodecyl group, a 1-hydroxyoctadecyl group, an aralkyl group (y1-2) having 7 to 19 carbon atoms, a structural part represented by structural formulae (y1-3), (y1-4), (y1-5), (y1-6), (y1-7), (y1-8) and (y1-9) below $$R_9-O-(R_8-O)_m-R_8- \qquad (y1-3)$$

in the formula (y1-3), $R_8$ represents an alkylene group having 2 to 4 carbon atoms, $R_9$ represents a hydrogen atom, a phenyl group, or an alkyl group having 1 to 4 carbon atoms, and m represents an integer of 0 to 20, a structural part (y1-4) represented by structural formula (y1-4) below

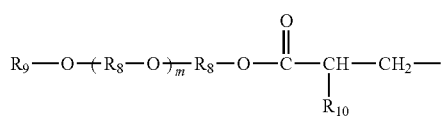
(y1-4)

in the formula (y1-4), $R_8$ represents an alkylene group having 2 to 4 carbon atoms, $R_9$ represents a hydrogen atom, a phenyl group, or an alkyl group having 1 to 4 carbon atoms, $R_{10}$ represents a hydrogen atom or a methyl group, and m represents an integer of 0 to 20, a structural part (y1-5) represented by structural formula (y1-5) below

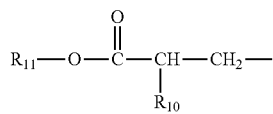
(y1-5)

in the formula (y1-5), $R_{10}$ represents a hydrogen atom or a methyl group, and Ru represents a group selected from the group consisting of a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a 2-ethylbutyl group, an isopentyl group, a 1-methylpentyl group, a 1,3-dimethylbutyl group, a 1-methylhexyl group, an isoheptyl group, a 1,1,3,3-tetramethylbutyl group, a 2,2,4,4-tetramethylbutyl group, a 1-methylheptyl group, a 3-methylheptyl group, a 2-ethylhexyl group, a 1,1,3-trimethylhexyl group, a 1,1,3,3-tetramethylpentyl group, an isodecyl group, a 1-methylundecyl group, a 1,1,3,3,5,5-hexamethylhexyl group, a cycloheptyl group, a cyclohexyl group, a cyclopentyl group, or an aryl group having 6 to 18 carbon atoms, a structural part (y1-6) represented by structural formula (y1-6) below

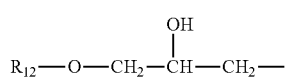
(y1-6)

in the formula (y1-6), $R_{12}$ represents a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a 2-ethylbutyl group, an isopentyl group, a 1-methylpentyl group, a 1,3-dimethylbutyl group, a 1-methylhexyl group, an isoheptyl group, a 1,1,3,3-tetramethylbutyl group, a 2,2,4,4-tetramethylbutyl group, a 1-methylheptyl group, a 3-methylheptyl group, a 2-ethylhexyl group, a 1,1,3-trimethylhexyl group, a 1,1,3,3-tetramethylpentyl group, an isodecyl group, a 1-methylundecyl group, a 1,1,3,3,5,5-hexamethylhexyl group, a cycloheptyl group, a cyclohexyl group, or a cyclopentyl group, a structural part (y1-7) represented by structural formula (y1-7) below

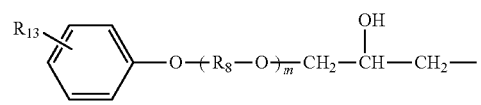
(y1-7)

in the formula (y1-7), $R_8$ represents an alkylene group having 2 to 4 carbon atoms, $R_{13}$ represents a hydrogen atom, an alkyl group having 1 to 6 carbon atoms, or a halogen atom, and m represents an integer of 0 to 20, a structural part (y1-8) represented by structural formula (y1-8) below

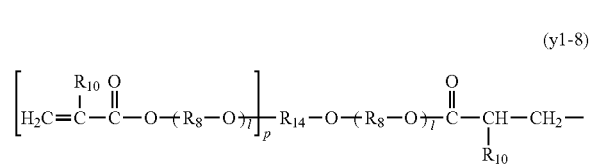
(y1-8)

in the formula (y1-8), $R_8$ each independently represent an alkylene group having 2 to 4 carbon atoms, $R_{10}$ represents a hydrogen atom or a methyl group, $R_{14}$ represents a hydrocarbon group having 3 to 25 carbon atoms and (p+1) bonds, l represents an integer of 0 to 20, and p represents an integer of 1 to 3, or a structural part (y1-9) represented by structural formula (y1-9) below

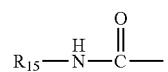
(y1-9)

in the formula (y1-9), $R_{15}$ represents an alkyl group having 4 to 18 carbon atoms, an aliphatic cyclic hydrocarbon group having 6 to 10 carbon atoms, or an aromatic group, $X_1$ is an ethylene group, a 1,3-propylene group, a 1,2-propylene group, or a 2,3-propylene group, $X_2$ is a hydrogen atom or a methyl group, $X_3$ is a hydrogen atom, a methyl group, or an ethyl group, or $X_2$ and $X_3$ integrally represent an ethylene group, a 1,3-propylene group, a 1,2-propylene group, or a 2,3-propylene group while forming a covalent bond in a broken line portion, or $X_1$, $X_2$, and $X_3$ integrally represent a tetravalent aliphatic hydrocarbon group which forms a bicyclo ring together with a nitrogen atom and is represented by structural formula below

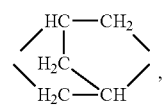

Y2 represents a structural part structural part represented by one selected from the group consisting of formulae (y2-1) to (y2-9) below:

—NH—$R_{16}$—NH—     (y2-1)

in the formula (y2-1), $R_{16}$ represents a linear or cyclic alkylene group having 2 to 18 carbon atoms, a phenylene group, a xylylene group, a phenylene group having an alkyl group having 1 to 3 carbon atoms as a nuclear substituent, or a xylylene group having an alkyl group having 1 to 3 carbon atoms as a nuclear substituent),

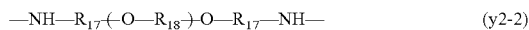 (y2-2)

in the formula (y2-2), $R_{17}$ represents a linear or branched alkylene group having 2 to 6 carbon atoms or a phenylene group, $R_{18}$ represents a linear or branched alkylene group having 2 to 6 carbon atoms or a phenylene group, and q represents an integer of 1 to 22),

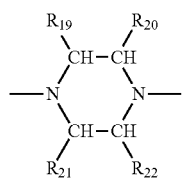 (y2-3)

in the formula (y2-3), $R_{19}$ to $R_{22}$ each independently represent a hydrogen atom or a linear or branched alkyl group having 1 to 3 carbon atoms,

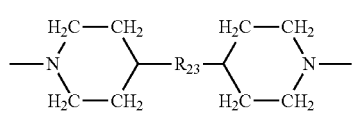 (y2-4)

in the formula (y2-4), $R_{23}$ represents an oxygen atom, a methylene group, an ethylene group, an ethylidene group, a 2,2-propylene group, or a 1,3-propylene group,

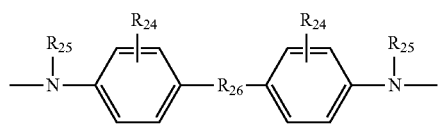 (y2-5)

in the formula (y2-5), $R_{24}$ each independently represent a hydrogen atom or a linear or branched alkyl group having 1 to 3 carbon atoms, $R_{25}$ each independently represent a hydrogen atom or a linear or branched alkyl group having 1 to 3 carbon atoms, and $R_{26}$ represents an oxygen atom, a methylene group, a 2,2-propylene group, a sulfonyl group, or a carbonyl group, or in the general formula 1, n is 2 or 3,

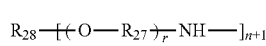 (y2-6)

in the formula (y2-6), $R_{27}$ represents an alkylene group having 2 to 6 carbon atoms, $R_{28}$ represents a hydrocarbon group having 4 to 12 carbon atoms and a number of bonds of (n+1), and r represents an integer of 0 to 3,

 (y2-7)

in the formula (y2-7), $R_{29}$ represents a linear, branched, or cyclic alkylene group having 2 to 18 carbon atoms, a phenylene group, or a xylylene group

 (y2-8)

in the formula (y2-8), $R_{30}$ each independently represent an alkylene group having 2 to 6 carbon atoms, and q represents an integer of 1 to 20), or in the general formula 1, n is 2 or 3,

 (y2-9)

in the formula (y2-9), $R_{31}$ represents a hydrocarbon group having 4 to 12 carbon atoms and a number of bonds of (n+1)), $R_{32}$ represents an alkylene group having 2 to 6 carbon atoms, and s represents an integer of 0 to 3, $Y_3$ represents a single bond, an alkylene group having 1 to 3 carbon atoms, or an alkylidene group having 1 to 3 carbon atoms, and n represents an integer of 1 when Y2 is one of (y2-1) to (y2-5), (y2-7) and (y2-8), or an integer of 2 or 3 when Y2 is one of (y2-6) or (y2-9).

2. The novel compound according to claim 1, wherein in the general formula 1, the total number of structural parts represented by structural formula 1a below is 300 to 2000, Structural formula 1a

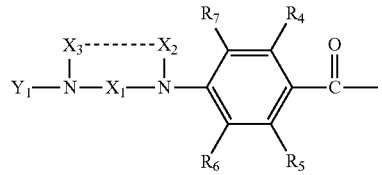

in the structural formula 1a, $R_4$ to $R_7$, $X_1$ to $X_3$, and $Y_1$ represent the same meanings as in the general formula 1.

3. A polymerization initiator comprising the novel compound according to claim 1.

4. A photocurable composition comprising the photopolymerization initiator according to claim 3 and a photocurable compound as essential components.

5. A cured product produced by curing the photocurable composition according to claim 4.

6. A photocurable printing ink comprising the photocurable composition according to claim 4.

* * * * *